US007531317B2

(12) United States Patent
Fox et al.

(10) Patent No.: US 7,531,317 B2

(45) Date of Patent: May 12, 2009

(54) FLUORESCENCE POLARIZATION ASSAY TO DETECT PROTEASE CLEAVAGE

(75) Inventors: Brian G. Fox, Madison, WI (US); Paul G. Blommel, Blue Mounds, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 88 days.

(21) Appl. No.: 10/997,651

(22) Filed: Nov. 24, 2004

(65) Prior Publication Data

US 2005/0227306 A1 Oct. 13, 2005

Related U.S. Application Data

(60) Provisional application No. 60/607,210, filed on Sep. 3, 2004, provisional application No. 60/524,812, filed on Nov. 25, 2003.

(51) Int. Cl.

| | |
|---|---|
| ***C12Q 1/37*** | (2006.01) |
| ***C12N 15/00*** | (2006.01) |
| ***C12N 5/00*** | (2006.01) |
| ***C12P 21/06*** | (2006.01) |
| ***C07H 21/02*** | (2006.01) |

(52) U.S. Cl. ...................... 435/23; 435/320.1; 435/325; 435/69.1; 536/23.1; 530/412

(58) Field of Classification Search ...................... None
See application file for complete search history.

(56) References Cited

U.S. PATENT DOCUMENTS

| | | | | |
|---|---|---|---|---|
| 5,932,474 | A * | 8/1999 | Tsien et al. | 435/320.1 |
| 6,008,378 | A | 12/1999 | Tsien et al. | |
| 6,054,271 | A | 4/2000 | Tsien et al. | |
| 6,410,255 | B1 * | 6/2002 | Pollok et al. | 435/23 |
| 6,451,569 | B1 | 9/2002 | Tsien et al. | |
| 2002/0132248 | A1 * | 9/2002 | Rothschild et al. | 435/6 |
| 2003/0083373 | A1 | 5/2003 | Tsien et al. | |
| 2003/0147810 | A1 * | 8/2003 | Ross et al. | 424/9.6 |
| 2003/0207264 | A1 * | 11/2003 | Packard et al. | 435/6 |

OTHER PUBLICATIONS

Terpe K (2003; published online Nov. 7, 2002) Overview of tag protein fusions: from molecular and biochemical fundamentals to commercial systems. Appl Microbiol Biotechnol, vol. 60, pp. 523-533.*

Griffin BA et al (Jul. 10, 1998) Specific covalent labeling of recombinant protein molecules inside live cells. Science, vol. 281, pp. 269-272.*

Adams et al., ((2002), New Biarsenical Ligands and Tetracysteine Motifs for Protein Labeling In Vitro and In Vivo: Synthesis and Biological Applications, *J. Am. Chem. Soc.*, 124:6063-6076.

Basbaum et al., (1996), Focalized proteolysis: spatial and temporal regulation of extracellular matrix degradation at the cell surface, *Current Opinion in Cell Biology*, 8:731-738.

Bickerstaff et al., (1993), Protease Activity and Autodigestion (Autolysis) Assays Using Coomassie Blue Dye Binding, *Analytical Biochemistry*, 210:155-158.

Birkedal-Hansen, Henning, (1995), Proteolytic remodeling of extracellular matrix, *Current Opinion in Cell Biology*, 7:728-735.

Blommel et al., (2004), Multiplexing, Fluorescence Polarization Assays to Increase Information Content Per Screen: Applications for Screening Steroid Hormone Receptors, *The Society for Biomolecular Screening*, 9(4):294-302.

Checovich et al., (1995), *Nature*, 375:254-256.

Constans, Aileen, (2002), Protein Purification II: Affinity Tags, *The Scientist*, 16[4]:37.

Cordingley et al., (1990), Substrate Requirements of Human Rhinovirus 3C Protease for Peptide Cleavage in Vitro, *The Journal of Biological Chemistry*, vol. 265, No. 16, pp. 9062-9065.

Deng et al., (2000), Substrate Specificity of Human Collagenase 3 Assessed Using a Phage-displayed Peptide Library, *The Journal of Biological Chemistry*, vol. 275, No. 40, pp. 31422-31427.

Deutsch et al., (2000), Analysis of Enzyme Kinetics in Inidividual Living Cells Utilizing Fluorescence Intensity and Polarization Measurements, *Cytometry*, 39:36-44.

Dian et al., (2002), Overcoming protein instability problems during fusion protein cleavage, *Life Science News 10*, pp. 1-5.

Drott et al., (2004), New pET expression vectors and HRV 3C Protease for efficient fusion tag removal, *Novaen InNovations*, pp. 3-15.

Fields et al., (1987), Sequence Specificity of Human Skin Fibroblast Collagenase, *The Journal of Biological Chemistry*, vol. 262, No. 23, pp. 6221-6226.

Hammerström et al., (2002), Rapid screening for improved solubility of small human proteins produced as fusion proteins in *Escherichia coli, Protein Science*, 11:313-321.

Kridel et al., (2001), Substrate Hydrolysis by Matrix Metalloproteinase-9, *The Journal of Biological Chemistry*, vol. 276, No. 23, pp. 20572-20578.

Levine et al., (1999), Homogenous fluorescence readouts for miniaturized high-throughput screening: theory and practice (Abstract), *Analytical Biochemistry*, vol. 247, Issue 1, pp. 83-88.

Lucast et al., (2001), Large-Scale Purification of a Stable Form of Recombinant Tobacco Etch Virus Protease, *BioTechniques*, 30:544-554.

Menges et al., (1997), Continuous Assay of Proteases Using a Microtiter Plate Fluorescence Reader, *Analytical Biochemistry*, 254:144-147.

(Continued)

*Primary Examiner*—Lisa J Hobbs

(74) *Attorney, Agent, or Firm*—Joseph T. Leone, Esq.; DeWitt Ross & Stevens S.C.

(57) ABSTRACT

The invention discloses a method of determining protease activity, in real time, using fluorescence polarization technology. In particular, the invention provides vectors and a method for their use, which expresses uncharacterized proteins conjugated to a fluorescence tag, which binds specifically to a fluorescent ligand. Cleavage of the recombinant protein results in a fragment of the expressed peptide and results in a change in fluorescence polarization of the fluorophore. The rate of change in fluorescence polarization can be measured in real time and is equivalent to the rate of protease cleavage.

33 Claims, 23 Drawing Sheets

OTHER PUBLICATIONS

Maidmen et al., (1999), Matrix Metalloproteinase Homologues from *Arabidopsis thaliana, The Journal of Biological Chemistry*, vol. 264, No. 49, pp. 34706-34710.

Mickowska et al., (2000), Fast, isotope-free methods for the assay of thiamine-binding proteins and for the determination of their affinities to thiamine-related compounds, *J. Biochem. Biophys. Methods*, 44:95-107.

Netzel-Arnett et al., (1991), Sequence Specificities of Human Fibroblast and Neutrophil Collagenases, *the Journal of Biological Chemistry*, vol. 266, No. 11, 00. 6747-6755.

Panvera Corporation, Madison, Wisconsin, Chapter 1, Fluorescence Polarization, Chapter 1, Introduction pp. 1-7.

Panvera Corporation, Madison, Wisconsin, Chapter 5, Fluorescence Polarization, Degradative Assays, pp. 5-2-5-14.

Panvera Corporation, Madison, Wisconsin, FIAsH™-$EDT_2$ Labeling Kit, Part #P3050 Literature, pp. 1-4.

Pope et al., (1999), Homogenous Fluorescence readouts for miniaturized high-throughput screening: theory and practice (Abstract), *Drug Discovery Today*, vol. 4, Issue 8, pp. 350-362.

Schade et al., (1996), BODIPY-α-Casein, a pH-Independent Protein Substrate for Protease Assays Using Fluorescence Polarization (Abstract), *Analytical Biochemistry*, vol. 243, Issue 1, pp. 1-7.

Simeonov et al., (2002), Enzyme Assays by Fluorescence Polarization n the Presence of Polyarginine: Study of Kinase, Phosphatase, and Protease Reactions, *Analytical Biochemistry*, 304:193-199.

Stevens et al., (2000), Design of high-throughput methods of protein production for structural biology, *Structure*, 8:R177-R-185.

Terpe, K., (2003), Overview of tag protein fusions: from molecular and biochemical fundamentals to commercial systems, *Appl. Microbiol. Biotechnol.*, 60:523-533.

Thompson et al., (2000), A BODIPY Fluorescent Microplate Assay for Measuring Activity of Calpains and Other Proteases, *Analytical Biochemistry*, 279:170-178.

* cited by examiner

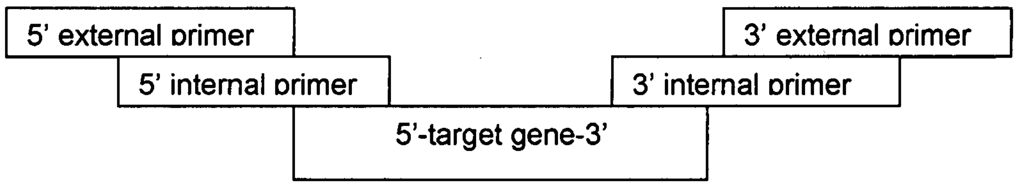

5' external primer:
5'-GGGGACAAGTTTGTACAAAAAAGCAGGCTCCGAAAACCTGTACTTCCAG-3' (SEQ. ID. NO: 32)
5' internal primer: AACCTGTACTTCCAGTCCAAAATCGAAGAAGGTAAACTGGTAATC (SEQ. ID. NO : 33)
5' end of target gene (example shown is *E. coli* MBP): (SEQ. ID. NO: 34) AAAATCGAAGAAGGTAAACTGGTAATCTGGATT...

3' external primer (SEQ. ID. NO : 35) 3'-CTGGGTCGAAAGAACATGTTTCACCAGGGG-5'
3' internal primer CGGGACTTTCTGCGCGTCTGAATCCTGGGTCGAAAGAACATG (SEQ. ID. NO: 36)
3' end of target gene ...CTACTTCGGGACTTTCTGCGCGTCTG (SEQ. ID. NO: 37)

FIG. 15

FIG. 17A
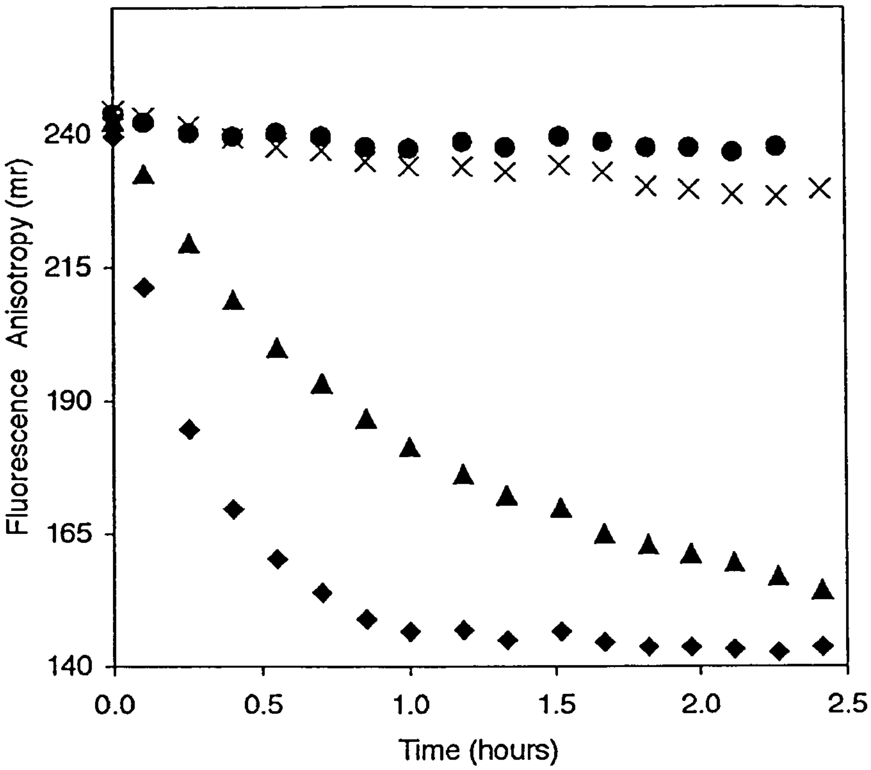
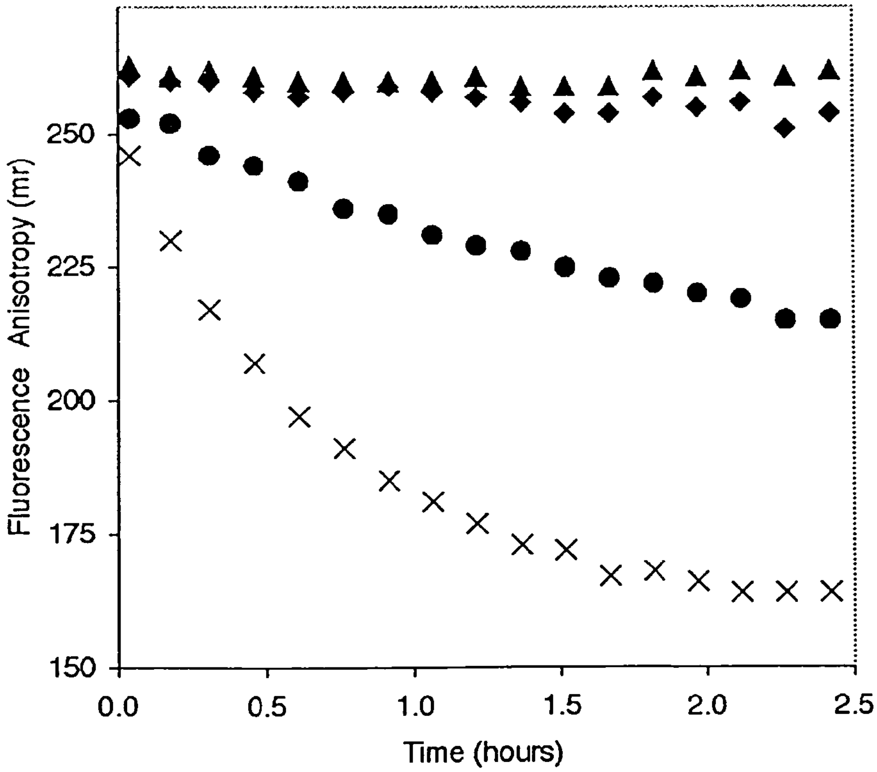
FIG. 17B

FIG. 19A
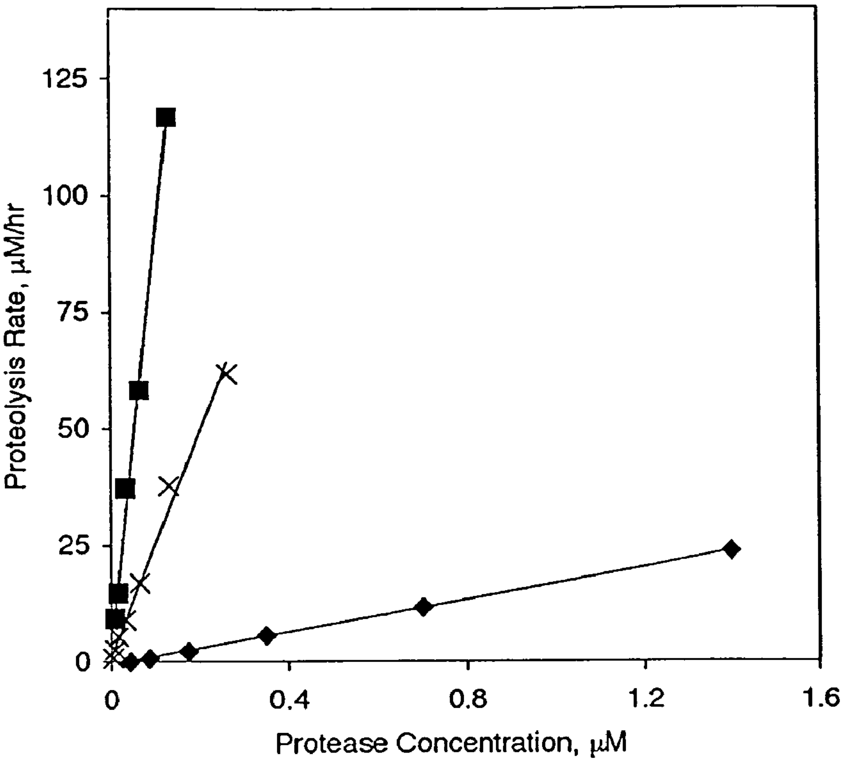
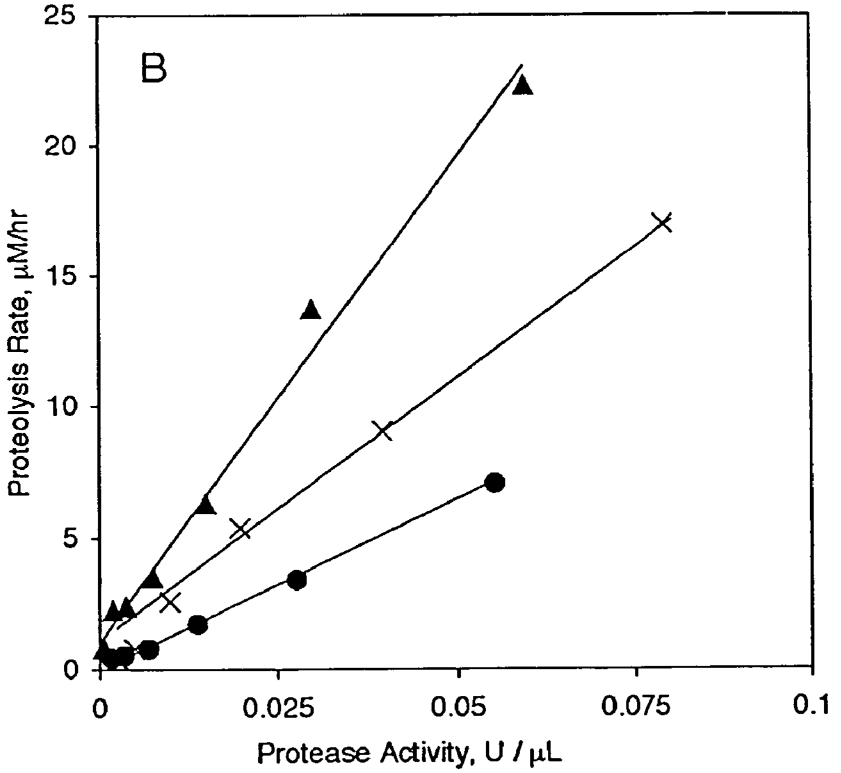
FIG. 19B

FIG. 21A
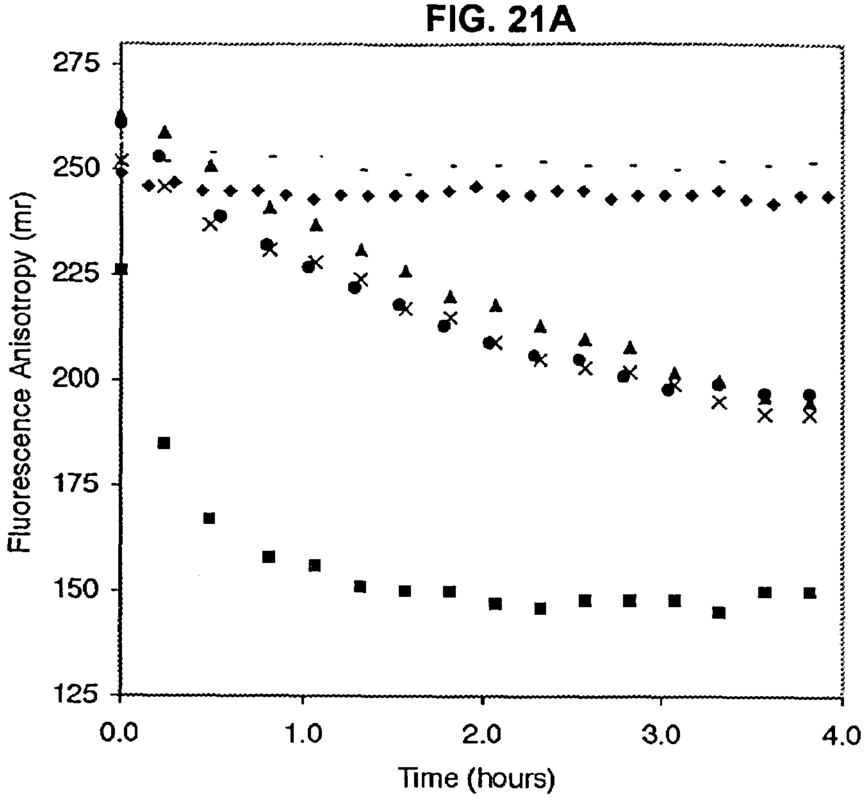
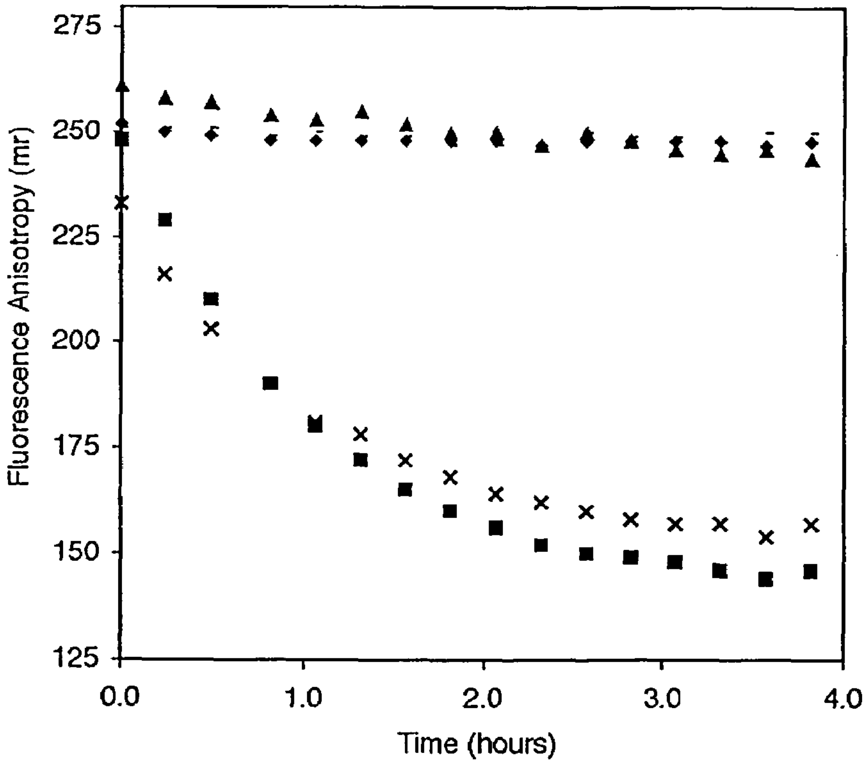
FIG. 21B

FIG. 23A
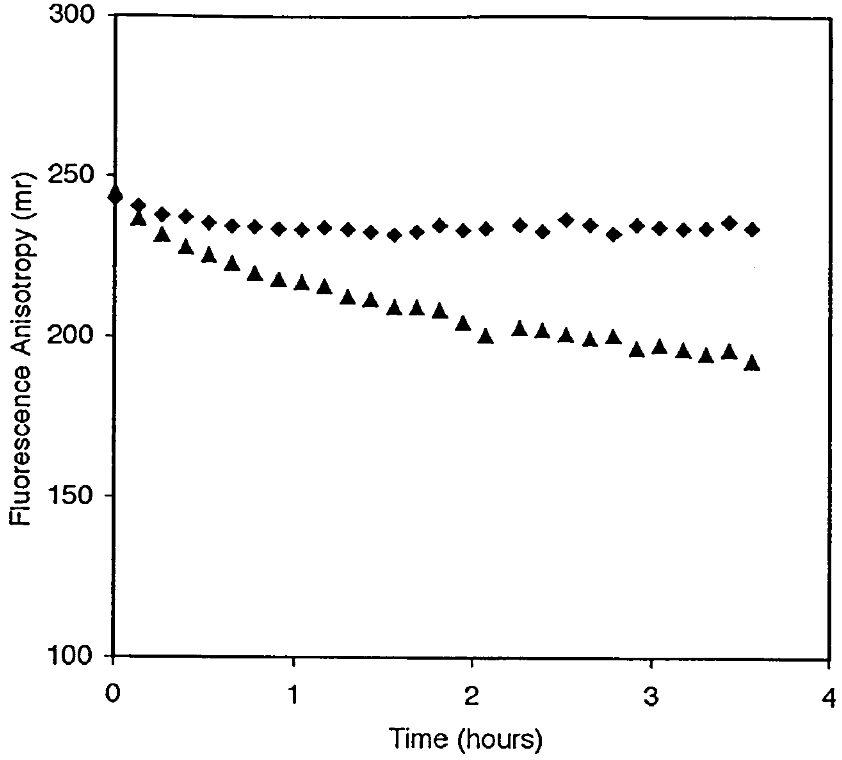
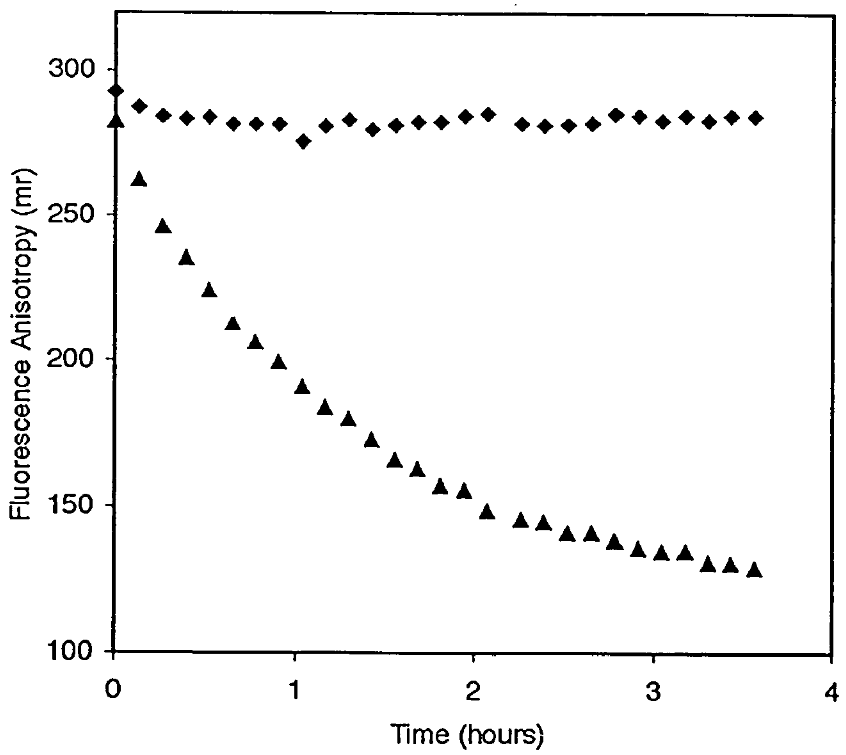
FIG. 23B

SEQUENCE LISTING

```
<160> NUMBER OF SEQ ID NOS: 38

<210> SEQ ID NO 1
<211> LENGTH: 6
<212> TYPE: PRT
<213> ORGANISM: Artificial
<220> FEATURE:
<223> OTHER INFORMATION: tetraCyc peptide motif that complexes with an
      arsenic-containing compound to yield a fluorophore
<220> FEATURE:
<221> NAME/KEY: MISC_FEATURE
```

-continued

<222> LOCATION: (3)..(4)
<223> OTHER INFORMATION: "Xaa" at positions 3 and 4 can be any amino acid

<400> SEQUENCE: 1

Cys Cys Xaa Xaa Cys Cys
1 5

<210> SEQ ID NO 2
<211> LENGTH: 6372
<212> TYPE: DNA
<213> ORGANISM: Artificial
<220> FEATURE:
<223> OTHER INFORMATION: pVP-14 expression plasmid

<400> SEQUENCE: 2
agatctcgat cccgcgaaat taatacgact cactataggg agaccacaac ggtttccctc 60
tagaaataat tttgtttaac tttaagaagg agatatacat atgtcgtact accatcacca 120
tcaccatcac ctcgaatcat gttgcccagg atgctgtaca agtttgtaca aaaaagctga 180
acgagaaacg taaaatgata taaatatcaa tatattaaat tagattttgc ataaaaaaca 240
gactacataa tactgtaaaa cacaacatat ccagtcacta tggcggccgc attaggcacc 300
ccaggcttta cactttatgc ttccggctcg tataatgtgt ggattttgag ttaggatccg 360
tcgagatttt caggagctaa ggaagctaaa atggagaaaa aaatcactgg atataccacc 420
gttgatatat cccaatggca tcgtaaagaa cattttgagg catttcagtc agttgctcaa 480
tgtacctata accagaccgt tcagctggat attacggcct ttttaaagac cgtaaagaaa 540
aataagcaca agttttatcc ggcctttatt cacattcttg cccgcctgat gaatgctcat 600
ccggaattcc gtatggcaat gaaagacggt gagctggtga tatgggatag tgttcaccct 660
tgttacaccg ttttccatga gcaaactgaa acgttttcat cgctctggag tgaataccac 720
gacgatttcc ggcagtttct acacatatat tcgcaagatg tggcgtgtta cggtgaaaac 780
ctggcctatt tccctaaagg gtttattgag aatatgtttt tcgtctcagc caatccctgg 840
gtgagtttca ccagttttga tttaaacgtg gccaatatgg acaacttctt cgcccccgtt 900
ttcaccatgg gcaaatatta tacgcaaggc gacaaggtgc tgatgccgct ggcgattcag 960
gttcatcatg ccgtctgtga tggcttccat gtcggcagaa tgcttaatga attacaacag 1020
tactgcgatg agtggcaggg cggggcgtaa agatctggat ccggcttact aaaagccaga 1080
taacagtatg cgtatttgcg cgctgatttt tgcggtataa gaatatatac tgatatgtat 1140
acccgaagta tgtcaaaaag aggtgtgcta tgaagcagcg tattacagtg acagttgaca 1200
gcgacagcta tcagttgctc aaggcatata tgatgtcaat atctccggtc tggtaagcac 1260
aaccatgcag aatgaagccc gtcgtctgcg tgccgaacgc tggaaagcgg aaaatcagga 1320
agggatggct gaggtcgccc ggtttattga aatgaacggc tcttttgctg acgagaacag 1380
ggactggtga aatgcagttt aaggtttaca cctataaaag agagagccgt tatcgtctgt 1440
ttgtggatgt acagagtgat attattgaca cgcccgggcg acggatggtg atccccctgg 1500
ccagtgcacg tctgctgtca gataaagtct cccgtgaact ttacccggtg gtgcatatcg 1560
gggatgaaag ctggcgcatg atgaccaccg atatggccag tgtgccggtc tccgttatcg 1620
gggaagaagt ggctgatctc agccaccgcg aaaatgacat caaaaacgcc attaacctga 1680
tgttctgggg aatataaatg tcaggctccc ttatacacag ccagtctgca ggtcgaccat 1740
agtgactgga tatgttgtgt tttacagtat tatgtagtct gtttttttatg caaaatctaa 1800

-continued

```
tttaatatat tgatatttat atcattttac gtttctcgtt cagctttctt gtacaaagtg   1860
gttgattcga ggctgctaac aaagcccgaa aggaagctga gttggctgct gccaccgctg   1920
agcaataact agcataaccc cttggggcct ctaaacgggt cttgaggggt tttttgctga   1980
aaggaggaac tatatccgga tatccacagg acgggtgtgg tcgccatgat cgcgtagtcg   2040
atagtggctc caagtagcga agcgagcagg actgggcggc ggccaaagcg gtcggacagt   2100
gctccgagaa cgggtgcgca tagaaattgc atcaacgcat atagcgctag cagcacgcca   2160
tagtgactgg cgatgctgtc ggaatggacg atatcccgca agaggcccgg cagtaccggc   2220
ataaccaagc ctatgcctac agcatccagg gtgacggtgc cgaggatgac gatgagcgca   2280
ttgttagatt tcatacacgg tgcctgactg cgttagcaat ttaactgtga taaactaccg   2340
cattaaagct tatcgatgat aagctgtcaa acatgagaat tcttgaagac gaaagggcct   2400
cgtgatacgc ctatttttat aggttaatgt catgataata atggtttctt agacgtcagg   2460
tggcactttt cggggaaatg tgcgcggaac ccctatttgt ttatttttct aaatacattc   2520
aaatatgtat ccgctcatga gacaataacc ctgataaatg cttcaataat attgaaaaag   2580
gaagagtatg agtattcaac atttccgtgt cgcccttatt ccctttttttg cggcattttg   2640
ccttcctgtt tttgctcacc cagaaacgct ggtgaaagta aaagatgctg aagatcagtt   2700
gggtgcacga gtgggttaca tcgaactgga tctcaacagc ggtaagatcc ttgagagttt   2760
tcgccccgaa gaacgttttc caatgatgag cacttttaaa gttctgctat gtggcgcggt   2820
attatcccgt gttgacgccg ggcaagagca actcggtcgc cgcatacact attctcagaa   2880
tgacttggtt gagtactcac cagtcacaga aaagcatctt acggatggca tgacagtaag   2940
agaattatgc agtgctgcca taaccatgag tgataacact gcggccaact tacttctgac   3000
aacgatcgga ggaccgaagg agctaaccgc ttttttgcac aacatggggg atcatgtaac   3060
tcgccttgat cgttgggaac cggagctgaa tgaagccata ccaaacgacg agcgtgacac   3120
cacgatgcct gcagcaatgg caacaacgtt gcgcaaacta ttaactggcg aactacttac   3180
tctagcttcc cggcaacaat taatagactg gatggaggcg gataaagttg caggaccact   3240
tctgcgctcg gcccttccgg ctggctggtt tattgctgat aaatctggag ccggtgagcg   3300
tgggtctcgc ggtatcattg cagcactggg gccagatggt aagccctccc gtatcgtagt   3360
tatctacacg acggggagtc aggcaactat ggatgaacga aatagacaga tcgctgagat   3420
aggtgcctca ctgattaagc attggtaact gtcagaccaa gtttactcat atatacttta   3480
gattgattta aaacttcatt tttaatttaa aaggatctag gtgaagatcc tttttgataa   3540
tctcatgacc aaaatccctt aacgtgagtt ttcgttccac tgagcgtcag accccgtaga   3600
aaagatcaaa ggatcttctt gagatccttt ttttctgcgc gtaatctgct gcttgcaaac   3660
aaaaaaacca ccgctaccag cggtggtttg tttgccggat caagagctac caactctttt   3720
tccgaaggta actggcttca gcagagcgca gataccaaat actgtccttc tagtgtagcc   3780
gtagttaggc caccacttca agaactctgt agcaccgcct acatacctcg ctctgctaat   3840
cctgttacca gtggctgctg ccagtggcga taagtcgtgt cttaccgggt tggactcaag   3900
acgatagtta ccggataagg cgcagcggtc gggctgaacg gggggttcgt gcacacagcc   3960
cagcttggag cgaacgacct acaccgaact gagataccta cagcgtgagc tatgagaaag   4020
cgccacgctt cccgaaggga gaaaggcgga caggtatccg gtaagcggca gggtcggaac   4080
aggagagcgc acgagggagc ttccaggggg aaacgcctgg tatctttata gtcctgtcgg   4140
gtttcgccac ctctgacttg agcgtcgatt tttgtgatgc tcgtcagggg ggcggagcct   4200
```

-continued

```
atggaaaaac gccagcaacg cggccttttt acggttcctg gccttttgct ggccttttgc   4260
tcacatgttc tttcctgcgt tatcccctga ttctgtggat aaccgtatta ccgcctttga   4320
gtgagctgat accgctcgcc gcagccgaac gaccgagcgc agcgagtcag tgagcgagga   4380
agcggaagag cgcctgatgc ggtattttct ccttacgcat ctgtgcggta tttcacaccg   4440
catatatggt gcactctcag tacaatctgc tctgatgccg catagttaag ccagtataca   4500
ctccgctatc gctacgtgac tgggtcatgg ctgcgccccg acacccgcca acacccgctg   4560
acgcgccctg acgggcttgt ctgctcccgg catccgctta cagacaagct gtgaccgtct   4620
ccgggagctg catgtgtcag aggttttcac cgtcatcacc gaaacgcgcg aggcagctgc   4680
ggtaaagctc atcagcgtgg tcgtgaagcg attcacagat gtctgcctgt tcatccgcgt   4740
ccagctcgtt gagtttctcc agaagcgtta atgtctggct tctgataaag cgggccatgt   4800
taagggcggt tttttcctgt ttggtcactg atgcctccgt gtaaggggga tttctgttca   4860
tgggggtaat gataccgatg aaacgagaga ggatgctcac gatacgggtt actgatgatg   4920
aacatgcccg gttactggaa cgttgtgagg gtaaacaact ggcggtatgg atgcggcggg   4980
accagagaaa aatcactcag ggtcaatgcc agcgcttcgt taatacagat gtaggtgttc   5040
cacagggtag ccagcagcat cctgcgatgc agatccggaa cataatggtg cagggcgctg   5100
acttccgcgt ttccagactt tacgaaacac ggaaaccgaa gaccattcat gttgttgctc   5160
aggtcgcaga cgttttgcag cagcagtcgc ttcacgttcg ctcgcgtatc ggtgattcat   5220
tctgctaacc agtaaggcaa ccccgccagc ctagccgggt cctcaacgac aggagcacga   5280
tcatgcgcac ccgtggccag gacccaacgc tgcccgagat gcgccgcgtg cggctgctgg   5340
agatggcgga cgcgatggat atgttctgcc aagggttggt ttgcgcattc acagttctcc   5400
gcaagaattg attggctcca attcttggag tggtgaatcc gttagcgagg tgccgccggc   5460
ttccattcag gtcgaggtgg cccggctcca tgcaccgcga cgcaacgcgg ggaggcagac   5520
aaggtatagg gcggcgccta caatccatgc caacccgttc catgtgctcg ccgaggcggc   5580
ataaatcgcc gtgacgatca gcggtccagt gatcgaagtt aggctggtaa gagccgcgag   5640
cgatccttga agctgtccct gatggtcgtc atctacctgc ctggacagca tggcctgcaa   5700
cgcgggcatc ccgatgccgc cggaagcgag aagaatcata atggggaagg ccatccagcc   5760
tcgcgtcgcg aacgccagca agacgtagcc cagcgcgtcg gccgccatgc cggcgataat   5820
ggcctgcttc tcgccgaaac gtttggtggc gggaccagtg acgaaggctt gagcgagggc   5880
gtgcaagatt ccgaataccg caagcgacag gccgatcatc gtcgcgctcc agcgaaagcg   5940
gtcctcgccg aaaatgaccc agagcgctgc cggcacctgt cctacgagtt gcatgataaa   6000
gaagacagtc ataagtgcgg cgacgatagt catgccccgc gcccaccgga aggagctgac   6060
tgggttgaag gctctcaagg gcatcggtcg atcgacgctc tcccttatgc gactcctgca   6120
ttaggaagca gcccagtagt aggttgaggc cgttgagcac cgccgccgca aggaatggtg   6180
catgcaagga gatggcgccc aacagtcccc cggccacggg gcctgccacc atacccacgc   6240
cgaaacaagc gctcatgagc ccgaagtggc gagcccgatc ttccccatcg gtgatgtcgg   6300
cgatataggc gccagcaacc gcacctgtgg cgccggtgat gccggccacg atgcgtccgg   6360
cgtagaggat cg                                                       6372
```

<210> SEQ ID NO 3
<211> LENGTH: 48
<212> TYPE: DNA

-continued

<213> ORGANISM: Artificial
<220> FEATURE:
<223> OTHER INFORMATION: "FLUF" forward primer for PCR

<400> SEQUENCE: 3
tgttgcccag gatgctgtac aagtttgtac aaaaaagctg aacgagaa 48

<210> SEQ ID NO 4
<211> LENGTH: 41
<212> TYPE: DNA
<213> ORGANISM: Artificial
<220> FEATURE:
<223> OTHER INFORMATION: "pD17FR" reverse primer for PCR

<400> SEQUENCE: 4
tgattcgagg tgatggtgat ggtgatggta gtacgacata t 41

<210> SEQ ID NO 5
<211> LENGTH: 7685
<212> TYPE: DNA
<213> ORGANISM: Artificial
<220> FEATURE:
<223> OTHER INFORMATION: pVP-15 expression plasmid

<400> SEQUENCE: 5
cctcgagaaa tcataaaaaa tttatttgct ttgtgagcgg ataacaatta taatagattc 60
aattgtgagc ggataacaat ttcacacaga attcattaaa gaggagaaat taaccatggg 120
taaagaaacc gctgctgcga aatttgaacg ccagcacatg gactcgccac cgcatcatca 180
ccatcaccat tcaaaaatcg aagaaggtaa actggtaatc tggattaacg gcgataaagg 240
ctataacggt ctcgctgaag tcggtaagaa attcgagaaa gataccggaa ttaaagtcac 300
cgttgagcat ccggataaac tggaagagaa attcccacag gttgcggcaa ctggcgatgg 360
ccctgacatt atcttctggg cacacgaccg ctttggtggc tacgctcaat ctggcctgtt 420
ggctgaaatc accccggaca aagcgttcca ggacaagctg tatccgttta cctgggatgc 480
cgtacgttac aacggcaagc tgattgctta cccgatcgct gttgaagcgt tatcgctgat 540
ttataacaaa gatctgctgc cgaacccgcc aaaaacctgg gaagagatcc cggcgctgga 600
taaagaactg aaagcgaaag gtaagagcgc gctgatgttc aacctgcaag aaccgtactt 660
cacctggccg ctgattgctg ctgacggggg ttatgcgttc aagtatgaaa acggcaagta 720
cgacattaaa gacgtgggcg tggataacgc tggcgcgaaa gcgggtctga ccttcctggt 780
tgacctgatt aaaaacaaac acatgaatgc agacaccgat tactccatcg cagaagctgc 840
ctttaataaa ggcgaaacag cgatgaccat caacggcccg tgggcatggt ccaacatcga 900
caccagcaaa gtgaattatg gtgtaacggt actgccgacc ttcaagggtc aaccatccaa 960
accgttcgtt ggcgtgctga gcgcaggtat taacgccgcc agtccgaaca aagagctggc 1020
aaaagagttc ctcgaaaact atctgctgac tgatgaaggt ctggaagcgg ttaataaaga 1080
caaaccgctg ggtgccgtag cgctgaagtc ttacgaggaa gagttggcga aagatccacg 1140
tattgccgcc actatggaaa acgcccagaa aggtgaaatc atgccgaaca tcccgcagat 1200
gtccgctttc tggtatgccg tgcgtactgc ggtgatcaac gccgccagcg gtcgtcagac 1260
tgtcgatgaa gccctgaaag acgcgcagac taattcgagc tcgaacaaca acgaaaacct 1320
gtacttccag tcccaccacc atcaccatca ctgttgccca ggatgctgta caagtttgta 1380
caaaaaagct gaacgagaaa cgtaaaatga tataaatatc aatatattaa attagatttt 1440
gcataaaaaa cagactacat aatactgtaa aacacaacat atccagtcac tatggcggcc 1500

-continued

```
gcattaggca ccccaggctt tacactttat gctttcggct cgtataatgt gtggattttg   1560
agttaggatc cgtcgagatt ttcaggagct aaggaagcta aaatggagaa aaaaatcact   1620
ggatatacca ccgttgatat atcccaatgg catcgtaaag aacattttga ggcatttcag   1680
tcagttgctc aatgtaccta taaccagacc gttcagctgg atattacggc ctttttaaag   1740
accgtaaaga aaaataagca caagttttat ccggccttta ttcacattct tgcccgcctg   1800
atgaatgctc atccggaatt ccgtatggca atgaaagacg gtgagctggt gatatgggat   1860
agtgttcacc cttgttacac cgttttccat gagcaaactg aaacgttttc atcgctctgg   1920
agtgaatacc acgacgattt ccggcagttt ctacacatat attcgcaaga tgtggcgtgt   1980
tacggtgaaa acctggccta tttccctaaa gggtttattg agaatatgtt tttcgtctca   2040
gccaatccct gggtgagttt caccagtttt gatttaaacg tggccaatat ggacaacttc   2100
ttcgcccccg ttttcaccat gggcaaatat tatacgcaag gcgacaaggt gctgatgccg   2160
ctggcgattc aggttcatca tgccgtttgt gatggcttcc atgtcggcag aatgcttaat   2220
gaattacaac agtactgcga tgagtggcag ggcggggcgt aaagatctgg atccggctta   2280
ctaaaagcca gataacagta tgcgtatttg cgcgctgatt tttgcggtat aagaatatat   2340
actgatatgt atacccgaag tatgtcaaaa agaggtatgc tatgaagcag cgtattacag   2400
tgacagttga cagcgacagc tatcagttgc tcaaggcata tatgatgtca atatctccgg   2460
tctggtaagc acaaccatgc agaatgaagc ccgtcgtctg cgtgccgaac gctggaaagc   2520
ggaaaatcag gaagggatgg ctgaggtcgc ccggtttatt gaaatgaacg gctcttttgc   2580
tgacgagaac aggggctggt gaaatgcagt ttaaggttta cacctataaa agagagagcc   2640
gttatcgtct gtttgtggat gtacagagtg atattattga cacgcccggg cgacggatgg   2700
tgatccccct ggccagtgca cgtctgctgt cagataaagt ctcccgtgaa ctttacccgg   2760
tggtgcatat cggggatgaa agctggcgca tgatgaccac cgatatggcc agtgtgccgg   2820
tctccgttat cggggaagaa gtggctgatc tcagccaccg cgaaaatgac atcaaaaacg   2880
ccattaacct gatgttctgg ggaatataaa tgtcaggctc ccttatacac agccagtctg   2940
caggtcgacc atagtgactg gatatgttgt gttttacagt attatgtagt ctgtttttta   3000
tgcaaaatct aatttaatat attgatattt atatcatttt acgtttctcg ttcagctttc   3060
ttgtacaaag tggtgatggc gcgcctgtag gacgtcgacg gtaccatcga tacgcgttcg   3120
aagcttaatt agctgagctt ggactcctgt tgatagatcc agtaatgacc tcagaactcc   3180
atctggattt gttcagaacg ctcggttgcc gccgggcgtt ttttattggt gagaatccaa   3240
gctagcttgg cgagattttc aggagctaag gaagctaaaa tggagaaaaa aatcactgga   3300
tataccaccg ttgatatatc ccaatggcat cgtaaagaac attttgaggc atttcagtca   3360
gttgctcaat gtacctataa ccagaccgtt cagctggata ttacggcctt tttaaagacc   3420
gtaaagaaaa ataagcacaa gttttatccg gcctttattc acattcttgc ccgcctgatg   3480
aatgctcatc cggaatttcg tatggcaatg aaagacggtg agctggtgat atgggatagt   3540
gttcaccctt gttacaccgt tttccatgag caaactgaaa cgttttcatc gctctggagt   3600
gaataccacg acgatttccg gcagtttcta cacatatatt cgcaagatgt ggcgtgttac   3660
ggtgaaaacc tggcctattt ccctaaaggg tttattgaga atatgttttt cgtctcagcc   3720
aatccctggg tgagtttcac cagttttgat ttaaacgtgg ccaatatgga caacttcttc   3780
gcccccgttt tcaccatggg caaatattat acgcaaggcg acaaggtgct gatgccgctg   3840
```

-continued

```
gcgattcagg ttcatcatgc cgtttgtgat ggcttccatg tcggcagaat gcttaatgaa   3900
ttacaacagt actgcgatga gtggcagggc ggggcgtaat ttttttaagg cagttattgg   3960
tgcccttaaa cgcctggggt aatgactctc tagcttgagg catcaaataa aacgaaaggc   4020
tcagtcgaaa gactgggcct ttcgttttat ctgttgtttg tcggtgaacg ctctcctgag   4080
taggacaaat ccgccctcta gattacgtgc agtcgatgat aagctgtcaa acatgagaat   4140
tgtgcctaat gagtgagcta acttacatta attgcgttgc gctcactgcc cgctttccag   4200
tcgggaaacc tgtcgtgcca gctgcattaa tgaatcggcc aacgcgcggg gagaggcggt   4260
ttgcgtattg ggcgccaggg tggtttttct tttcaccagt gagacgggca acagctgatt   4320
gcccttcacc gcctggccct gagagagttg cagcaagcgg tccacgctgg tttgccccag   4380
caggcgaaaa tcctgtttga tggtggttaa cggcgggata taacatgagc tgtcttcggt   4440
atcgtcgtat cccactaccg agatatccgc accaacgcgc agcccggact cggtaatggc   4500
gcgcattgcg cccagcgcca tctgatcgtt ggcaaccagc atcgcagtgg gaacgatgcc   4560
ctcattcagc atttgcatgg tttgttgaaa accggacatg gcactccagt cgccttcccg   4620
ttccgctatc ggctgaattt gattgcgagt gagatattta tgccagccag ccagacgcag   4680
acgcgccgag acagaactta atgggcccgc taacagcgcg atttgctggt gacccaatgc   4740
gaccagatgc tccacgccca gtcgcgtacc gtcttcatgg gagaaaataa tactgttgat   4800
gggtgtctgg tcagagacat caagaaataa cgccggaaca ttagtgcagg cagcttccac   4860
agcaatggca tcctggtcat ccagcggata gttaatgatc agcccactga cgcgttgcgc   4920
gagaagattg tgcaccgccg ctttacaggc ttcgacgccg cttcgttcta ccatcgacac   4980
caccacgctg gcacccagtt gatcggcgcg agatttaatc gccgcgacaa tttgcgacgg   5040
cgcgtgcagg gccagactgg aggtggcaac gccaatcagc aacgactgtt tgcccgccag   5100
ttgttgtgcc acgcggttgg gaatgtaatt cagctccgcc atcgccgctt ccactttttc   5160
ccgcgttttc gcagaaacgt ggctggcctg gttcaccacg cgggaaacgg tctgataaga   5220
gacaccggca tactctgcga catcgtataa cgttactggt ttcacattca ccaccctgaa   5280
ttgactctct tccgggcgct atcatgccat accgcgaaag gttttgcacc attcgatggt   5340
gtcggaattt cgggcagcgt tgggtcctgg ccacgggtgc gcatgatcta gagctgcctc   5400
gcgcgtttcg gtgatgacgg tgaaaacctc tgacacatgc agctcccgga gacggtcaca   5460
gcttgtctgt aagcggatgc cgggagcaga caagcccgtc agggcgcgtc agcgggtgtt   5520
ggcgggtgtc ggggcgcagc catgacccag tcacgtagcg atagcggagt gtatactggc   5580
ttaactatgc ggcatcagag cagattgtac tgagagtgca ccatatgcgg tgtgaaatac   5640
cgcacagatg cgtaaggaga aaataccgca tcaggcgctc ttccgcttcc tcgctcactg   5700
actcgctgcg ctcggtcgtt cggctgcggc gagcggtatc agctcactca aaggcggtaa   5760
tacggttatc cacagaatca ggggataacg caggaaagaa catgtgagca aaaggccagc   5820
aaaaggccag gaaccgtaaa aaggccgcgt tgctggcgtt tttccatagg ctccgccccc   5880
ctgacgagca tcacaaaaat cgacgctcaa gtcagaggtg gcgaaacccg acaggactat   5940
aaagatacca ggcgtttccc cctggaagct ccctcgtgcg ctctcctgtt ccgaccctgc   6000
cgcttaccgg atacctgtcc gcctttctcc cttcgggaag cgtggcgctt tctcatagct   6060
cacgctgtag gtatctcagt tcggtgtagg tcgttcgctc caagctgggc tgtgtgcacg   6120
aaccccccgt tcagcccgac cgctgcgcct tatccggtaa ctatcgtctt gagtccaacc   6180
cggtaagaca cgacttatcg ccactggcag cagccactgg taacaggatt agcagagcga   6240
```

-continued

```
ggtatgtagg cggtgctaca gagttcttga agtggtggcc taactacggc tacactagaa   6300

ggacagtatt tggtatctgc gctctgctga agccagttac cttcggaaaa agagttggta   6360

gctcttgatc cggcaaacaa accaccgctg gtagcggtgg tttttttgtt tgcaagcagc   6420

agattacgcg cagaaaaaaa ggatctcaag aagatccttt gatcttttct acggggtctg   6480

acgctcagtg gaacgaaaac tcacgttaag ggattttggt catgagatta tcaaaaagga   6540

tcttcaccta gatcctttta aattaaaaat gaagttttaa atcaatctaa agtatatatg   6600

agtaaacttg gtctgacagt taccaatgct taatcagtga ggcacctatc tcagcgatct   6660

gtctatttcg ttcatccata gttgcctgac tccccgtcgt gtagataact acgatacggg   6720

agggcttacc atctggcccc agtgctgcaa tgataccgcg agacccacgc tcaccggctc   6780

cagatttatc agcaataaac cagccagccg gaagggccga gcgcagaagt ggtcctgcaa   6840

ctttatccgc ctccatccag tctattaatt gttgccggga agctagagta agtagttcgc   6900

cagttaatag tttgcgcaac gttgttgcca ttgctacagg catcgtggtg tcacgctcgt   6960

cgtttggtat ggcttcattc agctccggtt cccaacgatc aaggcgagtt acatgatccc   7020

ccatgttgtg caaaaaagcg gttagctcct tcggtcctcc gatcgttgtc agaagtaagt   7080

tggccgcagt gttatcactc atggttatgg cagcactgca taattctctt actgtcatgc   7140

catccgtaag atgcttttct gtgactggtg agtactcaac caagtcattc tgagaatagt   7200

gtatgcggcg accgagttgc tcttgcccgg cgtcaatacg ggataatacc gcgccacata   7260

gcagaacttt aaaagtgctc atcattggaa aacgttcttc ggggcgaaaa ctctcaagga   7320

tcttaccgct gttgagatcc agttcgatgt aacccactcg tgcacccaac tgatcttcag   7380

catcttttac tttcaccagc gtttctgggt gagcaaaaac aggaaggcaa aatgccgcaa   7440

aaaagggaat aagggcgaca cggaaatgtt gaatactcat actcttcctt tttcaatatt   7500

attgaagcat ttatcagggt tattgtctca tgagcggata catatttgaa tgtatttaga   7560

aaaataaaca aataggggtt ccgcgcacat ttccccgaaa agtgccacct gacgtctaag   7620

aaaccattat tatcatgaca ttaacctata aaaataggcg tatcacgagg ccctttcgtc   7680

ttcac                                                               7685
```

<210> SEQ ID NO 6
<211> LENGTH: 7675
<212> TYPE: DNA
<213> ORGANISM: Artificial
<220> FEATURE:
<223> OTHER INFORMATION: pVP13-GW expression plasmid

<400> SEQUENCE: 6

```
cctcgagaaa tcataaaaaa tttatttgct ttgtgagcgg ataacaatta taatagattc     60

aattgtgagc ggataacaat ttcacacaga attcattaaa gaggagaaat taaccatggg    120

taaagaaacc gctgctgcga aatttgaacg ccagcacatg gactcgccac cgcatcatca    180

ccatcaccat tcaaaaatcg aagaaggtaa actggtaatc tggattaacg gcgataaagg    240

ctataacggt ctcgctgaag tcggtaagaa attcgagaaa gataccggaa ttaaagtcac    300

cgttgagcat ccggataaac tggaagagaa attcccacag gttgcggcaa ctggcgatgg    360

ccctgacatt atcttctggg cacacgaccg ctttggtggc tacgctcaat ctggcctgtt    420

ggctgaaatc accccggaca aagcgttcca ggacaagctg tatccgttta cctgggatgc    480

cgtacgttac aacggcaagc tgattgctta cccgatcgct gttgaagcgt tatcgctgat    540
```

-continued

```
ttataacaaa gatctgctgc cgaacccgcc aaaaacctgg gaagagatcc cggcgctgga    600
taaagaactg aaagcgaaag gtaagagcgc gctgatgttc aacctgcaag aaccgtactt    660
cacctggccg ctgattgctg ctgacggggg ttatgcgttc aagtatgaaa acggcaagta    720
cgacattaaa gacgtgggcg tggataacgc tggcgcgaaa gcgggtctga ccttcctggt    780
tgacctgatt aaaaacaaac acatgaatgc agacaccgat tactccatcg cagaagctgc    840
ctttaataaa ggcgaaacag cgatgaccat caacggcccg tgggcatggt ccaacatcga    900
caccagcaaa gtgaattatg gtgtaacggt actgccgacc ttcaagggtc aaccatccaa    960
accgttcgtt ggcgtgctga gcgcaggtat taacgccgcc agtccgaaca aagagctggc   1020
aaaagagttc ctcgaaaact atctgctgac tgatgaaggt ctggaagcgg ttaataaaga   1080
caaaccgctg ggtgccgtag cgctgaagtc ttacgaggaa gagttggcga aagatccacg   1140
tattgccgcc actatggaaa acgcccagaa aggtgaaatc atgccgaaca tcccgcagat   1200
gtccgctttc tggtatgccg tgcgtactgc ggtgatcaac gccgccagcg gtcgtcagac   1260
tgtcgatgaa gccctgaaag acgcgcagac taattcgagc tcgaacaaca acaacaataa   1320
caataacaac aacctcggga tcgacgaaaa cctgtacctc acaagtttgt acaaaaaagc   1380
tgaacgagaa acgtaaaatg atataaatat caatatatta aattagattt tgcataaaaa   1440
acagactaca taatactgta aaacacaaca tatccagtca ctatggcggc cgcattaggc   1500
accccaggct ttacacttta tgctttcggc tcgtataatg tgtggatttt gagttaggat   1560
ccgtcgagat tttcaggagc taaggaagct aaaatggaga aaaaaatcac tggatatacc   1620
accgttgata tatcccaatg gcatcgtaaa gaacattttg aggcatttca gtcagttgct   1680
caatgtacct ataaccagac cgttcagctg gatattacgg cctttttaaa gaccgtaaag   1740
aaaaataagc acaagtttta tccggccttt attcacattc ttgcccgcct gatgaatgct   1800
catccggaat tccgtatggc aatgaaagac ggtgagctgg tgatatggga tagtgttcac   1860
ccttgttaca ccgttttcca tgagcaaact gaaacgtttt catcgctctg gagtgaatac   1920
cacgacgatt tccggcagtt tctacacata tattcgcaag atgtggcgtg ttacggtgaa   1980
aacctggcct atttccctaa agggtttatt gagaatatgt ttttcgtctc agccaatccc   2040
tgggtgagtt tcaccagttt tgatttaaac gtggccaata tggacaactt cttcgccccc   2100
gttttcacca tgggcaaata ttatacgcaa ggcgacaagg tgctgatgcc gctggcgatt   2160
caggttcatc atgccgtttg tgatggcttc catgtcggca gaatgcttaa tgaattacaa   2220
cagtactgcg atgagtggca gggcggggcg taaagatctg gatccggctt actaaaagcc   2280
agataacagt atgcgtattt gcgcgctgat ttttgcggta taagaatata tactgatatg   2340
tatacccgaa gtatgtcaaa aagaggtatg ctatgaagca gcgtattaca gtgacagttg   2400
acagcgacag ctatcagttg ctcaaggcat atatgatgtc aatatctccg gtctggtaag   2460
cacaaccatg cagaatgaag cccgtcgtct gcgtgccgaa cgctggaaag cggaaaatca   2520
ggaagggatg gctgaggtcg cccggtttat tgaaatgaac ggctcttttg ctgacgagaa   2580
caggggctgg tgaaatgcag tttaaggttt acacctataa aagagagagc cgttatcgtc   2640
tgtttgtgga tgtacagagt gatattattg acacgcccgg gcgacggatg gtgatccccc   2700
tggccagtgc acgtctgctg tcagataaag tctcccgtga actttacccg gtggtgcata   2760
tcggggatga aagctggcgc atgatgacca ccgatatggc cagtgtgccg gtctccgtta   2820
tcggggaaga agtggctgat ctcagccacc gcgaaaatga catcaaaaac gccattaacc   2880
tgatgttctg gggaatataa atgtcaggct cccttataca cagccagtct gcaggtcgac   2940
```

-continued

```
catagtgact ggatatgttg tgttttacag tattatgtag tctgtttttt atgcaaaatc   3000
taatttaata tattgatatt tatatcattt tacgtttctc gttcagcttt cttgtacaaa   3060
gtggtgatgg cgcgcctgta ggacgtcgac ggtaccatcg atacgcgttc gaagcttaat   3120
tagctgagct tggactcctg ttgatagatc cagtaatgac ctcagaactc catctggatt   3180
tgttcagaac gctcggttgc cgccgggcgt tttttattgg tgagaatcca agctagcttg   3240
gcgagatttt caggagctaa ggaagctaaa atggagaaaa aaatcactgg atataccacc   3300
gttgatatat cccaatggca tcgtaaagaa cattttgagg catttcagtc agttgctcaa   3360
tgtacctata accagaccgt tcagctggat attacggcct ttttaaagac cgtaaagaaa   3420
aataagcaca agttttatcc ggcctttatt cacattcttg cccgcctgat gaatgctcat   3480
ccggaatttc gtatggcaat gaaagacggt gagctggtga tatgggatag tgttcaccct   3540
tgttacaccg ttttccatga gcaaactgaa acgttttcat cgctctggag tgaataccac   3600
gacgatttcc ggcagtttct acacatatat tcgcaagatg tggcgtgtta cggtgaaaac   3660
ctggcctatt tccctaaagg gtttattgag aatatgtttt tcgtctcagc caatccctgg   3720
gtgagtttca ccagttttga tttaaacgtg gccaatatgg acaacttctt cgcccccgtt   3780
ttcaccatgg gcaaatatta tacgcaaggc gacaaggtgc tgatgccgct ggcgattcag   3840
gttcatcatg ccgtttgtga tggcttccat gtcggcagaa tgcttaatga attacaacag   3900
tactgcgatg agtggcaggg cggggcgtaa tttttttaag gcagttattg gtgcccttaa   3960
acgcctgggg taatgactct ctagcttgag gcatcaaata aaacgaaagg ctcagtcgaa   4020
agactgggcc tttcgtttta tctgttgttt gtcggtgaac gctctcctga gtaggacaaa   4080
tccgccctct agattacgtg cagtcgatga taagctgtca aacatgagaa ttgtgcctaa   4140
tgagtgagct aacttacatt aattgcgttg cgctcactgc ccgctttcca gtcgggaaac   4200
ctgtcgtgcc agctgcatta atgaatcggc caacgcgcgg ggagaggcgg tttgcgtatt   4260
gggcgccagg gtggtttttc ttttcaccag tgagacgggc aacagctgat tgcccttcac   4320
cgcctggccc tgagagagtt gcagcaagcg gtccacgctg gtttgcccca gcaggcgaaa   4380
atcctgtttg atggtggtta acggcgggat ataacatgag ctgtcttcgg tatcgtcgta   4440
tcccactacc gagatatccg caccaacgcg cagcccggac tcggtaatgg cgcgcattgc   4500
gcccagcgcc atctgatcgt tggcaaccag catcgcagtg ggaacgatgc cctcattcag   4560
catttgcatg gtttgttgaa aaccggacat ggcactccag tcgccttccc gttccgctat   4620
cggctgaatt tgattgcgag tgagatattt atgccagcca gccagacgca gacgcgccga   4680
gacagaactt aatgggcccg ctaacagcgc gatttgctgg tgacccaatg cgaccagatg   4740
ctccacgccc agtcgcgtac cgtcttcatg ggagaaaata atactgttga tgggtgtctg   4800
gtcagagaca tcaagaaata acgccggaac attagtgcag gcagcttcca cagcaatggc   4860
atcctggtca tccagcggat agttaatgat cagcccactg acgcgttgcg cgagaagatt   4920
gtgcaccgcc gctttacagg cttcgacgcc gcttcgttct accatcgaca ccaccacgct   4980
ggcacccagt tgatcggcgc gagatttaat cgccgcgaca atttgcgacg gcgcgtgcag   5040
ggccagactg gaggtggcaa cgccaatcag caacgactgt ttgcccgcca gttgttgtgc   5100
cacgcggttg ggaatgtaat tcagctccgc catcgccgct tccacttttt cccgcgtttt   5160
cgcagaaacg tggctggcct ggttcaccac gcgggaaacg gtctgataag agacaccggc   5220
atactctgcg acatcgtata acgttactgg tttcacattc accaccctga attgactctc   5280
```

-continued

```
ttccgggcgc tatcatgcca taccgcgaaa ggttttgcac cattcgatgg tgtcggaatt   5340
tcgggcagcg ttgggtcctg gccacgggtg cgcatgatct agagctgcct cgcgcgtttc   5400
ggtgatgacg gtgaaaacct ctgacacatg cagctcccgg agacggtcac agcttgtctg   5460
taagcggatg ccgggagcag acaagcccgt cagggcgcgt cagcgggtgt tggcgggtgt   5520
cggggcgcag ccatgaccca gtcacgtagc gatagcggag tgtatactgg cttaactatg   5580
cggcatcaga gcagattgta ctgagagtgc accatatgcg gtgtgaaata ccgcacagat   5640
gcgtaaggag aaaataccgc atcaggcgct cttccgcttc ctcgctcact gactcgctgc   5700
gctcggtcgt tcggctgcgg cgagcggtat cagctcactc aaaggcggta atacggttat   5760
ccacagaatc aggggataac gcaggaaaga acatgtgagc aaaaggccag caaaaggcca   5820
ggaaccgtaa aaaggccgcg ttgctggcgt ttttccatag gctccgcccc cctgacgagc   5880
atcacaaaaa tcgacgctca agtcagaggt ggcgaaaccc gacaggacta taaagatacc   5940
aggcgtttcc ccctggaagc tccctcgtgc gctctcctgt tccgaccctg ccgcttaccg   6000
gatacctgtc cgcctttctc ccttcgggaa gcgtggcgct ttctcatagc tcacgctgta   6060
ggtatctcag ttcggtgtag gtcgttcgct ccaagctggg ctgtgtgcac gaaccccccg   6120
ttcagcccga ccgctgcgcc ttatccggta actatcgtct tgagtccaac ccggtaagac   6180
acgacttatc gccactggca gcagccactg gtaacaggat tagcagagcg aggtatgtag   6240
gcggtgctac agagttcttg aagtggtggc ctaactacgg ctacactaga aggacagtat   6300
ttggtatctg cgctctgctg aagccagtta ccttcggaaa aagagttggt agctcttgat   6360
ccggcaaaca aaccaccgct ggtagcggtg gtttttttgt ttgcaagcag cagattacgc   6420
gcagaaaaaa aggatctcaa gaagatcctt tgatcttttc tacggggtct gacgctcagt   6480
ggaacgaaaa ctcacgttaa gggattttgg tcatgagatt atcaaaaagg atcttcacct   6540
agatcctttt aaattaaaaa tgaagtttta aatcaatcta aagtatatat gagtaaactt   6600
ggtctgacag ttaccaatgc ttaatcagtg aggcacctat ctcagcgatc tgtctatttc   6660
gttcatccat agttgcctga ctccccgtcg tgtagataac tacgatacgg gagggcttac   6720
catctggccc cagtgctgca atgataccgc gagacccacg ctcaccggct ccagatttat   6780
cagcaataaa ccagccagcc ggaagggccg agcgcagaag tggtcctgca actttatccg   6840
cctccatcca gtctattaat tgttgccggg aagctagagt aagtagttcg ccagttaata   6900
gtttgcgcaa cgttgttgcc attgctacag gcatcgtggt gtcacgctcg tcgtttggta   6960
tggcttcatt cagctccggt tcccaacgat caaggcgagt tacatgatcc cccatgttgt   7020
gcaaaaaagc ggttagctcc ttcggtcctc cgatcgttgt cagaagtaag ttggccgcag   7080
tgttatcact catggttatg gcagcactgc ataattctct tactgtcatg ccatccgtaa   7140
gatgcttttc tgtgactggt gagtactcaa ccaagtcatt ctgagaatag tgtatgcggc   7200
gaccgagttg ctcttgcccg gcgtcaatac gggataatac cgcgccacat agcagaactt   7260
taaaagtgct catcattgga aaacgttctt cggggcgaaa actctcaagg atcttaccgc   7320
tgttgagatc cagttcgatg taacccactc gtgcacccaa ctgatcttca gcatctttta   7380
ctttcaccag cgtttctggg tgagcaaaaa caggaaggca aaatgccgca aaaaagggaa   7440
taagggcgac acggaaatgt tgaatactca tactcttcct ttttcaatat tattgaagca   7500
tttatcaggg ttattgtctc atgagcggat acatatttga atgtatttag aaaaataaac   7560
aaataggggt tccgcgcaca tttccccgaa aagtgccacc tgacgtctaa gaaaccatta   7620
ttatcatgac attaacctat aaaaataggc gtatcacgag gccctttcgt cttca        7675
```

-continued

<210> SEQ ID NO 7
<211> LENGTH: 4751
<212> TYPE: DNA
<213> ORGANISM: Artificial
<220> FEATURE:
<223> OTHER INFORMATION: "pQE-80" expression plasmid; available commercially from Quiagen

<400> SEQUENCE: 7

```
ctcgagaaat cataaaaaat ttatttgctt tgtgagcgga taacaattat aatagattca     60

attgtgagcg gataacaatt tcacacagaa ttcattaaag aggagaaatt aactatgaga    120

ggatcgcatc accatcacca tcacggatcc gcatgcgagc tcggtacccc gggtcgacct    180

gcagccaagc ttaattagct gagcttggac tcctgttgat agatccagta atgacctcag    240

aactccatct ggatttgttc agaacgctcg gttgccgccg ggcgtttttt attggtgaga    300

atccaagcta gcttggcgag attttcagga gctaaggaag ctaaaatgga gaaaaaaatc    360

actggatata ccaccgttga tatatcccaa tggcatcgta aagaacattt tgaggcattt    420

cagtcagttg ctcaatgtac ctataaccag accgttcagc tggatattac ggccttttta    480

aagaccgtaa agaaaaataa gcacaagttt tatccggcct ttattcacat tcttgcccgc    540

ctgatgaatg ctcatccgga atttcgtatg gcaatgaaag acggtgagct ggtgatatgg    600

gatagtgttc acccttgtta caccgttttc catgagcaaa ctgaaacgtt ttcatcgctc    660

tggagtgaat accacgacga tttccggcag tttctacaca tatattcgca agatgtggcg    720

tgttacggtg aaaacctggc ctatttccct aaagggttta ttgagaatat gtttttcgtc    780

tcagccaatc cctgggtgag tttcaccagt tttgatttaa acgtggccaa tatggacaac    840

ttcttcgccc ccgttttcac catgggcaaa tattatacgc aaggcgacaa ggtgctgatg    900

ccgctggcga ttcaggttca tcatgccgtt tgtgatggct tccatgtcgg cagaatgctt    960

aatgaattac aacagtactg cgatgagtgg cagggcgggg cgtaattttt ttaaggcagt   1020

tattggtgcc cttaaacgcc tggggtaatg actctctagc ttgaggcatc aaataaaacg   1080

aaaggctcag tcgaaagact gggcctttcg ttttatctgt tgtttgtcgg tgaacgctct   1140

cctgagtagg acaaatccgc cctctagatt acgtgcagtc gatgataagc tgtcaaacat   1200

gagaattgtg cctaatgagt gagctaactt acattaattg cgttgcgctc actgcccgct   1260

ttccagtcgg gaaacctgtc gtgccagctg cattaatgaa tcggccaacg cgcggggaga   1320

ggcggtttgc gtattgggcg ccagggtggt ttttcttttc accagtgaga cgggcaacag   1380

ctgattgccc ttcaccgcct ggccctgaga gagttgcagc aagcggtcca cgctggtttg   1440

ccccagcagg cgaaaatcct gtttgatggt ggttaacggc gggatataac atgagctgtc   1500

ttcggtatcg tcgtatccca ctaccgagat atccgcacca acgcgcagcc cggactcggt   1560

aatggcgcgc attgcgccca gcgccatctg atcgttggca accagcatcg cagtgggaac   1620

gatgccctca ttcagcattt gcatggtttg ttgaaaaccg gacatggcac tccagtcgcc   1680

ttcccgttcc gctatcggct gaatttgatt gcgagtgaga tatttatgcc agccagccag   1740

acgcagacgc gccgagacag aacttaatgg gcccgctaac agcgcgattt gctggtgacc   1800

caatgcgacc agatgctcca cgcccagtcg cgtaccgtct tcatgggaga aaataatact   1860

gttgatgggt gtctggtcag agacatcaag aaataacgcc ggaacattag tgcaggcagc   1920

ttccacagca atggcatcct ggtcatccag cggatagtta atgatcagcc cactgacgcg   1980

ttgcgcgaga agattgtgca ccgccgcttt acaggcttcg acgccgcttc gttctaccat   2040
```

-continued

```
cgacaccacc acgctggcac ccagttgatc ggcgcgagat ttaatcgccg cgacaatttg   2100
cgacggcgcg tgcagggcca gactggaggt ggcaacgcca atcagcaacg actgtttgcc   2160
cgccagttgt tgtgccacgc ggttgggaat gtaattcagc tccgccatcg ccgcttccac   2220
tttttcccgc gttttcgcag aaacgtggct ggcctggttc accacgcggg aaacggtctg   2280
ataagagaca ccggcatact ctgcgacatc gtataacgtt actggtttca cattcaccac   2340
cctgaattga ctctcttccg ggcgctatca tgccataccg cgaaaggttt tgcaccattc   2400
gatggtgtcg gaatttcggg cagcgttggg tcctggccac gggtgcgcat gatctagagc   2460
tgcctcgcgc gtttcggtga tgacggtgaa aacctctgac acatgcagct cccggagacg   2520
gtcacagctt gtctgtaagc ggatgccggg agcagacaag cccgtcaggg cgcgtcagcg   2580
ggtgttggcg ggtgtcgggg cgcagccatg acccagtcac gtagcgatag cggagtgtat   2640
actggcttaa ctatgcggca tcagagcaga ttgtactgag agtgcaccat atgcggtgtg   2700
aaataccgca cagatgcgta aggagaaaat accgcatcag gcgctcttcc gcttcctcgc   2760
tcactgactc gctgcgctcg gtcgttcggc tgcggcgagc ggtatcagct cactcaaagg   2820
cggtaatacg gttatccaca gaatcagggg ataacgcagg aaagaacatg tgagcaaaag   2880
gccagcaaaa ggccaggaac cgtaaaaagg ccgcgttgct ggcgtttttc cataggctcc   2940
gcccccctga cgagcatcac aaaaatcgac gctcaagtca gaggtggcga aacccgacag   3000
gactataaag ataccaggcg tttccccctg gaagctccct cgtgcgctct cctgttccga   3060
ccctgccgct taccggatac ctgtccgcct ttctcccttc gggaagcgtg gcgctttctc   3120
atagctcacg ctgtaggtat ctcagttcgg tgtaggtcgt tcgctccaag ctgggctgtg   3180
tgcacgaacc ccccgttcag cccgaccgct gcgccttatc cggtaactat cgtcttgagt   3240
ccaacccggt aagacacgac ttatcgccac tggcagcagc cactggtaac aggattagca   3300
gagcgaggta tgtaggcggt gctacagagt tcttgaagtg gtggcctaac tacggctaca   3360
ctagaaggac agtatttggt atctgcgctc tgctgaagcc agttaccttc ggaaaaagag   3420
ttggtagctc ttgatccggc aaacaaacca ccgctggtag cggtggtttt tttgtttgca   3480
agcagcagat tacgcgcaga aaaaaaggat ctcaagaaga tcctttgatc ttttctacgg   3540
ggtctgacgc tcagtggaac gaaaactcac gttaagggat tttggtcatg agattatcaa   3600
aaaggatctt cacctagatc cttttaaatt aaaaatgaag ttttaaatca atctaaagta   3660
tatatgagta aacttggtct gacagttacc aatgcttaat cagtgaggca cctatctcag   3720
cgatctgtct atttcgttca tccatagttg cctgactccc cgtcgtgtag ataactacga   3780
tacgggaggg cttaccatct ggccccagtg ctgcaatgat accgcgagac ccacgctcac   3840
cggctccaga tttatcagca ataaaccagc cagccggaag ggccgagcgc agaagtggtc   3900
ctgcaacttt atccgcctcc atccagtcta ttaattgttg ccgggaagct agagtaagta   3960
gttcgccagt taatagtttg cgcaacgttg ttgccattgc tacaggcatc gtggtgtcac   4020
gctcgtcgtt tggtatggct tcattcagct ccggttccca acgatcaagg cgagttacat   4080
gatcccccat gttgtgcaaa aaagcggtta gctccttcgg tcctccgatc gttgtcagaa   4140
gtaagttggc cgcagtgtta tcactcatgg ttatggcagc actgcataat tctcttactg   4200
tcatgccatc cgtaagatgc ttttctgtga ctggtgagta ctcaaccaag tcattctgag   4260
aatagtgtat gcggcgaccg agttgctctt gcccggcgtc aatacgggat aataccgcgc   4320
cacatagcag aactttaaaa gtgctcatca ttggaaaacg ttcttcgggg cgaaaactct   4380
```

-continued caaggatctt accgctgttg agatccagtt cgatgtaacc cactcgtgca cccaactgat 4440
cttcagcatc ttttactttc accagcgttt ctgggtgagc aaaaacagga aggcaaaatg 4500
ccgcaaaaaa gggaataagg gcgacacgga aatgttgaat actcatactc ttcctttttc 4560
aatattattg aagcatttat cagggttatt gtctcatgag cggatacata tttgaatgta 4620
tttagaaaaa taaacaaata ggggttccgc gcacatttcc ccgaaaagtg ccacctgacg 4680
tctaagaaac cattattatc atgacattaa cctataaaaa taggcgtatc acgaggccct 4740
ttcgtcttca c 4751

<210> SEQ ID NO 8
<211> LENGTH: 75
<212> TYPE: DNA
<213> ORGANISM: Artificial
<220> FEATURE:
<223> OTHER INFORMATION: "p13HTF" primer for PCR

<400> SEQUENCE: 8
atggtggtgg gactggaagt acaggttttc gttgttgttc gagctcgaat tagtctgcgc 60
gtctttcagg gcttc 75

<210> SEQ ID NO 9
<211> LENGTH: 6646
<212> TYPE: DNA
<213> ORGANISM: Artificial
<220> FEATURE:
<223> OTHER INFORMATION: pMAL-C2 expression plasmid

<400> SEQUENCE: 9
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg tgagttagct cactcattag 1200
gcacaattct catgtttgac agcttatcat cgactgcacg gtgcaccaat gcttctggcg 1260

-continued

```
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagattatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acggggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccacc atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctcta gagtcgacct gcaggcaagc ttggcactgg ccgtcgtttt acaacgtcgt   2760
gactgggaaa accctggcgt tacccaactt aatcgccttg cagcacatcc ccctttcgcc   2820
agctggcgta atagcgaaga ggcccgcacc gatcgccctt cccaacagtt gcgcagcctg   2880
aatggcgaat ggcagcttgg ctgttttggc ggatgagata agattttcag cctgatacag   2940
attaaatcag aacgcagaag cggtctgata aaacagaatt tgcctggcgg cagtagcgcg   3000
gtggtcccac ctgaccccat gccgaactca gaagtgaaac gccgtagcgc cgatggtagt   3060
gtggggtctc cccatgcgag agtagggaac tgccaggcat caaataaaac gaaaggctca   3120
gtcgaaagac tgggcctttc gttttatctg ttgtttgtcg gtgaacgctc tcctgagtag   3180
gacaaatccg ccgggagcgg atttgaacgt tgcgaagcaa cggcccggag ggtggcgggc   3240
aggacgcccg ccataaactg ccaggcatca aattaagcag aaggccatcc tgacggatgg   3300
cctttttgcg tttctacaaa ctctttttgt ttatttttct aaatacattc aaatatgtat   3360
ccgctcatga gacaataacc ctgataaatg cttcaataat attgaaaaag gaagagtatg   3420
agtattcaac atttccgtgt cgcccttatt cccttttttg cggcattttg ccttcctgtt   3480
tttgctcacc cagaaacgct ggtgaaagta aaagatgctg aagatcagtt gggtgcacga   3540
gtgggttaca tcgaactgga tctcaacagc ggtaagatcc ttgagagttt tcgccccgaa   3600
```

-continued

```
gaacgttctc caatgatgag cacttttaaa gttctgctat gtggcgcggt attatcccgt   3660
gttgacgccg ggcaagagca actcggtcgc cgcatacact attctcagaa tgacttggtt   3720
gagtactcac cagtcacaga aaagcatctt acggatggca tgacagtaag agaattatgc   3780
agtgctgcca taaccatgag tgataacact gcggccaact tacttctgac aacgatcgga   3840
ggaccgaagg agctaaccgc ttttttgcac aacatggggg atcatgtaac tcgccttgat   3900
cgttgggaac cggagctgaa tgaagccata ccaaacgacg agcgtgacac cacgatgcct   3960
gtagcaatgg caacaacgtt gcgcaaacta ttaactggcg aactacttac tctagcttcc   4020
cggcaacaat taatagactg gatggaggcg gataaagttg caggaccact tctgcgctcg   4080
gcccttccgg ctggctggtt tattgctgat aaatctggag ccggtgagcg tgggtctcgc   4140
ggtatcattg cagcactggg gccagatggt aagccctccc gtatcgtagt tatctacacg   4200
acggggagtc aggcaactat ggatgaacga aatagacaga tcgctgagat aggtgcctca   4260
ctgattaagc attggtaact gtcagaccaa gtttactcat atatacttta gattgattta   4320
ccccggttga taatcagaaa agccccaaaa acaggaagat tgtataagca aatatttaaa   4380
ttgtaaacgt taatattttg ttaaaattcg cgttaaattt ttgttaaatc agctcatttt   4440
ttaaccaata ggccgaaatc ggcaaaatcc cttataaatc aaaagaatag cccgagatag   4500
ggttgagtgt tgttccagtt tggaacaaga gtccactatt aaagaacgtg gactccaacg   4560
tcaaagggcg aaaaaccgtc tatcagggcg atggcccact acgtgaacca tcacccaaat   4620
caagtttttt ggggtcgagg tgccgtaaag cactaaatcg gaaccctaaa gggagccccc   4680
gatttagagc ttgacgggga aagccggcga acgtggcgag aaaggaaggg aagaaagcga   4740
aaggagcggg cgctagggcg ctggcaagtg tagcggtcac gctgcgcgta accaccacac   4800
ccgccgcgct taatgcgccg ctacagggcg cgtaaaagga tctaggtgaa gatccttttt   4860
gataatctca tgaccaaaat cccttaacgt gagttttcgt tccactgagc gtcagacccc   4920
gtagaaaaga tcaaaggatc ttcttgagat cctttttttc tgcgcgtaat ctgctgcttg   4980
caaacaaaaa aaccaccgct accagcggtg gtttgtttgc cggatcaaga gctaccaact   5040
ctttttccga aggtaactgg cttcagcaga gcgcagatac caaatactgt ccttctagtg   5100
tagccgtagt taggccacca cttcaagaac tctgtagcac cgcctacata cctcgctctg   5160
ctaatcctgt taccagtggc tgctgccagt ggcgataagt cgtgtcttac cgggttggac   5220
tcaagacgat agttaccgga taaggcgcag cggtcgggct gaacgggggg ttcgtgcaca   5280
cagcccagct tggagcgaac gacctacacc gaactgagat acctacagcg tgagctatga   5340
gaaagcgcca cgcttcccga agggagaaag gcggacaggt atccggtaag cggcagggtc   5400
ggaacaggag agcgcacgag ggagcttcca gggggaaacg cctggtatct ttatagtcct   5460
gtcgggtttc gccacctctg acttgagcgt cgatttttgt gatgctcgtc aggggggcgg   5520
agcctatgga aaaacgccag caacgcggcc tttttacggt tcctggcctt ttgctggcct   5580
tttgctcaca tgttctttcc tgcgttatcc cctgattctg tggataaccg tattaccgcc   5640
tttgagtgag ctgataccgc tcgccgcagc cgaacgaccg agcgcagcga gtcagtgagc   5700
gaggaagcgg aagagcgcct gatgcggtat tttctcctta cgcatctgtg cggtatttca   5760
caccgcatat ggtgcactct cagtacaatc tgctctgatg ccgcatagtt aagccagtat   5820
acactccgct atcgctacgt gactgggtca tggctgcgcc ccgacacccg ccaacacccg   5880
ctgacgcgcc ctgacgggct tgtctgctcc cggcatccgc ttacagacaa gctgtgaccg   5940
tctccgggag ctgcatgtgt cagaggtttt caccgtcatc accgaaacgc gcgaggcagc   6000
```

-continued

```
tgcggtaaag ctcatcagcg tggtcgtgca gcgattcaca gatgtctgcc tgttcatccg    6060

cgtccagctc gttgagtttc tccagaagcg ttaatgtctg gcttctgata aagcgggcca    6120

tgttaagggc ggttttttcc tgtttggtca cttgatgcct ccgtgtaagg gggaatttct    6180

gttcatgggg gtaatgatac cgatgaaacg agagaggatg ctcacgatac gggttactga    6240

tgatgaacat gcccggttac tggaacgttg tgagggtaaa caactggcgg tatggatgcg    6300

gcgggaccag agaaaaatca ctcagggtca atgccagcgc ttcgttaata cagatgtagg    6360

tgttccacag ggtagccagc agcatcctgc gatgcagatc cggaacataa tggtgcaggg    6420

cgctgacttc cgcgtttcca gactttacga aacacggaaa ccgaagacca ttcatgttgt    6480

tgctcaggtc gcagacgttt tgcagcagca gtcgcttcac gttcgctcgc gtatcggtga    6540

ttcattctgc taaccagtaa ggcaaccccg ccagcctagc cgggtcctca acgacaggag    6600

cacgatcatg cgcacccgtg gccaggaccc aacgctgccc gaaatt                   6646

<210> SEQ ID NO 10
<211> LENGTH: 42
<212> TYPE: DNA
<213> ORGANISM: Artificial
<220> FEATURE:
<223> OTHER INFORMATION: "21-F 5' internal" PCR primer

<400> SEQUENCE: 10

aacctgtact tccagaaaat cgaagaaggt aaactggtaa tc                        42

<210> SEQ ID NO 11
<211> LENGTH: 49
<212> TYPE: DNA
<213> ORGANISM: Artificial
<220> FEATURE:
<223> OTHER INFORMATION: "21-F 5' external" PCR primer

<400> SEQUENCE: 11

cgggacaagt ttgtacaaaa aagcaggctc cgaaaacctg tacttccag                 49

<210> SEQ ID NO 12
<211> LENGTH: 42
<212> TYPE: DNA
<213> ORGANISM: Artificial
<220> FEATURE:
<223> OTHER INFORMATION: "22-F 5' internal" PCR primer

<400> SEQUENCE: 12

ttcctcggca tggtcaaaat cgaagaaggt aaactggtaa tc                        42

<210> SEQ ID NO 13
<211> LENGTH: 52
<212> TYPE: DNA
<213> ORGANISM: Artificial
<220> FEATURE:
<223> OTHER INFORMATION: "22-F 5' external" PCR primer

<400> SEQUENCE: 13

cgggacaagt ttgtacaaaa aagcaggctc ccgctccttc ctcggcatgg tc             52

<210> SEQ ID NO 14
<211> LENGTH: 42
<212> TYPE: DNA
<213> ORGANISM: Artificial
<220> FEATURE:
<223> OTHER INFORMATION: "23-F 5' internal" PCR primer
```

-continued

<400> SEQUENCE: 14
gatgacgatg acaagaaaat cgaagaaggt aaactggtaa tc 42

<210> SEQ ID NO 15
<211> LENGTH: 49
<212> TYPE: DNA
<213> ORGANISM: Artificial
<220> FEATURE:
<223> OTHER INFORMATION: “23-F 5' external” PCR primer

<400> SEQUENCE: 15
cgggacaagt ttgtacaaaa aagcaggctc cgaagatgac gatgacaag 49

<210> SEQ ID NO 16
<211> LENGTH: 39
<212> TYPE: DNA
<213> ORGANISM: Artificial
<220> FEATURE:
<223> OTHER INFORMATION: “24-F 5' internal” PCR primer

<400> SEQUENCE: 16
atcgaaggac gcaaaatcga agaaggtaaa ctggtaatc 39

<210> SEQ ID NO 17
<211> LENGTH: 43
<212> TYPE: DNA
<213> ORGANISM: Artificial
<220> FEATURE:
<223> OTHER INFORMATION: “24-F 5' external” PCR primer

<400> SEQUENCE: 17
cgggacaagt ttgtacaaaa aagcaggctc catcgaagga cgc 43

<210> SEQ ID NO 18
<211> LENGTH: 42
<212> TYPE: DNA
<213> ORGANISM: Artificial
<220> FEATURE:
<223> OTHER INFORMATION: “25-F 5' internal” PCR primer

<400> SEQUENCE: 18
gtaccacgtg gcagtaaaat cgaagaaggt aaactggtaa tc 42

<210> SEQ ID NO 19
<211> LENGTH: 49
<212> TYPE: DNA
<213> ORGANISM: Artificial
<220> FEATURE:
<223> OTHER INFORMATION: “25-F 5' external” PCR primer

<400> SEQUENCE: 19
cgggacaagt ttgtacaaaa aagcaggctc cctagtacca cgtggcagt 49

<210> SEQ ID NO 20
<211> LENGTH: 45
<212> TYPE: DNA
<213> ORGANISM: Artificial
<220> FEATURE:
<223> OTHER INFORMATION: “26-F 5' internal” PCR primer

<400> SEQUENCE: 20
aacctgtact tccagtccaa aatcgaagaa ggtaaactgg taatc 45

<210> SEQ ID NO 21
<211> LENGTH: 49

-continued

<212> TYPE: DNA
<213> ORGANISM: Artificial
<220> FEATURE:
<223> OTHER INFORMATION: “26-F 5' external” PCR primer

<400> SEQUENCE: 21
cgggacaagt ttgtacaaaa aagcaggctc cgaaaacctg tacttccag 49

<210> SEQ ID NO 22
<211> LENGTH: 27
<212> TYPE: DNA
<213> ORGANISM: Artificial
<220> FEATURE:
<223> OTHER INFORMATION: Maltose binding protein-encoding domain

<400> SEQUENCE: 22
aaaatcgaag aaggtaaact ggtaatc 27

<210> SEQ ID NO 23
<211> LENGTH: 31
<212> TYPE: DNA
<213> ORGANISM: Artificial
<220> FEATURE:
<223> OTHER INFORMATION: GW-encoding domain

<400> SEQUENCE: 23
cgggacaagt ttgtacaaaa aagcaggctc c 31

<210> SEQ ID NO 24
<211> LENGTH: 35
<212> TYPE: PRT
<213> ORGANISM: Artificial
<220> FEATURE:
<223> OTHER INFORMATION: “21-F” artificial protease substrate

<400> SEQUENCE: 24

```
Met Ser Tyr Tyr His His His His His His Leu Glu Ser Cys Cys Pro
1               5                   10                  15

Gly Cys Cys Thr Ser Leu Tyr Lys Lys Ala Gly Ser Glu Asn Leu Tyr
            20                  25                  30

Phe Lys Ser
        35
```

<210> SEQ ID NO 25
<211> LENGTH: 35
<212> TYPE: PRT
<213> ORGANISM: Artificial
<220> FEATURE:
<223> OTHER INFORMATION: “22-F” artificial protease substrate

<400> SEQUENCE: 25

```
Met Ser Tyr Tyr His His His His His His Leu Glu Ser Cys Cys Pro
1               5                   10                  15

Gly Cys Cys Thr Ser Leu Tyr Lys Lys Ala Gly Ser Arg Ser Phe Leu
            20                  25                  30

Gly Met Val
        35
```

<210> SEQ ID NO 26
<211> LENGTH: 34
<212> TYPE: PRT
<213> ORGANISM: Artificial
<220> FEATURE:
<223> OTHER INFORMATION: “23-F” artificial protease substrate -continued

```
<400> SEQUENCE: 26

Met Ser Tyr Tyr His His His His His His Leu Glu Ser Cys Cys Pro
1               5                   10                  15

Gly Cys Cys Thr Ser Leu Tyr Lys Lys Ala Gly Ser Glu Asp Asp Asp
            20                  25                  30
Asp Lys


<210> SEQ ID NO 27
<211> LENGTH: 32
<212> TYPE: PRT
<213> ORGANISM: Artificial
<220> FEATURE:
<223> OTHER INFORMATION: "24-F" artificial protease substrate

<400> SEQUENCE: 27

Met Ser Tyr Tyr His His His His His His Leu Glu Ser Cys Cys Pro
1               5                   10                  15

Gly Cys Cys Thr Ser Leu Tyr Lys Lys Ala Gly Ser Ile Glu Gly Arg
            20                  25                  30


<210> SEQ ID NO 28
<211> LENGTH: 34
<212> TYPE: PRT
<213> ORGANISM: Artificial
<220> FEATURE:
<223> OTHER INFORMATION: "25-F" artificial protease substrate

<400> SEQUENCE: 28

Met Ser Tyr Tyr His His His His His His Leu Glu Ser Cys Cys Pro
1               5                   10                  15

Gly Cys Cys Thr Ser Leu Tyr Lys Lys Ala Gly Ser Leu Val Pro Arg
            20                  25                  30

Gly Ser


<210> SEQ ID NO 29
<211> LENGTH: 35
<212> TYPE: PRT
<213> ORGANISM: Artificial
<220> FEATURE:
<223> OTHER INFORMATION: "26-F" artificial protease substrate

<400> SEQUENCE: 29

Met Ser Tyr Tyr His His His His His His Leu Glu Ser Cys Cys Pro
1               5                   10                  15

Gly Cys Cys Thr Ser Leu Tyr Lys Lys Ala Gly Ser Glu Asn Leu Tyr
            20                  25                  30

Phe Gln Ser
        35


<210> SEQ ID NO 30
<211> LENGTH: 10
<212> TYPE: PRT
<213> ORGANISM: Artificial
<220> FEATURE:
<223> OTHER INFORMATION: First ten (10) residues of the N-terminal
      sequence of MBP

<400> SEQUENCE: 30

Lys Ile Glu Glu Gly Lys Leu Val Ile Trp
1               5                   10


<210> SEQ ID NO 31
<211> LENGTH: 4762
```

-continued

<212> TYPE: DNA
<213> ORGANISM: Artificial
<220> FEATURE:
<223> OTHER INFORMATION: pDONR-221 cloning plasmid

<400> SEQUENCE: 31

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacacattg atgagcaatg cttttttata atgccaactt tgtacaaaaa    660
agctgaacga gaaacgtaaa atgatataaa tatcaatata ttaaattaga ttttgcataa    720
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc ttttttgtgt gacaaaataa aaacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta taagggagcc tgacatttat   1200
attccccaga acatcaggtt aatggcgttt ttgatgtcat tttcgcggtg gctgagatca   1260
gccacttctt ccccgataac ggagaccggc acactggcca tatcggtggt catcatgcgc   1320
cagctttcat ccccgatatg caccaccggg taaagttcac gggagacttt atctgacagc   1380
agacgtgcac tggccagggg gatcaccatc cgtcgcccgg gcgtgtcaat aatatcactc   1440
tgtacatcca caaacagacg ataacggctc tctcttttat aggtgtaaac cttaaactgc   1500
atttcaccag cccctgttct cgtcagcaaa agagccgttc atttcaataa accgggcgac   1560
ctcagccatc ccttcctgat ttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctcttttg    1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
```

-continued

```
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg tttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaaaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa aacagcattc caggtattag   3480
aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tatttttgac gaggggaaat   3780
taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
atggtattga taatcctgat atgaataaat tgcagtttca tttgatgctc gatgagtttt   3960
tctaatcaga attggttaat tggttgtaac actggcagag cattacgctg acttgacggg   4020
acggcgcaag ctcatgacca aaatccctta acgtgagtta cgcgtcgttc cactgagcgt   4080
cagaccccgt agaaaagatc aaaggatctt cttgagatcc tttttttctg cgcgtaatct   4140
gctgcttgca aacaaaaaaa ccaccgctac cagcggtggt ttgtttgccg gatcaagagc   4200
taccaactct ttttccgaag gtaactggct tcagcagagc gcagatacca aatactgttc   4260
ttctagtgta gccgtagtta ggccaccact tcaagaactc tgtagcaccg cctacatacc   4320
tcgctctgct aatcctgtta ccagtggctg ctgccagtgg cgataagtcg tgtcttaccg   4380
ggttggactc aagacgatag ttaccggata aggcgcagcg gtcgggctga acggggggtt   4440
cgtgcacaca gcccagcttg gagcgaacga cctacaccga actgagatac ctacagcgtg   4500
agctatgaga aagcgccacg cttcccgaag ggagaaaggc ggacaggtat ccggtaagcg   4560
```

-continued gcagggtcgg aacaggagag cgcacgaggg agcttccagg gggaaacgcc tggtatcttt 4620
atagtcctgt cgggtttcgc cacctctgac ttgagcgtcg atttttgtga tgctcgtcag 4680
gggggcggag cctatggaaa aacgccagca acgcggcctt tttacggttc ctggcctttt 4740
gctggccttt tgctcacatg tt 4762

<210> SEQ ID NO 32
<211> LENGTH: 49
<212> TYPE: DNA
<213> ORGANISM: Artificial
<220> FEATURE:
<223> OTHER INFORMATION: 5' external PCR primer shown in Fig. 15

<400> SEQUENCE: 32
ggggacaagt ttgtacaaaa aagcaggctc cgaaaacctg tacttccag 49

<210> SEQ ID NO 33
<211> LENGTH: 45
<212> TYPE: DNA
<213> ORGANISM: Artificial
<220> FEATURE:
<223> OTHER INFORMATION: 5' internal PCR primer shown in Fig. 15

<400> SEQUENCE: 33
aacctgtact tccagtccaa aatcgaagaa ggtaaactgg taatc 45

<210> SEQ ID NO 34
<211> LENGTH: 33
<212> TYPE: DNA
<213> ORGANISM: Artificial
<220> FEATURE:
<223> OTHER INFORMATION: 5' end of E. coli MBP target gene as shown in Fig. 15

<400> SEQUENCE: 34
aaaatcgaag aaggtaaact ggtaatctgg att 33

<210> SEQ ID NO 35
<211> LENGTH: 30
<212> TYPE: DNA
<213> ORGANISM: Artificial
<220> FEATURE:
<223> OTHER INFORMATION: 3' external PCR primer as shown in Fig. 15

<400> SEQUENCE: 35
ggggaccact ttgtacaaga aagctgggtc 30

<210> SEQ ID NO 36
<211> LENGTH: 42
<212> TYPE: DNA
<213> ORGANISM: Artificial
<220> FEATURE:
<223> OTHER INFORMATION: 3' internal PCR primer as shown in Fig. 15

<400> SEQUENCE: 36
gtacaagaaa gctgggtcct aagtctgcgc gtctttcagg gc 42

<210> SEQ ID NO 37
<211> LENGTH: 26
<212> TYPE: DNA
<213> ORGANISM: Artificial
<220> FEATURE:
<223> OTHER INFORMATION: 3' end of target gene as shown in Fig. 15

<400> SEQUENCE: 37

-continued gtctgcgcgt ctttcagggc ttcatc 26

<210> SEQ ID NO 38
<211> LENGTH: 6520
<212> TYPE: DNA
<213> ORGANISM: Artificial
<220> FEATURE:
<223> OTHER INFORMATION: “pVP-X4” expression plasmid
<220> FEATURE:
<221> NAME/KEY: gene
<222> LOCATION: (1)..(829)
<223> OTHER INFORMATION: beta-lactamase gene (provides ampicillin resistance)
<220> FEATURE:
<221> NAME/KEY: misc_feature
<222> LOCATION: (1149)..(1151)
<223> OTHER INFORMATION: start codon
<220> FEATURE:
<221> NAME/KEY: misc_feature
<222> LOCATION: (1155)..(1178)
<223> OTHER INFORMATION: poly-histidine tag (His8)
<220> FEATURE:
<221> NAME/KEY: misc_feature
<222> LOCATION: (1179)..(1196)
<223> OTHER INFORMATION: Cloning site for solubility domain insertion, including NsiI and PacI sites
<220> FEATURE:
<221> NAME/KEY: misc_feature
<222> LOCATION: (1197)..(1220)
<223> OTHER INFORMATION: HRV 14 3C protease recognition sequence
<220> FEATURE:
<221> NAME/KEY: misc_feature
<222> LOCATION: (1221)..(1238)
<223> OTHER INFORMATION: tetra-cysteine motif
<220> FEATURE:
<221> NAME/KEY: misc_feature
<222> LOCATION: (1239)..()
<223> OTHER INFORMATION: Start of att R1 recombination site
<220> FEATURE:
<221> NAME/KEY: gene
<222> LOCATION: (4052)..(5136)
<223> OTHER INFORMATION: Lac I gene
<220> FEATURE:
<221> NAME/KEY: misc_feature
<222> LOCATION: (5331)..()
<223> OTHER INFORMATION: ColE1 replicon
<220> FEATURE:
<221> NAME/KEY: gene
<222> LOCATION: (6489)..(6520)
<223> OTHER INFORMATION: beta-lactamase gene

<400> SEQUENCE: 38
cagcgatctg tctatttcgt tcatccatag ttgcctgact ccccgtcgtg tagataacta 60
cgatacggga gggcttacca tctggcccca gtgctgcaat gataccgcga gacccacgct 120
caccggctcc agatttatca gcaataaacc agccagccgg aagggccgag cgcagaagtg 180
gtcctgcaac tttatccgcc tccatccagt ctattaattg ttgccgggaa gctagagtaa 240
gtagttcgcc agttaatagt ttgcgcaacg ttgttgccat tgctacaggc atcgtggtgt 300
cacgctcgtc gtttggtatg gcttcattca gctccggttc ccaacgatca aggcgagtta 360
catgatcccc catgttgtgc aaaaaagcgg ttagctcctt cggtcctccg atcgttgtca 420
gaagtaagtt ggccgcagtg ttatcactca tggttatggc agcactgcat aattctctta 480
ctgtcatgcc atccgtaaga tgcttttctg tgactggtga gtactcaacc aagtcattct 540
gagaatagtg tatgcggcga ccgagttgct cttgcccggc gtcaatacgg gataataccg 600
cgccacatag cagaacttta aaagtgctca tcattggaaa acgttcttcg gggcgaaaac 660
tctcaaggat cttaccgctg ttgagatcca gttcgatgta acccactcgt gcacccaact 720

-continued

```
gatcttcagc atcttttact ttcaccagcg tttctgggtg agcaaaaaca ggaaggcaaa    780

atgccgcaaa aaagggaata agggcgacac ggaaatgttg aatactcata ctcttccttt    840

ttcaatatta ttgaagcatt tatcagggtt attgtctcat gagcggatac atatttgaat    900

gtatttagaa aaataaacaa ataggggttc cgcgcacatt tccccgaaaa gtgccacctg    960

acgtctaaga aaccattatt atcatgacat taacctataa aaataggcgt atcacgaggc   1020

cctttcgtct tcacctcgag aaatcataaa aaatttattt gctttgtgag cggataacaa   1080

ttataataga ttcaattgtg agcggataac aatttcacac agaattcatt aaagaggaga   1140

aattaaccat gggacatcac catcatcacc atcaccatgc atcggcctta attaacctgg   1200

aagttctgtt ccaggggccc tgttgcccag gttgctgtac aagtttgtac aaaaaagctg   1260

aacgagaaac gtaaaatgat ataaatatca atatattaaa ttagattttg cataaaaaac   1320

agactacata atactgtaaa acacaacata tccagtcact atggcggccg cattaggcac   1380

cccaggcttt acactttatg ctttcggctc gtataatgtg tggattttga gttaggatcc   1440

gtcgagattt tcaggagcta aggaagctaa aatggagaaa aaaatcactg gatataccac   1500

cgttgatata tcccaatggc atcgtaaaga acattttgag gcatttcagt cagttgctca   1560

atgtacctat aaccagaccg ttcagctgga tattacggcc tttttaaaga ccgtaaagaa   1620

aaataagcac aagttttatc cggcctttat tcacattctt gcccgcctga tgaatgctca   1680

tccggaattc cgtatggcaa tgaaagacgg tgagctggtg atatgggata gtgttcaccc   1740

ttgttacacc gttttccatg agcaaactga aacgttttca tcgctctgga gtgaatacca   1800

cgacgatttc cggcagtttc tacacatata ttcgcaagat gtggcgtgtt acggtgaaaa   1860

cctggcctat ttccctaaag ggtttattga gaatatgttt ttcgtctcag ccaatccctg   1920

ggtgagtttc accagttttg atttaaacgt ggccaatatg gacaacttct tcgcccccgt   1980

tttcaccatg ggcaaatatt atacgcaagg cgacaaggtg ctgatgccgc tggcgattca   2040

ggttcatcat gccgtttgtg atggcttcca tgtcggcaga atgcttaatg aattacaaca   2100

gtactgcgat gagtggcagg gcggggcgta aagatctgga tccggcttac taaaagccag   2160

ataacagtat gcgtatttgc gcgctgattt ttgcggtata agaatatata ctgatatgta   2220

tacccgaagt atgtcaaaaa gaggtatgct atgaagcagc gtattacagt gacagttgac   2280

agcgacagct atcagttgct caaggcatat atgatgtcaa tatctccggt ctggtaagca   2340

caaccatgca gaatgaagcc cgtcgtctgc gtgccgaacg ctggaaagcg gaaaatcagg   2400

aagggatggc tgaggtcgcc cggtttattg aaatgaacgg ctcttttgct gacgagaaca   2460

ggggctggtg aaatgcagtt taaggtttac acctataaaa gagagagccg ttatcgtctg   2520

tttgtggatg tacagagtga tattattgac acgcccgggc gacggatggt gatccccctg   2580

gccagtgcac gtctgctgtc agataaagtc tcccgtgaac tttacccggt ggtgcatatc   2640

ggggatgaaa gctggcgcat gatgaccacc gatatggcca gtgtgccggt ctccgttatc   2700

ggggaagaag tggctgatct cagccaccgc gaaaatgaca tcaaaaacgc cattaacctg   2760

atgttctggg gaatataaat gtcaggctcc cttatacaca gccagtctgc aggtcgacca   2820

tagtgactgg atatgttgtg ttttacagta ttatgtagtc tgttttttat gcaaaatcta   2880

atttaatata ttgatattta tatcatttta cgtttctcgt tcagctttct tgtacaaagt   2940

ggtgatggcg cgcctgtagg acgtcgacgg taccatcgat acgcgttcga agcttaatta   3000

gctgagcttg gactcctgtt gatagatcca gtaatgacct cagaactcca tctggatttg   3060

ttcagaacgc tcggttgccg ccgggcgttt tttattggtg agaatccaag ctagcttggc   3120
```

-continued

```
gagattttca ggagctaagg aagctaaaat ggagaaaaaa atcactggat ataccaccgt   3180
tgatatatcc caatggcatc gtaaagaaca ttttgaggca tttcagtcag ttgctcaatg   3240
tacctataac cagaccgttc agctggatat tacggccttt ttaaagaccg taaagaaaaa   3300
taagcacaag ttttatccgg cctttattca cattcttgcc cgcctgatga atgctcatcc   3360
ggaatttcgt atggcaatga aagacggtga gctggtgata tgggatagtg ttcacccttg   3420
ttacaccgtt ttccatgagc aaactgaaac gttttcatcg ctctggagtg aataccacga   3480
cgatttccgg cagtttctac acatatattc gcaagatgtg gcgtgttacg gtgaaaacct   3540
ggcctatttc cctaaagggt ttattgagaa tatgtttttc gtctcagcca atccctgggt   3600
gagtttcacc agttttgatt taaacgtggc caatatggac aacttcttcg cccccgtttt   3660
caccatgggc aaatattata cgcaaggcga caaggtgctg atgccgctgg cgattcaggt   3720
tcatcatgcc gtttgtgatg gcttccatgt cggcagaatg cttaatgaat tacaacagta   3780
ctgcgatgag tggcagggcg gggcgtaatt tttttaaggc agttattggt gcccttaaac   3840
gcctggggta atgactctct agcttgaggc atcaaataaa acgaaaggct cagtcgaaag   3900
actgggcctt tcgttttatc tgttgtttgt cggtgaacgc tctcctgagt aggacaaatc   3960
cgccctctag attacgtgca gtcgatgata agctgtcaaa catgagaatt gtgcctaatg   4020
agtgagctaa cttacattaa ttgcgttgcg ctcactgccc gctttccagt cgggaaacct   4080
gtcgtgccag ctgcattaat gaatcggcca acgcgcgggg agaggcggtt tgcgtattgg   4140
gcgccagggt ggtttttctt ttcaccagtg agacgggcaa cagctgattg cccttcaccg   4200
cctggccctg agagagttgc agcaagcggt ccacgctggt ttgccccagc aggcgaaaat   4260
cctgtttgat ggtggttaac ggcgggatat aacatgagct gtcttcggta tcgtcgtatc   4320
ccactaccga gatatccgca ccaacgcgca gcccggactc ggtaatggcg cgcattgcgc   4380
ccagcgccat ctgatcgttg gcaaccagca tcgcagtggg aacgatgccc tcattcagca   4440
tttgcatggt ttgttgaaaa ccggacatgg cactccagtc gccttcccgt tccgctatcg   4500
gctgaatttg attgcgagtg agatatttat gccagccagc cagacgcaga cgcgccgaga   4560
cagaacttaa tgggcccgct aacagcgcga tttgctggtg acccaatgcg accagatgct   4620
ccacgcccag tcgcgtaccg tcttcatggg agaaaataat actgttgatg ggtgtctggt   4680
cagagacatc aagaaataac gccggaacat tagtgcaggc agcttccaca gcaatggcat   4740
cctggtcatc cagcggatag ttaatgatca gcccactgac gcgttgcgcg agaagattgt   4800
gcaccgccgc tttacaggct tcgacgccgc ttcgttctac catcgacacc accacgctgg   4860
cacccagttg atcggcgcga gatttaatcg ccgcgacaat ttgcgacggc gcgtgcaggg   4920
ccagactgga ggtggcaacg ccaatcagca acgactgttt gcccgccagt tgttgtgcca   4980
cgcggttggg aatgtaattc agctccgcca tcgccgcttc cactttttcc cgcgttttcg   5040
cagaaacgtg gctggcctgg ttcaccacgc gggaaacggt ctgataagag acaccggcat   5100
actctgcgac atcgtataac gttactggtt tcacattcac caccctgaat tgactctctt   5160
ccgggcgcta tcatgccata ccgcgaaagg ttttgcacca ttcgatggtg tcggaatttc   5220
gggcagcgtt gggtcctggc cacgggtgcg catgatctag agctgcctcg cgcgtttcgg   5280
tgatgacggt gaaaacctct gacacatgca gctcccggag acggtcacag cttgtctgta   5340
agcggatgcc gggagcagac aagcccgtca gggcgcgtca gcgggtgttg gcgggtgtcg   5400
gggcgcagcc atgacccagt cacgtagcga tagcggagtg tatactggct taactatgcg   5460
```

-continued

```
gcatcagagc agattgtact gagagtgcac catatgcggt gtgaaatacc gcacagatgc   5520

gtaaggagaa aataccgcat caggcgctct tccgcttcct cgctcactga ctcgctgcgc   5580

tcggtcgttc ggctgcggcg agcggtatca gctcactcaa aggcggtaat acggttatcc   5640

acagaatcag gggataacgc aggaaagaac atgtgagcaa aaggccagca aaaggccagg   5700

aaccgtaaaa aggccgcgtt gctggcgttt ttccataggc tccgcccccc tgacgagcat   5760

cacaaaaatc gacgctcaag tcagaggtgg cgaaacccga caggactata aagataccag   5820

gcgtttcccc ctggaagctc cctcgtgcgc tctcctgttc cgaccctgcc gcttaccgga   5880

tacctgtccg cctttctccc ttcgggaagc gtggcgcttt ctcatagctc acgctgtagg   5940

tatctcagtt cggtgtaggt cgttcgctcc aagctgggct gtgtgcacga accccccgtt   6000

cagcccgacc gctgcgcctt atccggtaac tatcgtcttg agtccaaccc ggtaagacac   6060

gacttatcgc cactggcagc agccactggt aacaggatta gcagagcgag gtatgtaggc   6120

ggtgctacag agttcttgaa gtggtggcct aactacggct acactagaag gacagtattt   6180

ggtatctgcg ctctgctgaa gccagttacc ttcggaaaaa gagttggtag ctcttgatcc   6240

ggcaaacaaa ccaccgctgg tagcggtggt ttttttgttt gcaagcagca gattacgcgc   6300

agaaaaaaag gatctcaaga agatcctttg atcttttcta cggggtctga cgctcagtgg   6360

aacgaaaact cacgttaagg gattttggtc atgagattat caaaaaggat cttcacctag   6420

atccttttaa attaaaaatg aagttttaaa tcaatctaaa gtatatatga gtaaacttgg   6480

tctgacagtt accaatgctt aatcagtgag gcacctatct                         6520
```

FLUORESCENCE POLARIZATION ASSAY TO DETECT PROTEASE CLEAVAGE

CROSS-REFERENCE TO RELATED APPLICATIONS

Priority is hereby claimed to provisional application Ser. No. 60/607,210, filed Sep. 3, 2004, and to provisional application Ser. No. 60/524,812, filed Nov. 25, 2003, both of which are incorporated herein.

INCORPORATION BY REFERENCE

All of the documents referenced below are incorporated herein by reference.

FEDERAL FUNDING

This invention was made with United States government support awarded by the following agencies: NIH GMO64598. The United States has certain rights in this invention.

FIELD OF THE INVENTION

The present invention is directed to a method of elucidating protein interactions. More specifically, the invention is directed to a method of measuring the effectiveness of proteases, in real time, using fluorescence polarization spectroscopy.

BACKGROUND OF THE INVENTION

Proteomics is the large-scale study of proteins, particularly their structure and function. With the completion of the human genome project it has become clear that further inquiry into the interactions of proteins, both with other proteins and with nucleic acids, is necessary to understand how genomic data is processed. For example, the current understanding of the human genomic data gleaned to date suggests that there are approximately 33,000 coding regions in the human genome. However, approximately 200,000 different proteins have already been identified in humans. Determining how roughly 33,000 genes give rise to roughly 200,000 different proteins is a question central to proteomics.

Current methods to investigate protein functions are generally based on static analyses, rather than on dynamic observations. For example, technologies currently relied upon to investigate protein characteristics use mass spectroscopy, x-ray crystallography, nuclear magnetic resonance (NMR), and gel electrophoresis. By definition, these techniques investigate the structure of proteins based on static measurements such as size, charge, mass, magnetic moment, or a combination of those features. As a consequence, these analytical methods are not amenable to investigating peptides or proteins when their physical characteristics are in flux. Because protein interactions are dynamic and complex, these static approaches reveal only limited forms of data.

One feature of proteins that is inherently dynamic, their interactions with other molecules, is measured almost entirely via static methods. For example, ligand/receptor interactions are commonly visualized by their co-crystallization, which crystallizes the components at an arbitrarily fixed point in their interaction. Because the interaction of proteins involves changes in their mass, size, or charge, the process of protein-protein interaction is inferred from a comparison of the starting materials with the products. For example, the effectiveness of proteases on particular substrates is often inferred by incubating the putative protease with a putative substrate for some defined period of time. This is followed by subjecting the reaction mixture to SDS-PAGE gel separation to visualize the products. While this method of determining the effectiveness of a protease on a substrate is easily interpreted, it does not provide quantitative data, it is not continuous, and it is time consuming. Consequently, such methods are not amenable to high-throughput screening of protease activity specifically, or protein interactions generally.

Other methods of determining protease activity are equally limited. For example, enzyme-linked immunosorbent assays (ELISA) are flexible but are indirect, time-consuming, provide limited quantification, and are limited to discrete time points. Similarly, analytical methods that rely upon labeling free amino acid groups are limited to peptides. These methods are also time-consuming, and yield data that are limited to discrete time points. Other methods, such as measuring absorbance of light by a solution at 280 nm or measuring fluorescence intensity based on precipitation, are limited to non-specific proteases and are not continuous.

That being said, certain methods using fluorescence labeling allow for real-time monitoring of protein interactions. These known methods, however, suffer from other technological limitations. For example, conventional labeling of proteins with a fluorophore is not easily controlled. Multiple lysine or cysteine residues of the peptide being studied are usually labeled, thus resulting in potentially multiple fluorescent moieties being present in a single product. Consequently, the extent of fluorophore labeling becomes a variable that must be closely monitored and controlled. If the extent of labeling is uncontrolled or unknown, there will be multiple fluorescent moieties that will introduce unknown errors in the results (or might even confound the results entirely). Another known analytical method, fluorescence resonance energy transfer (FRET), requires extensive substrate optimization, is generally limited to peptides, and can also result in non-specific labeling. Thus, the fluorescence methods currently available require specific technical knowledge and specialized equipment for their optimal use. And, as in the other method discussed, the conventional fluorescent approaches are not well-suited for high-throughput screening.

While the conventional dynamic methods are cumbersome, fluorescence polarization yields valuable knowledge. Fluorescence polarization is based upon two physical phenomena. The first phenomenon is that a fluorescent molecule excited by plane-polarized energy emits energy in the same plane. The second phenomenon is that molecules in solution rotate naturally, with smaller molecules rotating more rapidly as compared to larger molecules. Because of these two phenomena, a correlation can be made between the size of a fluorescent molecule and the rate of change of its emitted, plane-polarized energy. Fluorescence polarization can be used to measure DNA-protein, protein-protein, and antigen-antibody interactions.

While the term "fluorescence polarization" is used herein, the term "fluorescence anisotropy" is often used synonymously to denote the same phenomena. Anisotropy is the characteristic of a medium wherein a given physical property differs in value in different directions within the medium. In the current instance, fluorescence anisotropy and fluorescence polarization are two different means to describe the same phenomenon. Anisotropy values and fluorescence values can be inter-converted using simple and well-known algebraic functions.

Recently a new method of fluorescently labeling a protein has been described by Griffin et al. (Science, 1998, 281:

269-272), Adams et al. (J. Am. Chem. Soc., 2002, 124: 6063-6076), and Tsien et al. (U.S. Pat. Nos. 5,932,474; 6,008,378; 6,054,271, and 6,451,569), all incorporated herein by reference. These documents describe biarsenical compounds and the specific target sequences to which they bind. An analytical method and corresponding kit utilizing these reagents is marketed under the trademark "FlAsH"-brand (Fluorescein Arsenical Hairpin binder) fluorescent labeling kit, and "ReAsH" (Resorufin Arsenical Hairpin binder), both by PanVera Corporation (Madison, Wis., now a wholly-owned subsidiary of Invitrogen Life Sciences, Carlsbad, Calif.). See Invitrogen Product Nos. P3050 for FlAsH, and P3006 for ReAsH, and product literature #L0920 Rev. 01/03).

This labeling method utilizes a reagent comprising a fluorescent ligand that is a biarsenical derivative of fluorescein and is weakly bound to a quenching moiety. The fluorescent ligand binds with greater affinity to a fluorescence tag, comprising a tetracysteine motif While neither the ligand nor the fluorescence tag is fluorescent alone, mixing them allows the fluorescence tag to displace the quenching moiety, thereby resulting in a highly fluorescent complex specifically bound to the tetracysteine motif. Because the motif is very rare in naturally occurring proteins, the fluorescence tag can be engineered into a protein with the expectation that the biarsenical ligand will bind specifically to the tetracysteine motif Currently, the FlAsH/ReAsH-branded systems are used for protein labeling investigations where the object is to follow a protein through in-vitro or in-vivo pathways.

As noted earlier, the progress to date of the human genome project indicates that the "one-gene, one protein" hypothesis will require considerable modification to account for the observed diversity of the proteome. The ability to use current techniques to further elucidate the role of proteins in their interactions and their role in developing protein diversity is extremely restricted by the limitations of current technology. Therefore, there is a long-felt and unmet need for a method to study protein interactions that allows for high-throughput screening of those interactions with a minimum of substrate optimization and product manipulation.

SUMMARY OF THE INVENTION

The present invention provides methods for elucidating protein interactions by the high-throughput screening of proteases and their potential substrates.

In a first embodiment, the invention provides a method of measuring protease activity comprising providing a protease substrate including a fluorescence tag, wherein the fluorescence tag comprises an amino acid motif Cys-Cys-Xaa-Xaa-Cys-Cys (SEQ. ID. NO: 1). Reagents encompassed within the motif shown in SEQ. ID. NO: 1 are referred to herein as tetracys reagents. The substrate is then contacted with a reagent capable of forming a fluorescent complex with the tetraCys amino acid motif, whereby a fluorescent complex is formed. The method then provides for contacting the fluorescent complex with a protease, under conditions wherein the protease is enzymatically active, to yield a mixture. The mixture can then be analyzed by measuring fluorescence polarization of the mixture whereby the activity of the protease is determined. It is preferred that the fluorescence polarization of the mixture be measured dynamically, and in real time.

In a second embodiment, the invention provides a method of measuring protease activity comprising providing a protease substrate including a fluorescence tag having an amino acid motif. The protease substrate is then contacted with a reagent capable of forming a fluorescent complex with the amino acid motif, thereby forming a fluorescent complex. The fluorescent complex is then contacted with a protease, under conditions wherein the protease is enzymatically active, to yield a mixture. The fluorescent polarization of the mixture is then measured, thereby determining the activity of the protease with the substrate.

In a third embodiment, the invention comprises a method of measuring protease activity including providing a protease substrate, wherein the protease substrate includes a fluorescence tag comprised of amino acid residues. The fluorescence tag is then reacted with a reagent in a mixture, wherein the reagent includes arsenic residues and wherein the residues of the reagent bind to residues of the tag. The binding of the reagent to the tag generates a fluorescent complex bound to the protease substrate. The fluorescent polarization of the complex is then determined, thereby providing a measure of the bound fluorescent complex. The fluorescent complex is then contacted with a protease under conditions wherein the protease is enzymatically active to yield a mixture, wherein the protease may cleave the fluorescent complex from the protease substrate. The amount of energy emitted from the fluorescent complex remaining bound to the protease substrate is then determined using fluorescent polarization.

In a fourth embodiment, the invention comprises a method of defining the potential of a given unknown target for proteolysis by a known enzyme. In this embodiment a known protease is directed against an unknown target. By studying the proteolysis of uncharacterized substrates by known proteases an understanding of the importance of the protease recognition sequence on the lability of the cut site can be investigated. These data provide information of the effect of sequences outside the nominal recognition sequence on the cut site itself, as well as the effects of temperature, pH, buffer components, etc. on the protease-catalyzed cleavage of the target. As described herein, the target is modified to include a fluorescence tag comprised of amino acid residues. The fluorescence tag is then reacted with a reagent in a mixture, wherein the reagent includes arsenic residues and wherein the residues of the reagent bind to residues of the tag. The binding of the reagent to the tag generates a fluorescent complex bound to the protease substrate. The target is then reacted with the known protease and the fluorescence polarization is measured over a period of time.

In a fifth embodiment, the invention comprises a vector for use in determining the activity of a protease. The vector comprises a DNA coding sequence for a fluorescence tag comprising a component of a fluorescent complex, a promoter region (preferably a viral promoter), and a DNA sequence coding for a target protein. Expression of the vector results in the production of a protease substrate that includes a fluorescence tag.

In a sixth embodiment, the invention comprises a kit for determining the activity of a protease. The kit comprising at least one vector as described in the immediately preceding paragraph. In the preferred embodiment of the kit, the vector comprises a coding region for a purification tag, a fluorescence tag, a promoter sequence, and a multiple cloning site for inserting a DNA coding region of a target protein.

The invention has many important applications. Proteases are important industrial products, and are used extensively in cleaning and decontamination formulations. In fact, proteases are particularly important in commodity products such as laundry detergent, where proteinaceous stains are most easily degraded by specific proteases. Proteases are also used as tools during protein production. In addition, proteases are involved in serious disease states. For example, proteases are produced by the HIV virus and by specific cancers. Proteases are also important diagnostic antigens. For instance, the prostate specific antigen (PSA), the level of which is used to diagnose the presence of prostate cancer, is a protease.

The present invention has multiple uses. It can be used to monitor protease activity in real time. The invention can also be used to investigate the effects of sequence variations or environmental conditions on the activity of proteases or protease substrates. In addition, the invention can be used to monitor cleavage efficiency in the production of fusion proteins. After the fusion protein is expressed, the fusion tags must be removed from the target protein to yield the final product. The present invention can be used to measure the efficiency and extent of cleavage of the target protein from its fusion partner.

Moreover, the present invention can be used to identify, isolate, characterize, and/or optimize improvements in the protease itself For example, the invention can be used to characterize the reaction properties of newly isolated proteases from natural variants of viral proteases, or proteases obtained by mutagenesis for improved properties (such as improved thermal stability, rate of reactivity, or alterations in specificity).

BRIEF DESCRIPTION OF THE FIGURES

FIG. 15 is a schematic of nucleotide sequence overlaps used to generate coding sequences for protease substrates. The schematic of FIG. 15 places a TEV protease site between the tetraCys motif and MBP. Other protease sites were created by use of the oligonucleotide primers indicated in Table 1.

FIG. 16A: The expression vector pVP14 creates an N-terminal fusion consisting of $His_6$, the tetraCys motif (CCPGCC) required for labeling with bis-arsenical fluorophores, the amino acids encoded by the attB1 recombination site, the desired protease recognition site, and the target gene. Proteolysis releases the small N-terminal peptide (~4 kDa) that contains the fluorescently labeled tetraCys motif The resulting change of fluorescence anisotropy can be monitored to determine the extent of proteolysis. FIG. 16B: The expression vector pVP15 creates a fusion protein consisting of an S-tag, $His_6$, MBP, the TEV protease recognition site, the tetraCys motif, the amino acids encoded by the attB1 recombination site, a second protease recognition site, and the target gene. Proteolysis at both protease sites will release the small internal peptide (~3 kDa) that contains the fluorescently labeled tetraCys motif.

FIGS. 17A and 17B are graphs depicting time-dependent changes in fluorescence anisotropy measured with two different tetraCys-labeled substrates incubated with the appropriate proteases. FIG. 17A: Substrate 25-F incubated with three different thrombin concentrations: ♦=0.26 μM; ▲=0.07 μM; and x=0.004 μM; and ●=control with no protease. FIG. 17B: Substrate 26-F incubated with three concentrations of TEV protease: ♦=1.4 μM;. ▲=0.35 μM; x=0.09 μM; ●=control with no protease. Measurements were taken at 3 min intervals, while data points are shown at 9 min intervals for clarity in the figure.

FIGS. 19A and 19B are graphs depicting initial proteolysis rate versus protease concentration for five combinations of tetraCys-labeled substrate and protease. FIG. 19A is a comparison of the proteolysis rates for trypsin, thrombin, and TEV protease. The series represented are: ■=trypsin with substrate 22-F; x=thrombin with substrate 25-F; and ♦=TEV protease with substrate 26-F. Specific reaction rates were calculated based on the slope of linear least squares curve fits shown as solid lines. Specific reaction rates in units of moles substrate proteolyzed per mole of protease per hour were as follows: trypsin; 760±60, thrombin; 240±20, TEV protease; 17.3±0.7. FIG. 19B is a comparison of initial proteolysis rates for thrombin, enterokinase, and Factor Xa as a function of the commercial supplier's reported activity. The units of thrombin were adjusted for equivalence with the unit definition used for enterokinase and Factor Xa. The series represented are: ●=enterokinase with substrate 23-F; ▲=Factor Xa with substrate 24-F; x=thrombin with substrate 25-F. Specific reaction rates in units of nmole substrate proteolyzed per unit enzyme per hour were: Factor Xa, 0.37±0.03; enterokinase, 0.130±0.007; thrombin, 0.20±0.02.

FIGS. 21A and 21B are graphs depicting the results following incubation of tetraCys-labeled protease substrates with alternative proteases to evaluate specificity. FIG. 21A depicts the fluorescence anisotropy data for the reaction of substrate 22-F; FIG. 22B depicts the fluorescence anisotropy for the reaction of substrate 25-F. Proteases tested included: ■=0.1 μM trypsin; x=0.13 μM thrombin; ●=0.11 U/μl enterokinase; ♦=2 μM TEV protease; ▲=0.06 U/μl Factor Xa; –=negative control.

FIGS. 23A and 23B are graphs showing a comparison of proteolysis of *Arabidopsis* proteins expressed from either pVP14 or pVP15, respectively. The fluorescence anisotropy assays were conducted as described in the Examples, except that the assay volume was 100 μL and 25% of the protein substrate was labeled with the fluorophore. FIG. 23A shows the results of a reaction of 2.0 μM At3g03410 expressed from pVP14. FIG. 23B shows the results of a reaction of 8.0 μM At3g16990 expressed from pVP15 and assayed in 50 mM Tris, pH 8.0, containing 50 mM NaCl. Control reactions (♦) contained no protease; proteolysis reactions contained 0.26 μM TEV protease (▲).

DETAILED DESCRIPTION OF THE INVENTION

Figure 1:
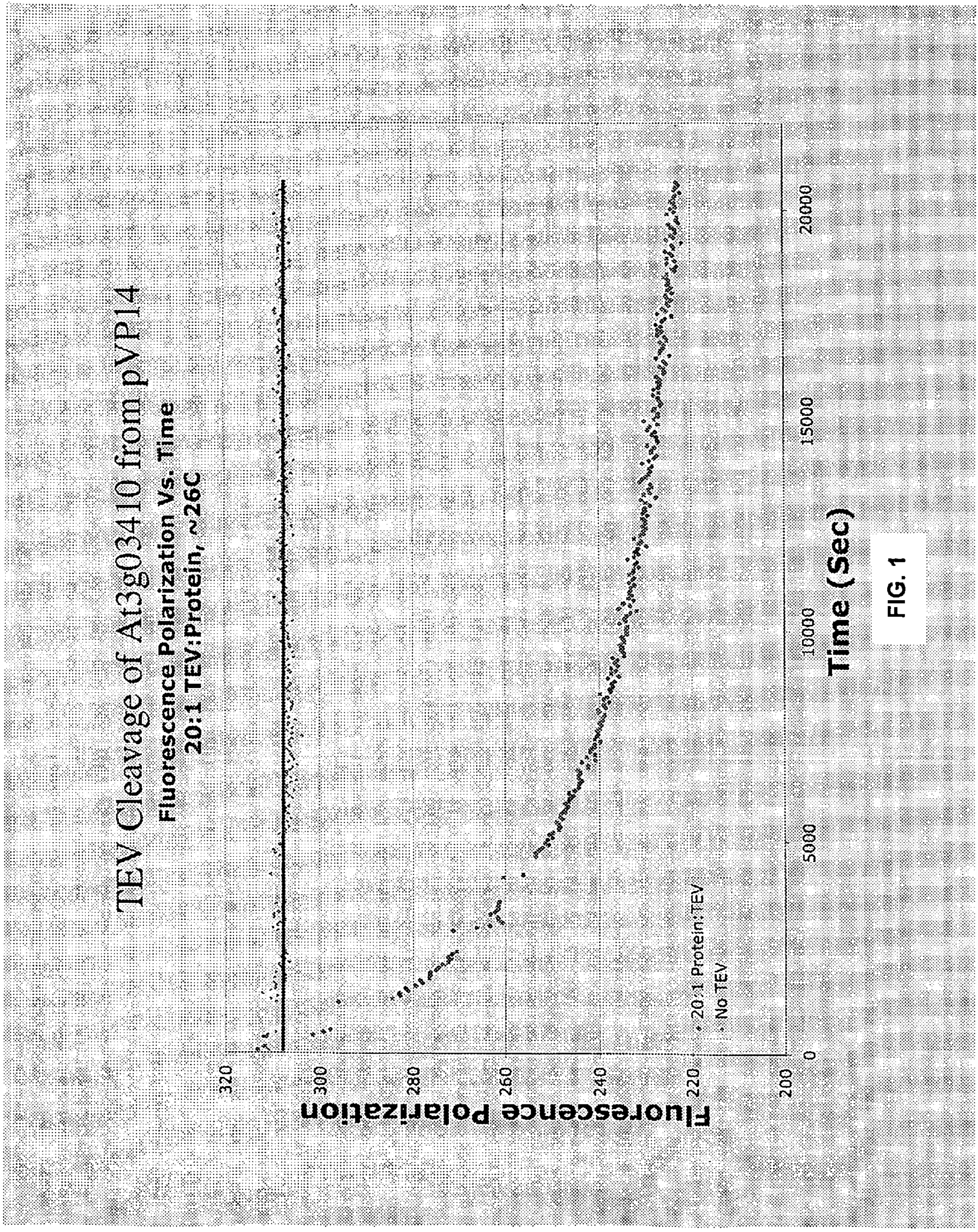
FIG. 1 is a graph of the cleavage of a fluorescent peptide substrate (generated from the pVP14 vector) over time by the tobacco etch virus (TEV) protease. Fluorescence polarization is shown on the Y-axis; time (sec) is shown on the X-axis. The control, representing the fluorescence polarization of the same clone in the absence of the TEV protease, is shown in the upper, substantially horizontal trace. The decrease in polarization in the presence of the TEV protease is shown in the lower, curved trace. The decrease in polarization is equivalent to the rate of the proteolytic cleavage under the described conditions.

The invention solves the problems of previous methods of investigating protease activity by using fluorescence polarization to measure the rate of protease activity. As described herein, the current application utilizes a fluorescent complex that requires two components before it fluoresces. Advantageously, one component of the fluorescent complex includes a fluorescence tag comprising a six amino-acid motif. Because the amino acid motif is small, it is amenable to being incorporated into a recombinant protein, preferably at either the C or N terminus. The other component of the complex comprises a biarsenical ligand. The affinity of the two components for each other allows them to be mixed in a solution, whereupon the protein-conjugated motif will bind strongly to the biarsenical ligand such that all of the peptide-conjugated motif is saturated. Upon binding of the amino acid motif to the ligand, the complex fluoresces brightly.

In the reagent, the fluorescent ligand is weakly bound to di-1,2-ethanedithiol ($EDT_2$) and does not exhibit any appreciable fluorescence. Upon mixing the reagent with the recombinant peptide/fluorescence motif, the $EDT_2$ is displaced by the amino acid motif with the result that the ligand-motif complex becomes more than 50,000 times more fluorescent than the reagent alone.

Specifically, the invention provides a method wherein a protein or peptide, which comprises a putative protease substrate, is conjugated to a fluorescence tag having a tetracysteine binding motif. The protease substrate is added to a reagent mixture, which contains the biarsenical ligand. The biarsenical ligand binds strongly to the amino acid motif by covalent bonds, thus creating a tightly bound complex that fluoresces. Upon introducing a protease to the mixture that cleaves the protein, the smaller fragment comprising the fluorescent complex will tumble in solution more rapidly than will an uncleaved substrate. Because the detection system uses fluorescence polarization, a tumbling fluorophore will not remain in the same plane of polarization and thus will not be detected in the same plane as the excitation energy. As a consequence, the efficiency of protease cleavage is easily determined by measuring the decrease in polarized light in the same plane as the excitation energy after introduction of the protease.

In one embodiment, the fluorescence tag is the tetra-cysteine motif Cys-Cys-Xaa-Xaa-Cys-Cys (SEQ. ID. NO: 1), where Cys is a cysteine molecule and where Xaa represents any amino acid (natural, unnatural, modified, etc.) other than cysteine. The ligand is a biarsenical compound having the structure shown in (a) where the dashed lines represent the bonds between the arsenic moieties and $EDT_2$ moieties that are displaced by bonds with the sulfide atoms of the cysteine residues of the fluorescence tag.

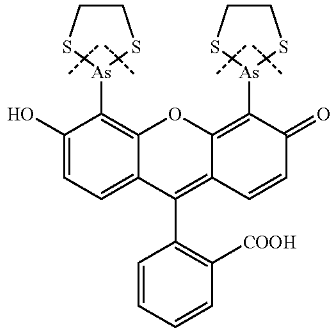

(a)

The fluorescence tag motif Cys-Cys-Xaa-Xaa-Cys-Cys is very rare in nature. Thus, there is little background/interference from non-specific binding. Upon combination of the fluorescent tag with the reagent ligand, each arsenic group forms two covalent bonds, one with each of the thiol groups of the two adjacent cysteine residues.

In the present instance, it has been found that a two-component system comprising a tetraCys-type tag and a corresponding complexing reagent that yields a fluorophore (e.g., the "FlAsH" and "ReAsH"-branded systems) can be used to monitor protease activity by conjugating the tag motif with a peptide or protein. With the tag in place, fluorescence polarization spectroscopy can be utilized to determine the activity of a protease that putatively catalyzes cleavage of the tagged peptide or protein.

In the present instance, a protease, which cleaves a protease substrate conjugated to the fluorescence tag/ligand complex, will result in a fluorophore, which rapidly tumbles out of the plane of polarization. In contrast, the uncleaved peptide/fluorescent complex, which rotates at a slower rate compared to the cleavage products, will emit a larger amount of energy in the same plane as the excitation energy. Thus, a determination of the activity and rate of the protease's ability to cleave the substrate is easily made in real time by measuring the decrease in the polarization signal. In short, protease activity is directly proportional to the rate of decrease in fluorescence polarization activity generated by the reaction products. The signal can be measured in real-time during the course of the reaction. Further, a measurement of the emitted energy not in the same polarized plane as the excitation energy provides a correction and normalization for the estimated protease activity in a single plane. Thus, polarization value (P) is calculated from the following equation:

$$P = \frac{Intensity_{vertical} - Intensity_{horizontal}}{Intensity_{vertical} + Intensity_{horizontal}}$$

where the vertical plane is defined as the plane of excitation energy and the horizontal plane is defined as the plane of energy emitted by the cleaved fluorophor complex.

In one embodiment of the present invention, a protein or peptide is selected in order to test its efficacy as a substrate for some known protease. The fluorescence tag is conjugated to the protease substrate resulting in a tagged substrate. Upon mixing the fluorescence tagged substrate with the reagent containing the biarsenical ligand, the cysteine groups of the fluorescence tag displace the $EDT_2$ moiety from the ligand, binding the ligand to the substrate and resulting in the formation of a fluorescent complex.

In one embodiment, the fluorescence tag can be bound to the substrate by well-known biochemical methods. For instance, a peptide bond can be introduced between the fluorescence tag motif and the suspected protease substrate thereby creating a tagged substrate.

In another embodiment of the invention, the fluorescence tag is added to the suspected protease substrate by genetically engineering the motif into the substrate at the nucleotide level. For example, a peptide could be mutated to include the Cys-Cys-Xaa-Xaa-Cys-Cys motif as has previously been done. (See, Griffin et al., Science 281, 269-272).

In another embodiment, the fluorescence tag motif can be genetically engineered into the substrate by using any molecular cloning method. In this embodiment, a nucleotide sequence coding for a protease substrate or putative protease substrate is put into a vector using appropriate splice sites in a multiple cloning site on the vector.

It is another aspect of the invention that the vector has a promoter region followed by a sequence coding for an affinity purification tag moiety. This is followed by a peptide or protein having a suspected protease cleavage site.

Using this method, a library of unknown or uncharacterized nucleotide sequences can be put in an appropriate vector. The vector may be designed to include a purification tag such as a poly-His tag. Following expression of the protein from the vector, the protein is purified using the purification tag. In instances where the protein is excreted, the cell media can be filtered to remove the cells and the filtrate put directly on an affinity column appropriate for binding the purification tag. In other cases, the cells can be lysed chemically or mechanically and the lysate applied to the affinity resin. When the His purification tag is used, a nickel based affinity resin specifically binds the His-tag. Such resins are commercially available from a variety of sources such as Novagen (Madison, Wis.), Invitrogen (Carlsbad, Calif.), and Qiagen (Valencia, Calif.) to name a few. Once bound to the column resin, His-tagged proteins are eluted using a low pH buffer or by competitive adsorption with imidazole.

Other purification tags can be used, however. For example glutathione S-transferase is one of the oldest fusion tags (or purification tags) and is adsorbed to a glutathione-based resin when used. Glutathione S-transferase systems are available from Amersham Biosciences (Thousand Oaks, Calif.), Invitrogen (Carlsbad, Calif.), and Novagen (Madison, Wis.) to name a few. Other examples of purifications tag systems are the HAT and PROTet systems from Clontech (Palo Alto, Calif.), the strep-tag system from IBA GmbH (St. Louis, Mo.), the PinPoint, biotin-avidin system from Promega (Madison, Wis.), and the calmodulin-binding peptide purification system from Stratagene (La Jolla, Calif.).

Using this design, a fusion protein can be expressed from a vector. In one preferred embodiment, the vector is designed for expression in bacteria, such as, *E. coli*. However, the vector can be designed for most culturable cells, including mammalian cells such as HeLa cells, CHO cells, and baculovirus culture. All that is necessary is an appropriate promoter region and compatibility with the host's genetic machinery. In addition, the present invention can also be applied in cell-free protein translation systems.

Further, it will be apparent to those of skill in the art the invention described herein can be used to investigate protease/substrate interactions regardless of the method or extent of purification. For example, media from the expression system can easily be passed through a filter such as a "CENTRICON"-brand filter (available in various exclusion sizes from Millipore, Bellerica, Mass., Cat. Nos. 4240, 4242, 4243, 4208, 4244 for various molecular weight concentrations), to exclude intact cells and cellular debris. The filtrate can then be used directly in the subject invention. In addition, the invention can be used with whole cell and unpurified extracts as well.

Following elution of the recombinant protein containing the protease substrate, fluorescence polarization can be practiced on the fusion protein.

In yet another embodiment of the invention, the vector may be constructed as described above, but with the exception that the vector also encodes a solubility tag. One problem with the heterologous expression of proteins is that the host cell cannot properly fold or modify the protein post-translationally and the foreign protein often forms insoluble inclusion bodies within the cell. Inclusion of a solubility tag improves the ability of the host to express the foreign protein. This design allows the solubility tag to be fused with the fluorescent complex upon cleavage of the complex from the protease substrate.

By including a solubility tag in the vector, the rate of screening of known or unknown protease substrates is increased because a nucleic acid sequence coding for the solubility tag can be inserted into the vector and purified as explained above. This method allows an otherwise insoluble target protein to be produced without having to resort to denaturing the protein to purify it, and then renaturing the recombinant protein to return it to its native conformation. Examples of solubility tags known in the art include maltose binding protein (MBP), N-utilization substance protein A (Nus-A), bacterioferritin (BFT), GrpE, and thioredoxin (TRX). See, Davis et al., Biotechnol Bioeng. 1999 Nov. 20;65 (4):382-8; and Fox et al. Methods Mol Biol. 2003;205:99-117 for discussions of various solubility tags.

Further, as those in the field will appreciate, while the invention can be used to screen a library of expressed proteins for their suitability to act as a substrate for a known protease, the invention can also be used to screen potential proteases for effective substrates. In this embodiment, known peptides or proteins can be contacted with a suspected protease and the proteolytic activity of the protease on any particular substrate can be monitored, in real time, using the invention.

The vectors disclosed in the Examples have a modular construction. The vectors comprise, for example, defined modules (or domains or regions) for driving promoter-induced expression, for purifying the expressed protein by affinity chromatography, for promoting the solubility of the expressed fusion proteins, for facilitating the detection and quantification during expression and purification, for enabling proteolysis of fusion proteins, and for real-time monitoring of the proteolysis reaction.

The promoter-driven expression modules are defined, dimensioned, and configured to provide regulated control of the transcription of the desired gene sequences (DNA) into corresponding mRNA molecules that contain ribosome binding sites suitable for facilitating translation of the mRNA into a corresponding protein by the ribosomes present in the expression host. The properties of the promoter system will be specific to the organism used as the expression host. The most desirable characteristics for a promoter to be included in the vectors according to the present invention is the ability of the promoter to maintain protein expression at undetectable levels before induction of gene expression, and to give a controllable and very large increase in gene expression after induction.

Any promoter now known or developed or discovered in the future can be used in the present invention. The vectors disclosed in the Examples use of the viral T5 promoter, which is preferred for expression in *E. coli*. Other suitable promoters include, without limitation the viral T3 and T7 promoters, the bacterial ara promoter, the lac promoter, the trp promoter, the hybrid tac promoter, and many others.

Affinity purification modules are defined, dimensioned, and configured to include peptide or protein sequences suitable for affinity purification. Vectors encoding affinity modules such as $His_8$, $Arg_8$, or others known to the art are can be used in the present invention. Both $His_6$ and $His_8$ have been tested, with tighter binding to the purification resin observed with $His_8$. Other affinity modules often described in the literature and which can be used in the present invention include (but are not limited to): glutathione-S-transferase (immobilized glutathione columns), maltose binding protein (amylose), chitin binding domain (immobilized chitin), polyArg (cation exchange), and others.

Solubility modules for use in the present invention are defined, dimensioned, and configured to encode peptides or proteins that enhance the folding and/or solubility of the ultimate protein product when expressed as a fusion construct. Any solubility tag, module, region, or domain now known in the art or developed in the future can be used in the present invention. Solubility modules that can be used in the present invention include, but are not limited to, maltose binding protein, thioredoxin, glutathione-S-transferase, NusA, all of which are known in the relevant literature.

Proteolysis modules for use in the present invention are defined, dimensioned, and configured to provide a protease cleavage site and the flanking amino acid sequences required for high fidelity of the proteolysis reaction. The ideal proteolysis module enables proteolysis of a high percentage of the desired target protein from the fusion protein and also the ability to work with a wide range of target proteins. Where two distinct (i.e., mutually exclusive) proteolysis modules are used, it is generally preferred that the corresponding proteolysis reactions have compatible reaction conditions. If the reaction conditions can remain the same for each of the two proteolysis reactions, that greatly speeds the procees. While compatible reaction conditions are preferred, the reactions conditions do not necessarily need to be compatible because the two distinct proteolysis reactions can be run as sequential reactions per the procedure outlined for small-scale screening. See Example 5. In that example, the product of the HRV 14 3CP cleavage reaction is simply diluted into TEV cleavage buffer. Therefore, the HRV 14 3CP cleavage buffer does not necessarily need to be compatible with TEV protease reaction and vice versa. Any protease cleavage site now known or developed in the future can be used in the present invention, including, without limitation, recognition sequences for the following commercially available proteases: enterokinase, factor Xa, thrombin, and many others others.

Detection modules for use in the present invention are defined, dimensioned, and configured as vectors encoding detection modules such as the tetraCys motif, S-tag, and other target-independent methods such as haloalkane dehalogenase. The tetracys motif is preferred. The S-tag has been evaluated and it does function (results not shown). It is not preferred however, because it is overly sensitive. A significant amount of dilution testing is required when using the S-tag, which makes the resulting assay cumbersome.

The tetraCys domain reacts with the Invitrogen commercial reagent, which is currently marked under the unregistered trademark "Lumio."

Any means of cloning the target gene into the appropriate position in the vector to provide an in-frame fusion protein with the other tags or modules present in the construct can be utilized. A host of such methods are known in the art and will not be discussed in great detail herein. For an exhaustive treatment of molecular cloning methods and laboratory protocols, see Sambrook & Russell, "Molecular cloning: A laboratory manual," Cold Spring Harbor Laboratory Press, Cold Spring Harbor, N.Y., 2001. A number of pre-packaged kits for molecular cloning can also be obtained commercially. The vectors described in the Examples were fabricated using Gateway technology and kits purchased from Invitrogen. Other recombination systems are also available commercially from several international suppliers, including Promega, Stratagene, and others. Classic digestion/ligation reactions, as described in Sambrook & Russell, can also be employed successfully.

EXAMPLES

The following Examples are included solely to provide a more complete and consistent understanding of the invention disclosed and claimed herein. The Examples do not limit the scope of the invention in any fashion.

Example 1

Fluorescence Polarization of a Peptide Cleaved by the Tobacco Etch Virus (TEV)

A vector was constructed having segments comprising a His tag for purification purposes, the tetraCys tag motif, a tobacco etch virus (TEV) cleavage site, and a target protein being investigated. The vector, named pVP-14 (SEQ. ID. NO: 2), was derived from pDEST17 (Invitrogen, Carlsbad, Calif., Cat. No. 11803-012) and encodes the expressed sequences:

His-tetraCys tag-TEV-Target protein, where "His" denotes a poly-His purification tag, "tetraCys tag" denotes the fluorescence tag, "TEV" denotes the tobacco etch virus cleavage sequence, and "target protein: denotes a protein or peptide sequence of interest.

The pVP14 vector was created from pDEST17 using the ExSite-brand site-directed mutagenesis kit (Stratagene, La Jolla, Calif.). The forward primer (FLUF) was 5'-phosphorylated and further comprised the sequence TGT TGC CCA GGA TGC TGT ACA AGT TTG TAC AAA AAA GCT GAA CGA GAA (SEQ. ID. NO: 3). The reverse primer (pD17FR) was not 5'-phosphorylated and consisted of the sequence TGA TTC GAG GTG ATG GTG ATG GTG ATG GTA GTA CGA CAT AT (SEQ. ID. NO: 4). Polymerase chain reaction (PCR) amplifications were performed using YieldAce-brand DNA polymerase (Stratagene) in a DYAD-brand Peltier thermocycler (MJ Research, Waltham, Mass.). The reaction cycle comprised 5 min at 94° C., 1 min at 55° C., 6 min and 45 sec at 72° C., followed by 14 cycles of 1 min at 94° C., 1 min at 65° C., 6 min and 45 sec at 72° C., followed by 5 min at 72° C. and then 4° C. until needed. The ~6.5 kb amplified DNA fragment was purified by agarose gel electrophoresis and ligated with T4 DNA ligase using a temperature program comprising 30 sec at 4° C. and 30 sec at 30° C. repeated continuously for ~18 h. Competent *E. coli* DB3.1α cells (available from many commercial sources, including Invitrogen) were transformed with the ligation reaction mixture. Plasmids recovered from transformed colonies were sequenced to verify successful mutagenesis.

Upon addition of the tetraCys reagent, the complex fluoresced brightly. When the TEV protease was added to the mixture the fluorescent polarization of the mixture dropped rapidly as illustrated in FIG. 1. This Example illustrates that the decrease in the polarization signal can be used to measure protease activity in real-time.

Example 2

Fluorescence Polarization of a Peptide Conjugated to a Solubility Protein

A vector was constructed having a His tag for purification purposes, a solubility tag comprising a maltose binding protein (MBP), a tobacco etch virus (TEV) cleavage site, a second His tag, the tetraCys tag, a second TEV site, and the target protein. The vector named pVP-15 (SEQ. ID. NO: 5) is derived from pVP13-GW (SEQ. ID. NO: 6). The pVP13-GW vector is derived from pQE80 (SEQ. ID. NO: 7), which is available commercially from Qiagen (Valencia, Calif.). pVP-15 includes the expressed sequences:

His-MBP-TEV-His-tetraCys tag-TEV-target protein.

The plasmid pVP13-GW, a pQE-80-derived vector used for expression of *Arabidopsis thaliana* genes in *E. coli* at University of Wisconsin Center for Eukaryotic Structural Genomics, was used as the parent for production of pVP 15. Proteins expressed from pVP13-GW contain an S-Tag for detection (Kim & Raines (1993) *Protein Sci.* 2:348-356), a His$_6$ tag for purification, and MBP to enhance target protein folding. To produce pVP15, the linker peptide between MBP and the attB1 sequence of pVP13-GW was modified to include a TEV protease cleavage site, a His$_6$ tag, and the tetraCys motif. The second His$_6$ tag was added to allow binding of the tetraCys motif during subtractive immobilized metal ion affinity chromatography (IMAC) purification after proteolysis (Sambrook & Russell, "Molecular cloning: A laboratory manual," in: Vol. 3, Cold Spring Harbor Laboratory Press, Cold Spring Harbor, N.Y., 2001, pp. 15.44-15.48). The preferred IMAC protocol is provided at the end of this Example. To modify pVP13-GW, the FLUF forward primer described above (SEQ. ID. NO: 3) was used. The reverse primer (p13HTF) consisted of the sequence: ATG GTG GTG GGA CTG GAA GTA CAG GTT TTC GTT GTT GTT CGA GCT CGA ATT AGT CTG CGC GTC TTT CAG GGC TTC (SEQ. ID. NO: 8). Thermocycling was conducted as described for the construction of pVP14 with the exceptions that the annealing temperature was 69° C., 12 cycles were used instead of 14, and the amplified band was not gel purified before ligation.

Figure 2:
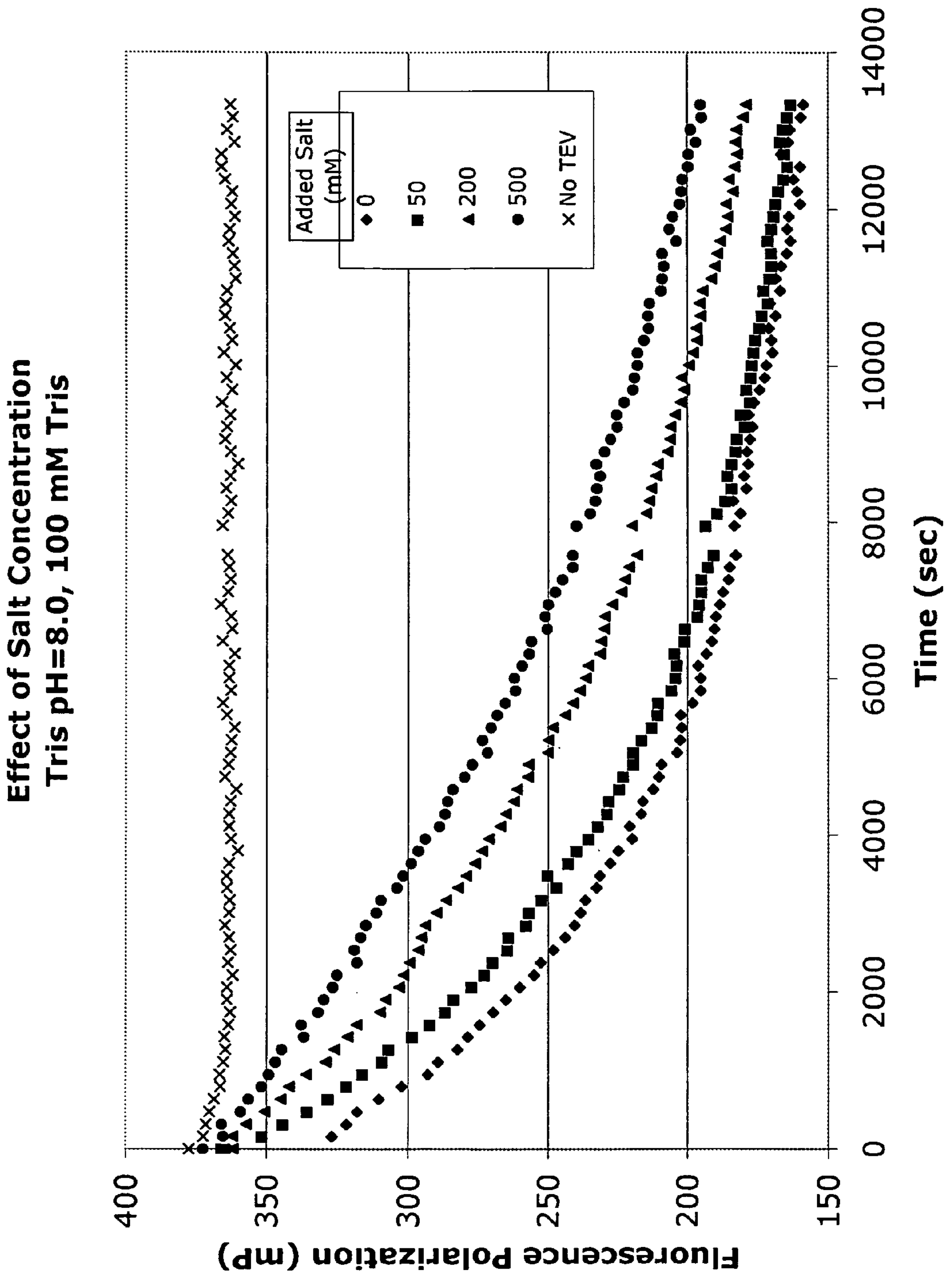
FIG. 2 is a graph of the cleavage of a peptide substrate (generated from the pVP15 vector) by the TEV protease. Fluorescence polarization is shown on the Y-axis; time (sec) is shown on the X-axis. The plots represent the change in the rate of proteolysis as a function of salt concentration, and were measured in real-time using the present invention. From top to bottom: the upper plot shows the rate at a salt concentration of 500 mM, followed by a plot of the rate at a salt concentration of 200 mM, followed by a plot of the rate at a salt concentration of 50 mM, followed lastly by a plot of the rate at a salt concentration of 0 mM.

The MBP portion of the plamsid was amplified from the vector pMal-C2 (SEQ. ID. NO: 9) available commercially from New England Biolabs (Beverly, Mass.). Upon addition of the tetraCys reagent, the fluorescence tag conjugated to the target protein binds the biarnsenical compound in the solution. The complex and the solution fluoresced brightly in the plane of polarization. When the tobacco etch virus protease is added to the solution, the fluorescence polarization dropped rapidly as shown in FIG. 2.

All cloning was completed using the Gateway-brand cloning system for recombination cloning, available commercially from Invitrogen. A nested PCR was used to incorporate different protease cleavage sites between the attB1 sites and the *E. coli* maltose binding protein. Table 1 shows sequences of the primers used for PCR in the 5' to 3' direction, while FIG. 15 shows a schematic representation of the 2-step PCR used to create DNA inserts for recombination into the attB1 recombination sites of either pVP14 or pVP15. All forward primers for the first-step PCR included the nucleotides required for the protease cleavage site followed by 27 nucleotides identical to the MBP gene sequence. Reverse primers were identical for all substrates, and consisted of the sequence shown in FIG. 15. The MBP template material was derived from the vector pMal-C2 (SEQ. ID. NO: 9). The first PCR incorporated 5' and 3' internal primers (see Table 1 and FIG. 15) and the reaction was cycled as follows: 5 min at 95° C., 21 cycles of 30 sec at 94° C., 30 sec at 55° C., 1 min and 30 sec at 72° C., followed by 7 min at 72° C. and then 4° C. until needed.

For the second PCR, 10 µL of the first PCR was transferred to a second 50 µL PCR containing fresh nucleotides, DNA polymerase, reaction buffer and 5' and 3' external primers (see Table 1 below and FIG. 15). The conditions for the second PCR were identical to the first. The PCR product was subjected to a BP recombination reaction with pDONR221. The recombination product was transformed into *E. coli* DB3.1α.

TABLE 1

| Forward Primers Used to Incorporate Protease-Susceptible Sequences | | | |
|---|---|---|---|
| 21-F | 5' internal primer | AAC CTG TAC TTC CAG - MBP | (SEQ. ID. NO: 10) |
| | 5' external primer | GW - GAA AAC CTG TAC TTC CAG | (SEQ. ID. NO: 11) |
| 22-F | 5' internal primer | TTC CTC GGC ATG GTC - MBP | (SEQ. ID. NO: 12) |
| | 5' external primer | GW - CGC TCC TTC CTC GGC ATG GTC | (SEQ. ID. NO: 13) |
| 23-F | 5' internal primer | GAT GAC GAT GAC AAG - MBP | (SEQ. ID. NO: 14) |
| | 5' external primer | GW - GAA GAT GAC GAT GAC AAG | (SEQ. ID. NO: 15) |
| 24-F | 5' internal primer | ATC GAA GGA CGC - MBP | (SEQ. ID. NO: 16) |
| | 5' external primer | GW - ATC GAA GGA CGC | (SEQ. ID. NO: 17) |
| 25-F | 5' internal primer | GTA CCA CGT GGC AGT - MBP | (SEQ. ID. NO: 18) |
| | 5' external primer | GW - CTA GTA CCA CGT GGC AGT | (SEQ. ID. NO: 19) |
| 26-F | 5' internal primer | AAC CTG TAC TTC CAG TCC - MBP | (SEQ. ID. NO: 20) |
| | 5' external primer | GW - GAA AAC CTG TAC TTC CAG | (SEQ. ID. NO: 21) |
| | MBP = AAA ATC GAA GAA GGT AAA CTG GTA ATC | | (SEQ. ID. NO: 22) |
| | GW = CGGG ACA AGT TTGTAC AAA AAA GCA GGC TCC | | (SEQ. ID. NO: 23) |

The recombination region of plasmids isolated from positive transformants was sequenced before being transferred by the LR reaction (included as part of the Gateway-brand cloning system) to the destination vector pVP14. This recombination created the $His_6$-tetraCys-X-MBP constructs used for protein expression, where "X" represents an engineered protease recognition site. The N-terminal amino acid sequences of the expressed fusion proteins are shown in Table 2.

TABLE 2

Amino Acid Sequences of Various $His_6$-Cys4-X-MBP Protease Substrates

| Substrate ID | Intended Protease Susceptibility | Sequence[a] |
|---|---|---|
| 21-F | None[b] | (SEQ. ID. NO: 24) MSYYHHHHHHLESCCPGCCTSLYKKAGSENLYFKS-MBP[c] |
| 22-F | Multiple[d] | (SEQ. ID. NO: 25) MSYYHHHHHHLESCCPGCCTSLYKKAGSRSFLGMV-MBP |
| 23-F | Enterokinase | (SEQ. ID. NO: 26) MSYYHHHHHHLESCCPGCCTSLYKKAGSEDDDDK↑-MBP |
| 24-F | Factor Xa | (SEQ. ID. NO: 27) MSYYHHHHHHLESCCPGCCTSLYKKAGSIEGR↑-MBP |
| 25-F | Thrombin | (SEQ. ID. NO: 28) MSYYHHHHHHLESCCPGCCTSLYKKAGSLVPR↑GS-MBP |
| 26-F | TEV Protease | (SEQ. ID. NO: 29) MSYYHHHHHHLESCCPGCCTSLYKKAGSENLYFQ↑S-MBP |

[a]The tetraCys motif used for binding the FlAsH-type reagent is highlighted in grey. The underlined residues make up the protease recognition site. The susceptible peptide bond found in each protease site is indicated with an arrow.

TABLE 2-continued

| Amino Acid Sequences of Various $His_6$-Cys4-X-MBP Protease Substrates | |
|---|---|
| Substrate ID | Intended Protease Susceptibility Sequence[a] |

[b]The TEV site was substituted with Lys in the P1' position. Previous studies have shown this alteration to the TEV site results in a loss of proteolysis, Kapust, et al. (2002) Biochem. Biophys. Res. Commun. 294:949-955.
[c]The first 10 residues in the N-terminal sequence of MBP are KIEEGKLVIW (SEQ. ID. NO: 30).
[d]The substrate 22-F contains cleavage sites for multiple proteases, including enterokinase, Factor Xa, and thrombin. A TEV protease recognition site was not present.

*Arabidopsis thaliana* open reading frames At3g16990 and At3g03410 were cloned using a protocol identical to that described above with the exception that the 5' sequences specific for these genes were substituted for the MBP sequence. The entire genome of *Arabidopsis thaliana* has been sequenced. For extensively detailed information on Arabidopsis sequences, consult The Arabidopsis Information Resource (TAIR), Stanford, Calif. TAIR is a collaboration between Stanford University and the National Center for Genomic Resources, Santa Fe, N. Mex. Funding for TAIR is provided by the National Science Foundation, grant no. DBI-9978564. The PCR products of the two-step amplification were transferred to pDONR221 (from Invitrogen, SEQ. ID. NO: 31) and sequenced. Verified sequence clones were transferred into either pVP14 or pVP15 using the LR reaction to create expression plasmids.

Figure 16A:
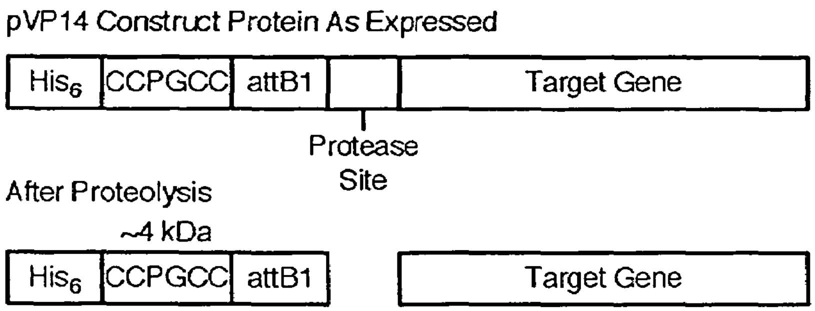
FIGS. 16A and 16B are schematic representations of fusion proteins created from the expression vectors pVP14 and pVP15 and the peptides released after proteolysis.

FIG. 16A shows schematic representations of the fusion proteins described here. The expression vector pVP14 (SEQ. ID. NO: 2) encodes an N-terminal $His_6$ affinity tag, the tetraCys (CCPGCC, SEQ. ID. NO: 1) sequence for site-specific labeling with the tetraCys reagent and the attB1 site-specific recombination site. Upon proper preparation of a DNA insert (described below), a fusion protein comprising the vector-encoded protein sequences, a protease recognition sequence, and a desired target protein can be expressed. For the Examples, *E. coli* MBP was used as a convenient, highly soluble target protein. Treatment of the fusion protein obtained from pVP14 with the appropriate protease releases a ~4 kDa fluorescent peptide from the N-terminal of the desired target protein.

Figure 16B:
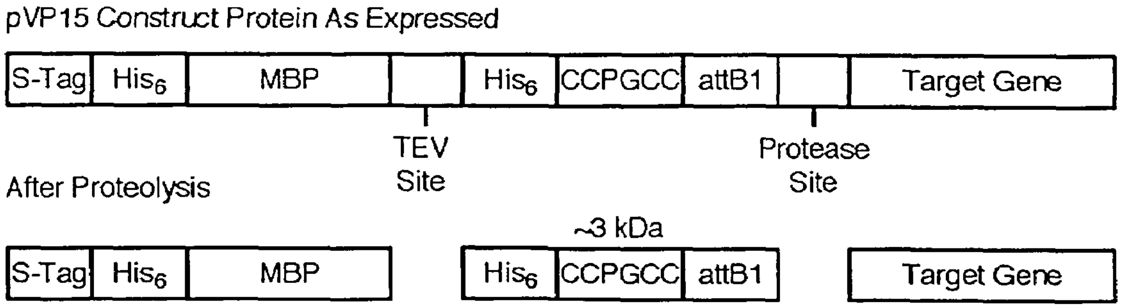

FIG. 16B shows a schematic representation of a fusion protein produced from pVP15 (SEQ. ID. NO: 5). This expression vector encodes an N-terminal S-tag, a $His_6$ affinity tag, MBP, a TEV protease site, a second $His_6$ affinity tag, the tetraCys motif, and the attB1 sequence. Upon proper insertion of a cloned gene into the recombination site, a fusion protein containing an internal tetraCys motif bound by two protease sites is created (FIG. 16B). Treatment of this fusion protein with the appropriate combination of proteases releases a ~3 kDa fluorescent peptide from the linker peptide between the S-tag-$His_6$-MBP solubility domain and the desired target protein.

The preferred IMAC procedure for isolating Arabidopsis proteins expressed from *E. coli* is as follows. The overall approach is to automate the protocols as much as possible, while preserving quality in the final product. The affinity tags are an essential part of the automation, and His tags are the preferred affinity tags. Complete removal of the His tag is also a high priority. Because the TEV protease site is well-characterized, it is the preferred cleavage site.

The overall process includes sonication of the cell pellets, a first immobilized nickel column to capture the fusion protein and separate it from other cellular proteins, followed by protease cleavage, followed by a second immobilized nickel affinity column to capture the tag and separate it from the target protein.

Materials:

Sonication and Chromatography Buffers: TCEP (Pierce Product #20490) is added to all sonication and chromatography buffers on the day of use to a final 0.3 mM. TCEP is added as a solid to each buffer, which are pH-adjusted so that the drop in pH caused by adding TCEP results in a solution of the correct pH. Buffers are vacuum-filtered through a 0.22 μm filter before use. The preferred filters are large (0.5-1.0 L) disposable filters with polyethylene sulfone (PES) membranes.

1 L Sonication/Wash Buffer:

20 mM $NaH_2PO_4$ (MW 119.96), 2.40 g 500 mM NaCl (MW 58.44), 29.22 g

20% (v/v) ethylene glycol (MW 62.07), 200 ml

Final pH: 7.5

1 L IMAC-A:

20 mM $NaH_2PO_4$ (MW 119.96), 2.40 g 500 mM NaCl (MW 58.44), 29.22 g

Final pH: 7.5

1 L IMAC-B:

20 mM $NaH_2PO_4$ (MW 119.96), 2.40 g 500 mM NaCl (MW 58.44), 29.22 g 350 mM Imidazole (MW 68.08), 28.83 g Final pH: 7.5

Desalting Buffer:

20 mM $NaH_2PO_4$ (MW 119.96), 2.40 g 100 mM NaCl (MW 58.44), 5.84 g

Final pH: 7.5

Dialysis Buffer 20×Stock Solutions:

(1) Prepare 1 L of 20×100 mM NaCl+10 mM Mes pH=6.15.

a. Weigh out the chemicals and place them in a 1 L flask. For a 1 L 20× stock the appropriate weight would be NaCl=116.88 g and Mes=39.04 g.

b. Add 800 ml of MQ-water to the flask and chemicals.

c. Adjust the pH to 6.15 of the 20×stock with 10 M NaOH.

d. Fill a clean 1 L graduated cylinder with the 800 ml of buffer, then adjust the final volume to 1 L with MQ-water.

e. Check the pH of the 20×stock and adjust if necessary.

f. Filter 20×buffer stock to remove particulates, and store at 4° C.

(2) Prepare 1 L of 20×100 mM NaCl+10 mM Hepes pH=7.20.

a. Weigh out the chemicals and place them in a 1 L flask. For a 1 L 20× stock the appropriate weight would be NaCl=116.88 g and Hepes=47.66 g.

b. Add 800 ml of MQ-water to the flask and chemicals.

c. Adjust the pH to 7.20 of the 20×stock with 10 M NaOH.

d. Fill a clean 1 L graduated cylinder with the 800 ml of buffer, then adjust the final volume to 1 L with MQ-water.

e. Check the pH of the 20×stock and adjust if necessary.

f. Filter 20×buffer stock to remove particulates.

g. Store at 4° C.

(3) Prepare 1 L of 20×100 mM NaCl+10 mM Tris pH=8.00.

a. Weigh out the chemicals and place them in a 1 L flask. For a 1 L 20× stock the appropriate weight would be NaCl=116.88 g and Tris=24.22 g.

b. Add 800 ml of MQ-water to the flask and chemicals.

c. Adjust the pH to 8.00 of the 20×stock with 10 M NaOH.

d. Fill a clean 1 L graduated cylinder with the 800 ml of buffer, then adjust the final volume to 1 L with MQ-water.

e. Check the pH of the 20×stock and adjust if necessary.

f. Filter 20×buffer stock to remove particulates.

g. Store at 4° C.

(4) Protease Inhibitor Cocktail. This recipe is for a 60×solution which gives the indicated molarity when added to 59 ml of Sonication/Wash buffer.

1.0 uM E-64 (Cat. No. 324890-Y, Calbiochem), 5 mg (Cysteine Prot I)

0.5 mM Benzamidine (Cat. No. 199001-Y Calbiochem), 1.1 g (Serine Prot I)

1.0 mM EDTA, tetrasodium dihydride salt, 5.82 g (Metallo Prot I) Milli-Q H2O, 233.2 mL Dispense as 1 mL aliquots in vials, and store at −20° C.

Methods:

Purification of S-Peptide-$(His)_6$-MBP-Tagged Fusion Proteins (Day 1):

Activation of Column with $NiCl_2$:

(1) Wash fresh iminodiacetic acid (IDA) column with 50 ml of Milli-Q water to remove ethanol solution from the column.

(2) Wash the column with 10 ml of 100 mM $NiCl_2$ solution, to yield a nickel-iminodiacetic acid (Ni-IDA) column.

(3) Wash the column with 10 ml of Milli-Q Water.

Sonication of Cell Suspension (1) Thaw cell paste.

(2) Add Sonication/Wash buffer (ratio of 1 g cell paste to 5 ml of Sonication/Wash buffer) and 1 ml of protease inhibitor cocktail to the cell suspension.

(3) Transfer cell suspension to metal tubes.

(4) Sonicate cell suspension (5) Dispense cell lysate into Oak Ridge centrifuge tubes.

(6) Centrifuge cell lysate at 75,600×G for 20 min at 10° C. Supernatant should be very clear of debris. If the supernatants are turbid or pellets are loose, decant supernatants into new tubes and repeat the centrifugation. Take 20 μl aliquot for SDS-PAGE analysis.

Offline Protein Loading onto the Ni-IDA Column (1) Load supernatant onto Ni-IDA columns using a peristatic pump and a 0.8 μm syringe filter at a flow rate of 5.0 ml/min.

(2) After loading, wash the column with 25 ml of Sonication/Wash buffer.

Gradient Elution of Fusion Proteins (First IMAC Capture)

(1) Connect the protein-charged Ni-IDA column to an AKTA Prime-brand chromatography system (Amersham Biosciences, a wholly-owned subsidiary of GE Healthcare, Waukesha, Wis.). (The AKTA Prime-brand system generally comprises a control system, pump, fraction collector and chart recorder, together with valves for buffer selection, sample injection, gradient formation and flow diversion. It is compatible with a wide range of column types.)

(2) Elute protein using a gradient from IMAC-A buffer to IMAC-B buffer over 15 column volumes (75 ml) at a flow rate of 5 ml/min. Set fraction size to 5 ml and collect each fraction.

(3) Take a 20 μl of aliquot from each fraction and analyze protein purity by SDS-PAGE.

(4) Pool the appropriate fractions that contain 95% pure fusion protein.

(5) Exchange the buffer solution using a desalting column at a flow rate of 10 ml/min.

Purification of Target Protein (Day 2): Cleavage of Fusion Protein with TEV Protease:

(1) Read absorbance of protein solution at 280 nm and calculate the concentration of fusion protein.

(2) Add TEV protease (1:100 ratio, w/w) and run the protease reaction at 30° C. for 3 hrs.

(3) Take 20 μl of aliquot from TEV reaction mixture and check the degree of cleavage by running SDS-PAGE. If the cleavage reaction processes less than 90% (based upon visual inspection), add more TEV protease (1:100 ratio, w/w) for an additional 3 hrs.

Purification of Target (Second IMAC Capture)

(1) Inject TEV reaction mixture into Superloop (Amersham, 50 ml) through a 0.8 mm syringe filter.

(2) Load protein solution onto Ni-IDA column at a flow rate of 2 ml/min and collect flow through fraction. At this point, target protein binds Ni-IDA column nonspecifically.

(3) Elute target protein using a gradient from IMAC-A buffer to 30% of IMAC-B buffer over 10 column volumes (50 ml) at a flow rate of 2 ml/min.

(4) Set fraction size 2 ml and collect each fraction.

(5) Watch the elution profile and take a 20 μl aliquot from the fractions that match with protein elution peaks.

(6) After SDS-PAGE analysis, pool the fractions that show 90% or greater of target protein purity.

(7) Exchange the buffer solution using a desalting column at a flow rate of 10 ml/min using the AKTA Prime system.

(8) Determine concentration by optical density at 280 nm.

Concentrating the Target Protein: (Day 3):

(1) The protein should be concentrated to at least 15 mg/ml. Using the concentration determined in the previous section, determine the final volume needed for a concentration of 15 mg/ml.

(2) Concentrate the protein solution using a YM-10 Centriprep filter (Millipore) at 3,000×G. Measure the absorbance at 280 nm of the purified protein and calculate protein concentration. If the protein is concentrated to at least 15 mg/ml, proceed to the dialysis step. If the protein is not sufficiently concentrated, continue concentrating with a YM-10 Centricon filter (Millipore) at 3000×G until at least 15 mg/ml is reached.

Dialysis:

To dialyze from about 1 to about 10 ml of 15 mg/ml protein, dialyze the protein twice (with a change of buffer) for no less than 4 hours per dialysis and no more than 20 hours. Depending on the calculated isoelectric point of the protein, choose the appropriate 20×dialysis buffer and dilute 50 ml of buffer stock into 950 ml of MQ-water straight from the MQ system. Place the newly created 1×dialysis buffer into a 1 L beaker then add a 2 inch stir bar. Add 0.3 mM TCEP (86 mg) to the liter of 1×buffer. Verify the pH is correct and adjust with 10 M-NaOH if needed. Dialyze the protein in a 10,000 nominal molecular-weight cut-off "Slide-A-Lyzer"-brand filter (Pierce) for at least 4 hours and then place into a fresh 1 L of dialysis buffer for overnight.

Storage (Day 4):

(1) Check the protein concentration against the dialysis solution as an 280 nm blank.

(2) Drop freeze in liquid nitrogen and store as approx. 30 μl beads.

Example 3

Cleavage Efficiency of the Tobacco Etch Virus Protease in Various Solutions as Measured by Fluorescence Polarization The following series of Examples exemplify the efficacy of using the disclosed invention in measuring protease cleavage in the presence of various potentially interfering compounds. Briefly, each reaction comprised mixing three components: 1) a mixture of labeled and unlabeled protease substrates; 2) TEV protease; and 3) the potentially interfering additive. The results are presented graphically in FIGS. 3-14 The reaction buffer contained the following components (final concentrations noted):

Tris, 20 mM

TCEP, 0.3 mM

BME, 1 mM

EDTA, 2.5 mM

At3g16990 in pVP15 (unlabeled), 9 μM

At3g16990 in pVP15 (tetraCys-labeled), 16 nM

TEV Protease, 0.5 μM pH 8.0

TCEP=tri(2-carboxyethyl)phosphine hydrochloride (reducing agent)

BME=β-mercaptoethanol (reducing agent)

EDTA=ethylenediaminetetraacetic acid (chelating agent)

Each stated additive as shown in FIGS. 3-14 was added at the stated concentrations. The TEV protease was added to each reaction last, just prior to placing the reactions into the photometer. The reactions were followed in real-time, at ambient temperature (ca. 22° C.). Fluorescence anisotropy was measured at the time points noted in FIGS. 3-14.

Figure 3:
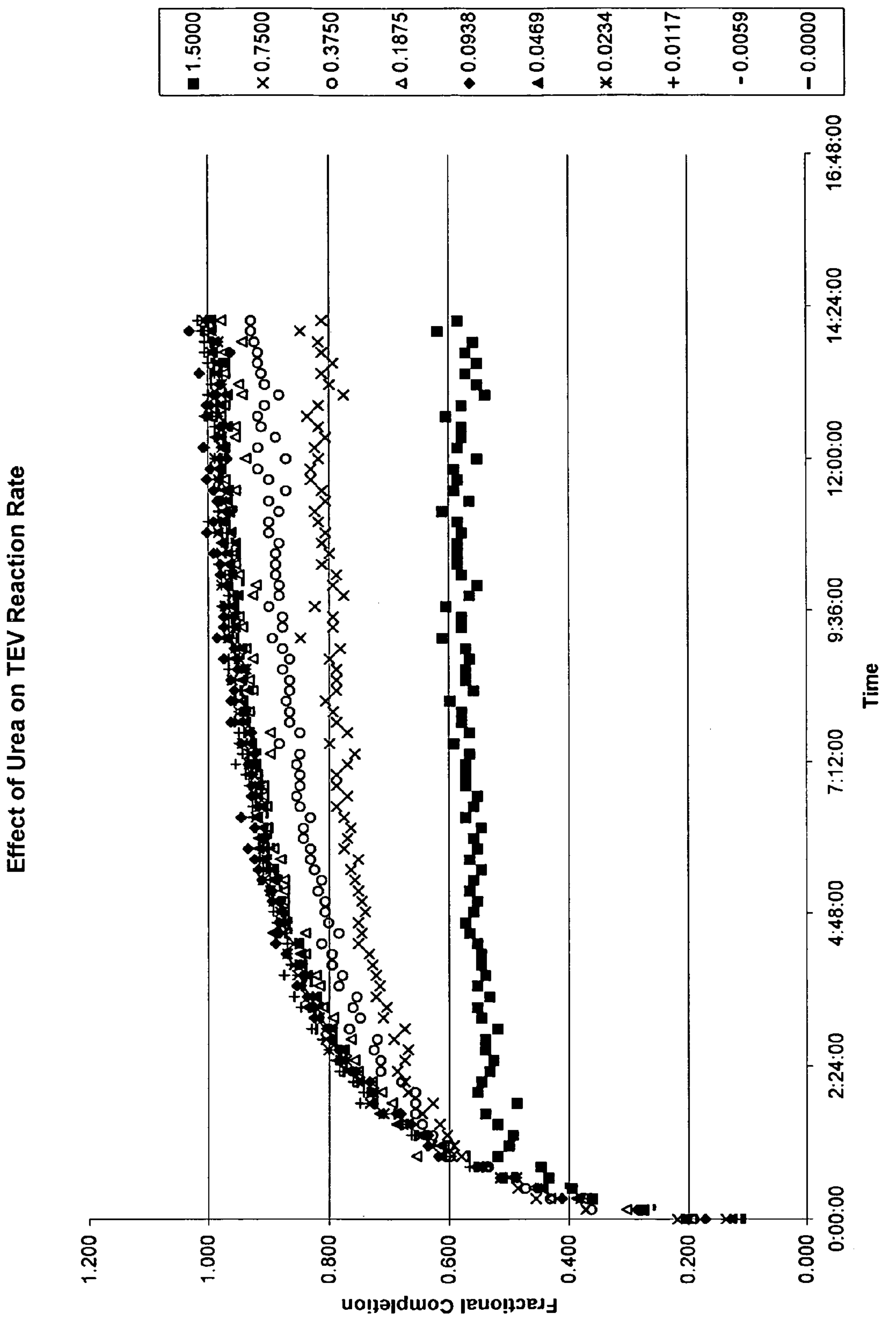
FIG. 3 is a graph depicting the effect of urea concentration (M) on the tobacco etch virus (TEV) protease reaction rate. Fractional completion is shown in the Y-axis; time (hr:min:sec) is shown in the X-axis.
Figure 4:
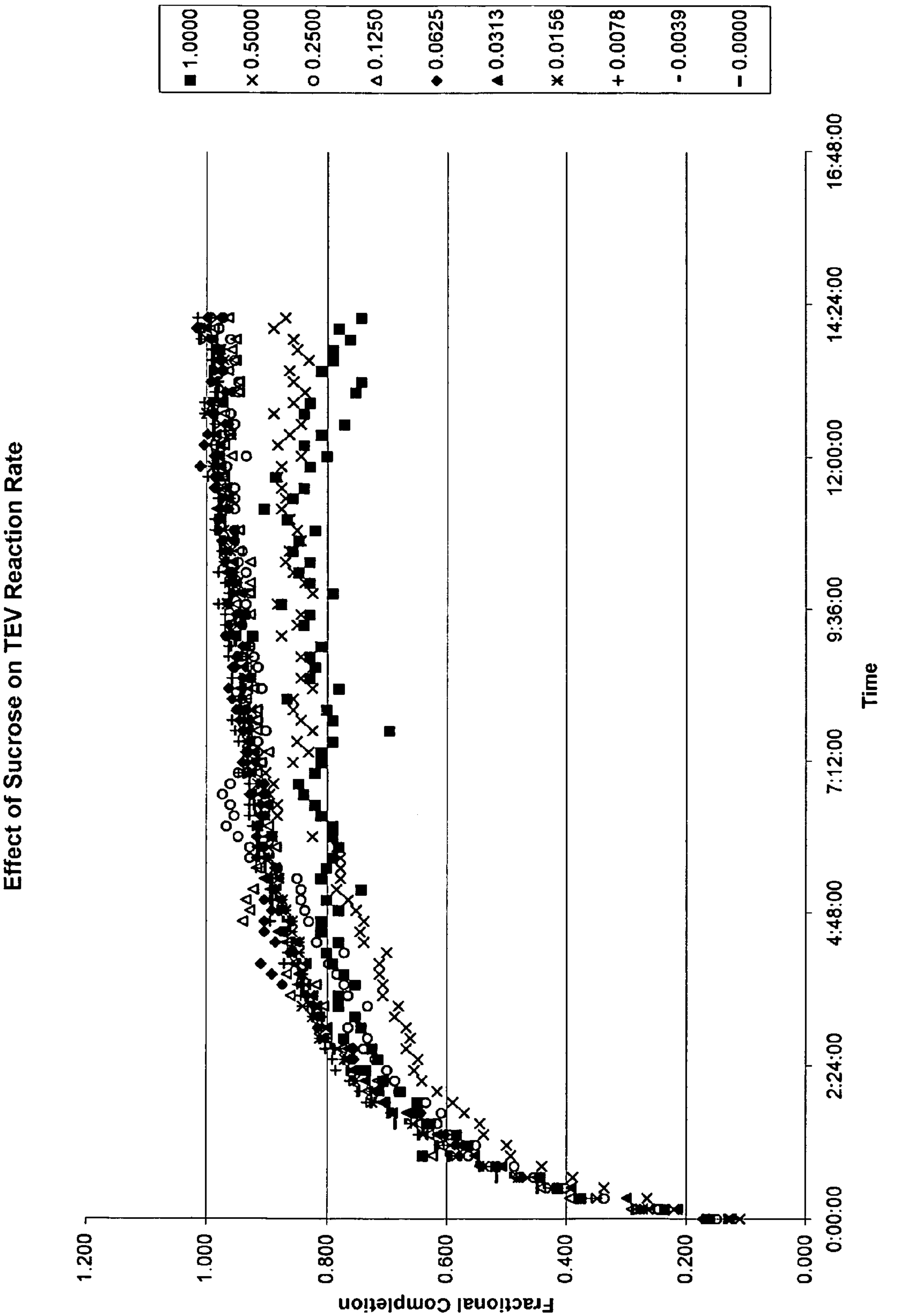
FIG. 4 is a graph depicting the effect of sucrose concentration (M) on the TEV protease reaction rate. Fractional completion is shown in the Y-axis; time is shown in the X-axis.
Figure 5:
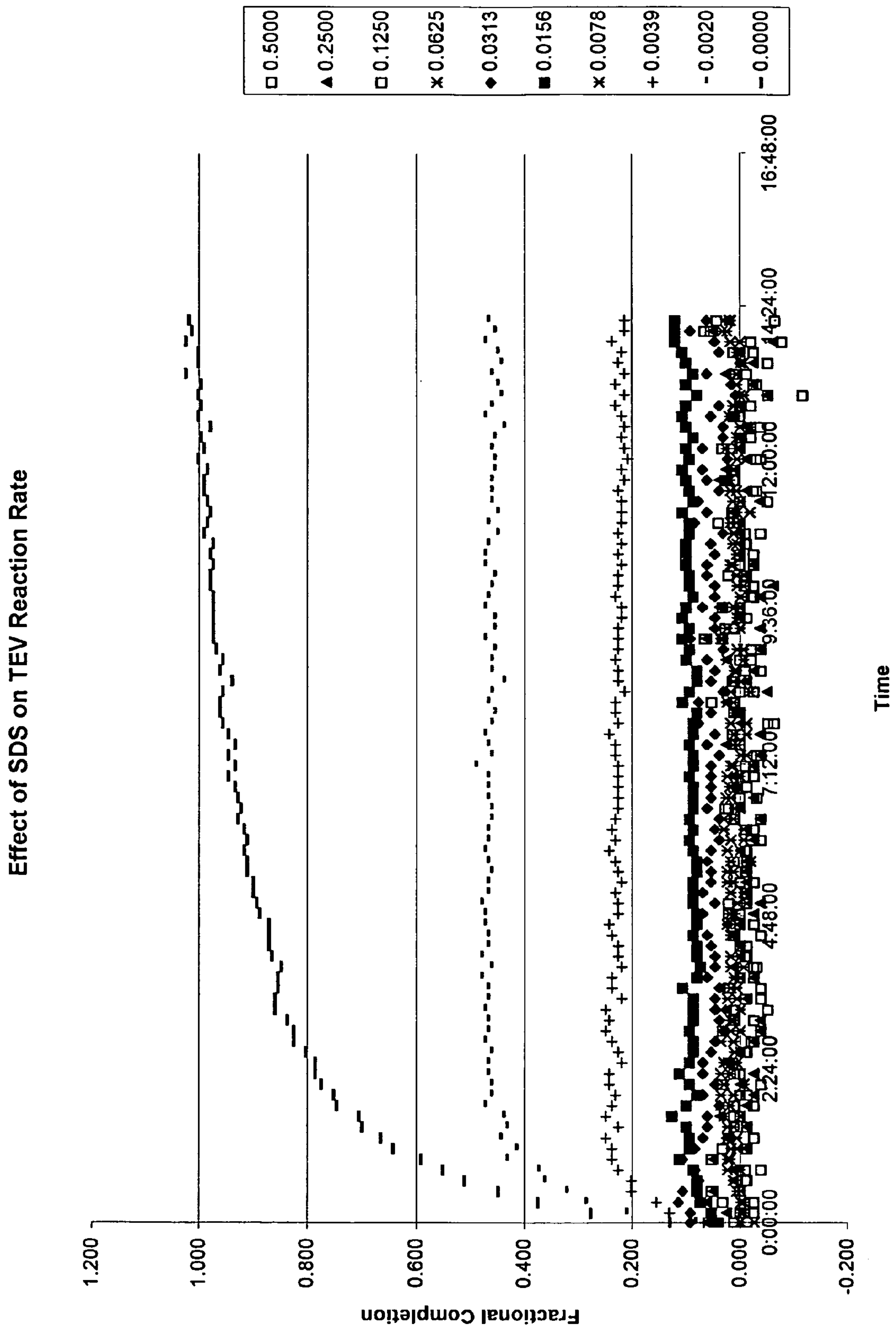
FIG. 5 is a graph depicting the effect of sodium dodecylsulfate (SDS) concentration (wt/vol %) on the TEV protease reaction rate. Fractional completion is shown in the Y-axis; time is shown in the X-axis.
Figure 6:
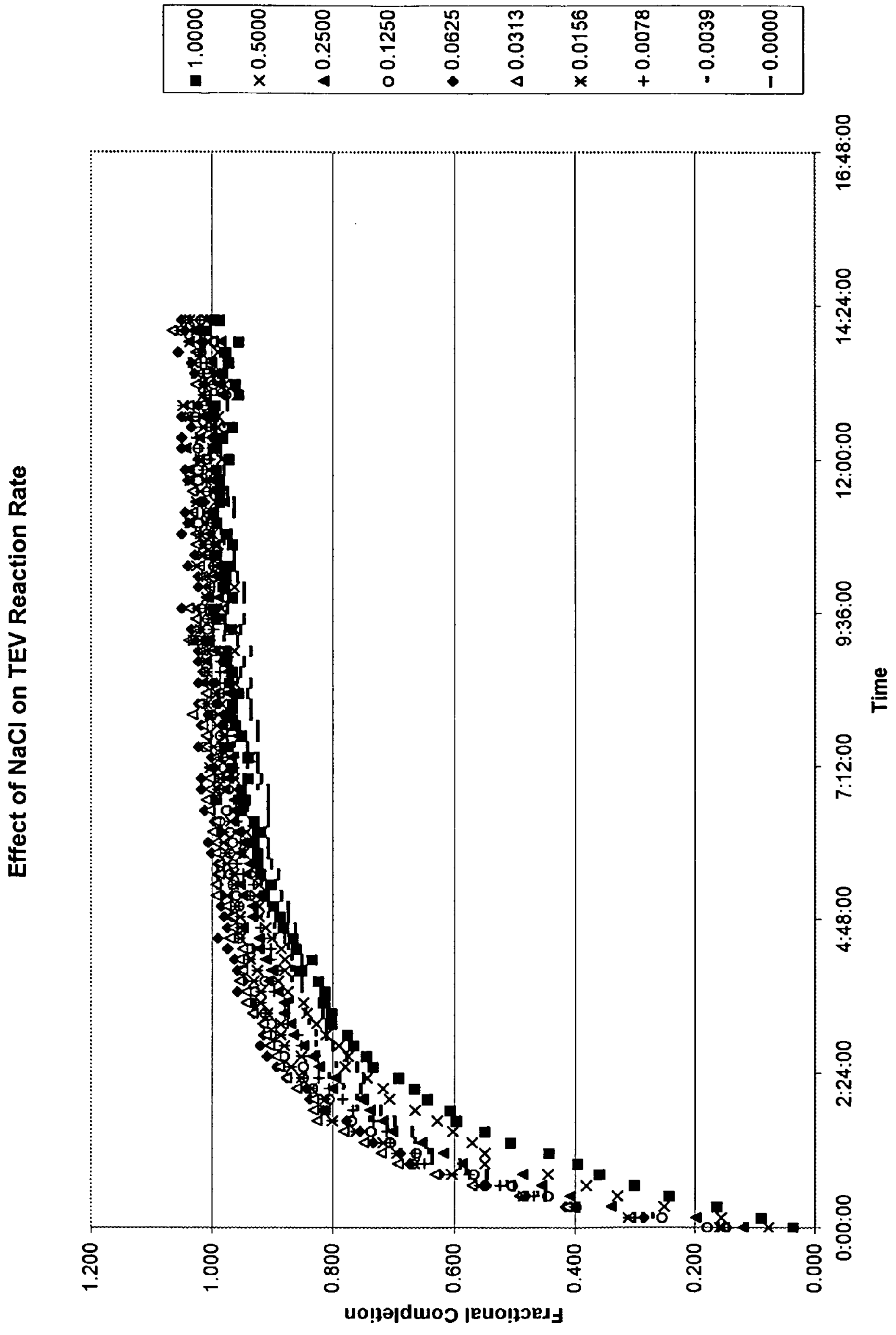
FIG. 6 is a graph depicting the effect of sodium chloride (NaCl) concentration (M) on the TEV protease reaction rate. Fractional completion is shown in the Y-axis; time is shown in the X-axis.
Figure 7:
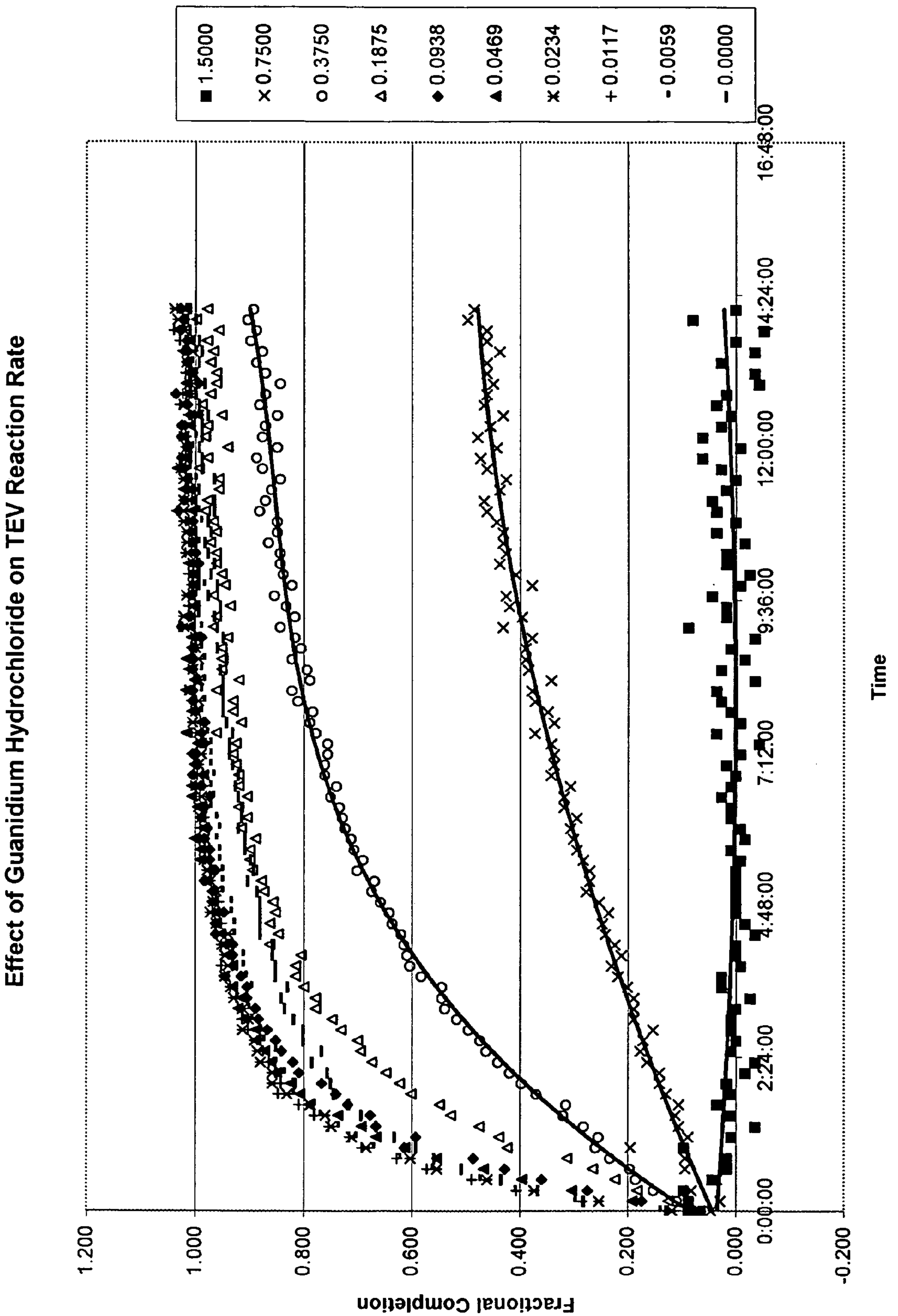
FIG. 7 is a graph depicting the effect of guanidium hydrochloride concentration (M) on the TEV protease reaction rate. Fractional completion is shown in the Y-axis; time is shown in the X-axis.
Figure 8:
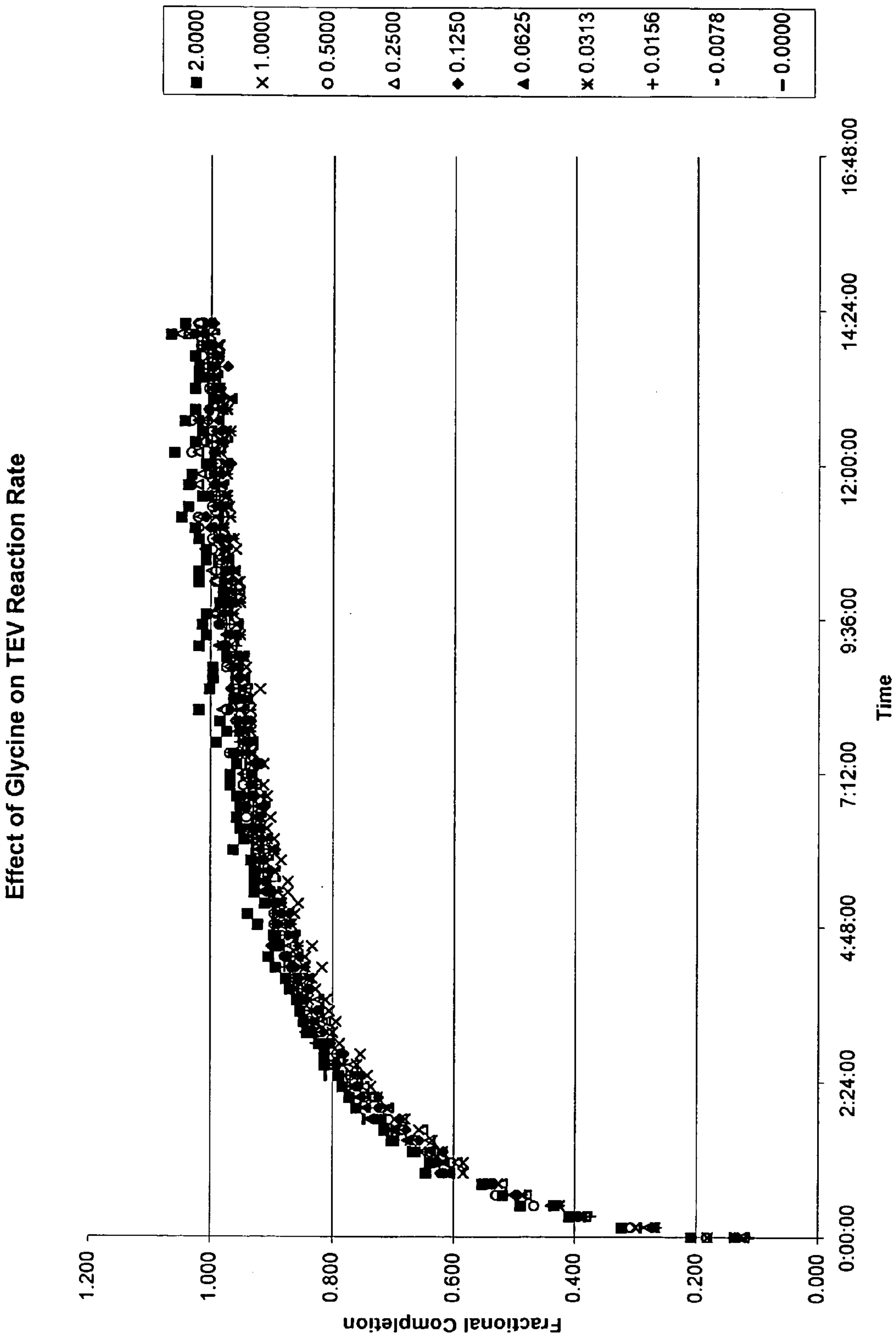
FIG. 8 is a graph depicting the effect of glycine concentration (wt/vol %) on the TEV protease reaction rate. Fractional completion is shown in the Y-axis; time is shown in the X-axis.
Figure 9:
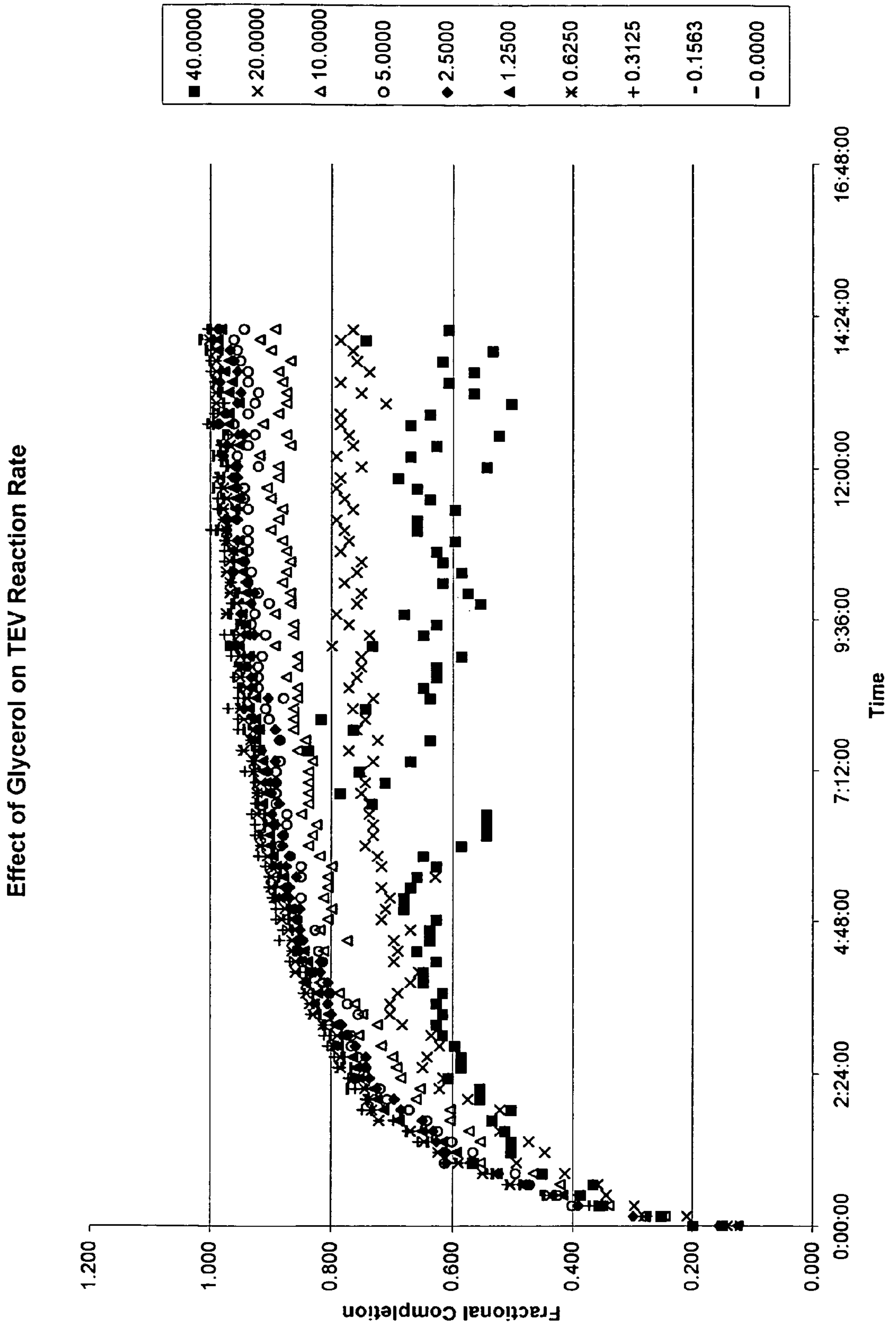
FIG. 9 is a graph depicting the effect of glycerol concentration (vol/vol %) on the TEV protease reaction rate. Fractional completion is shown in the Y-axis; time is shown in the X-axis.
Figure 10:
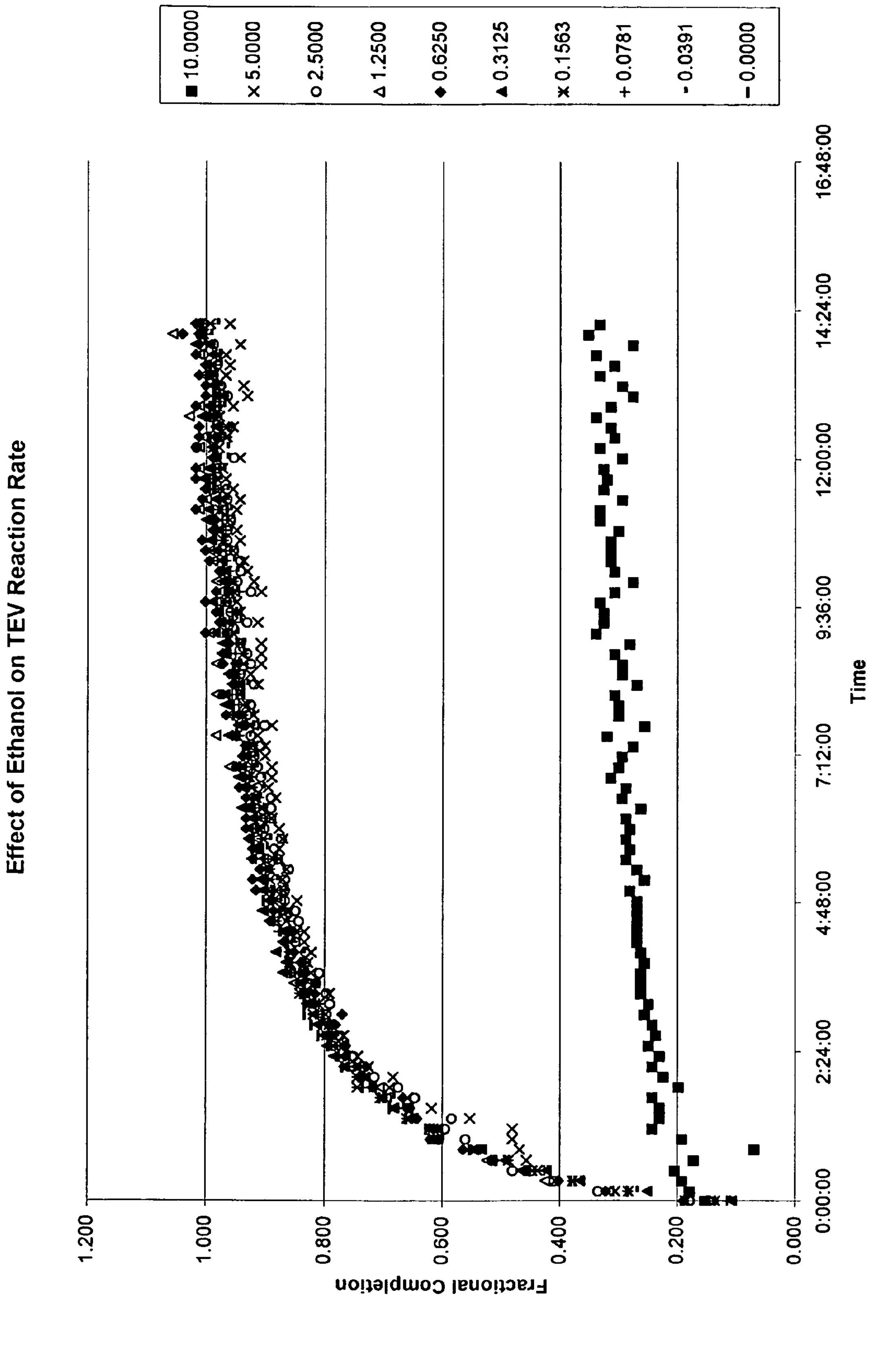
FIG. 10 is a graph depicting the effect of ethanol concentration (vol/vol %) on the TEV protease reaction rate. Fractional completion is shown in the Y-axis; time is shown in the X-axis.
Figure 11:
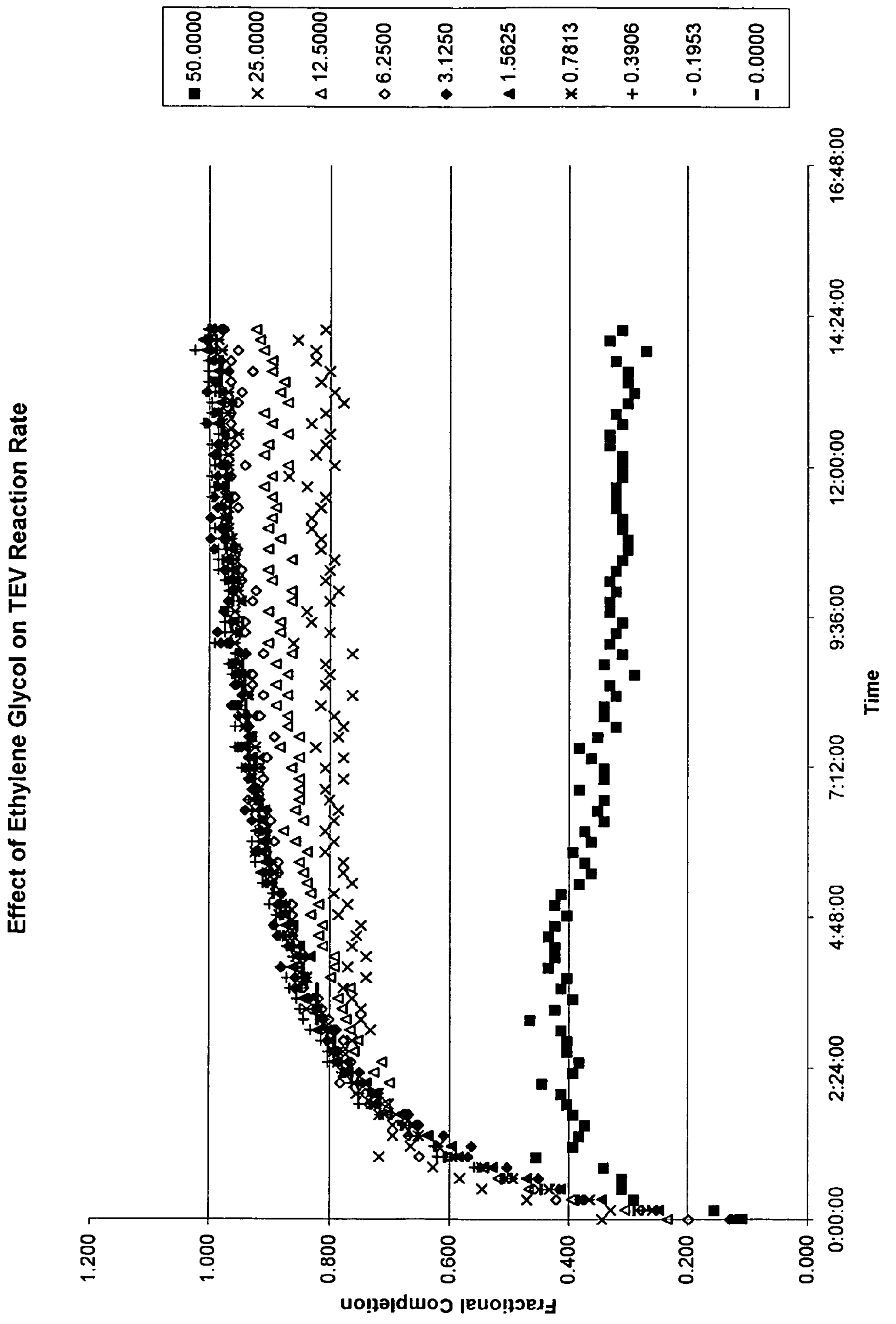
FIG. 11 is a graph depicting the effect of ethylene glycol concentration (vol/vol %) on the TEV protease reaction rate. Fractional completion is shown in the Y-axis; time is shown in the X-axis.
Figure 12:
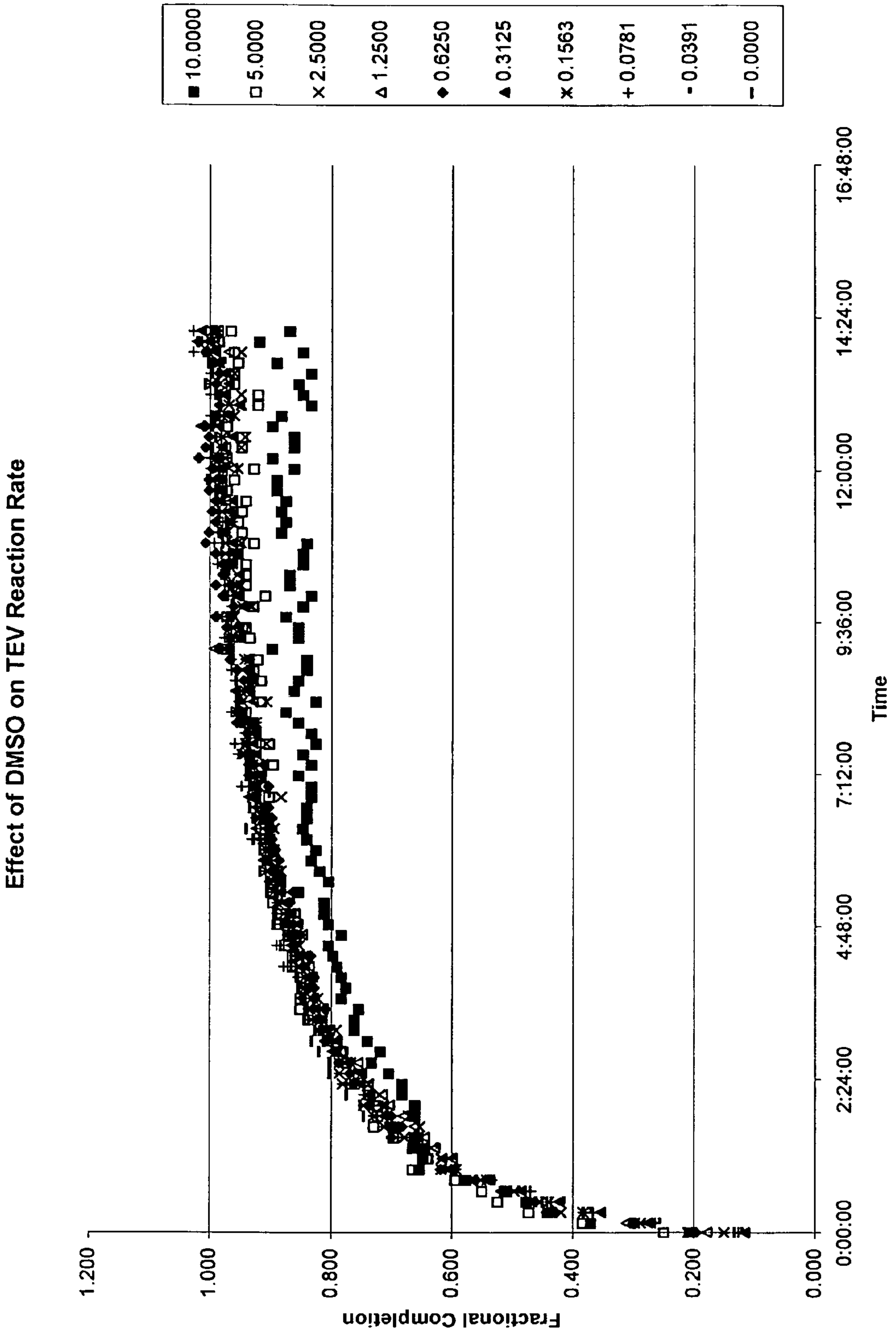
FIG. 12 is a graph depicting the effect of dimethylsulfoxide (DMSO) concentration (vol/vol %) on the TEV protease reaction rate. Fractional completion is shown in the Y-axis; time is shown in the X-axis.
Figure 13:
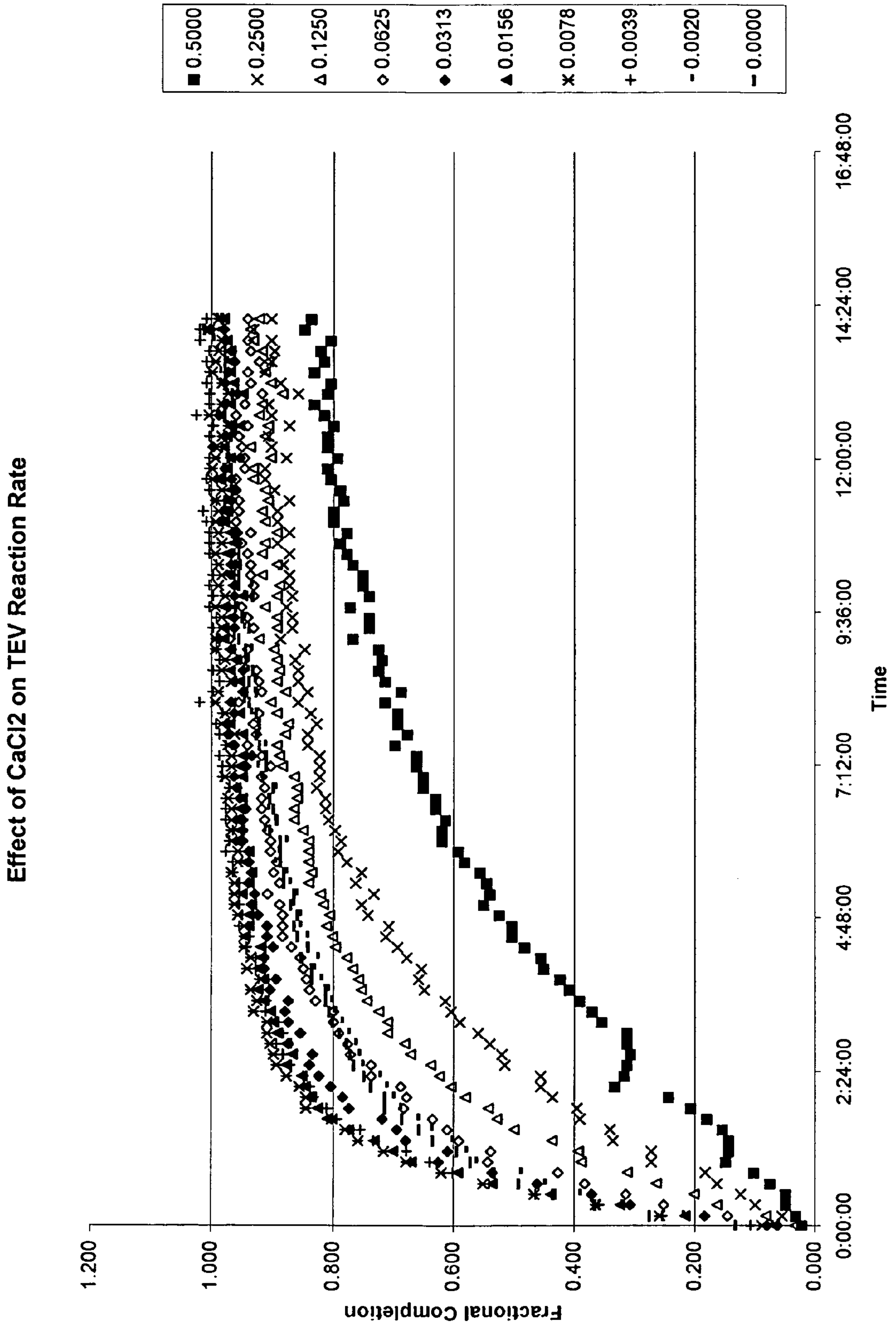
FIG. 13 is a graph depicting the effect of calcium chloride (CaCl2) concentration (M) on the TEV protease reaction rate. Fractional completion is shown in the Y-axis; time is shown in the X-axis.
Figure 14:
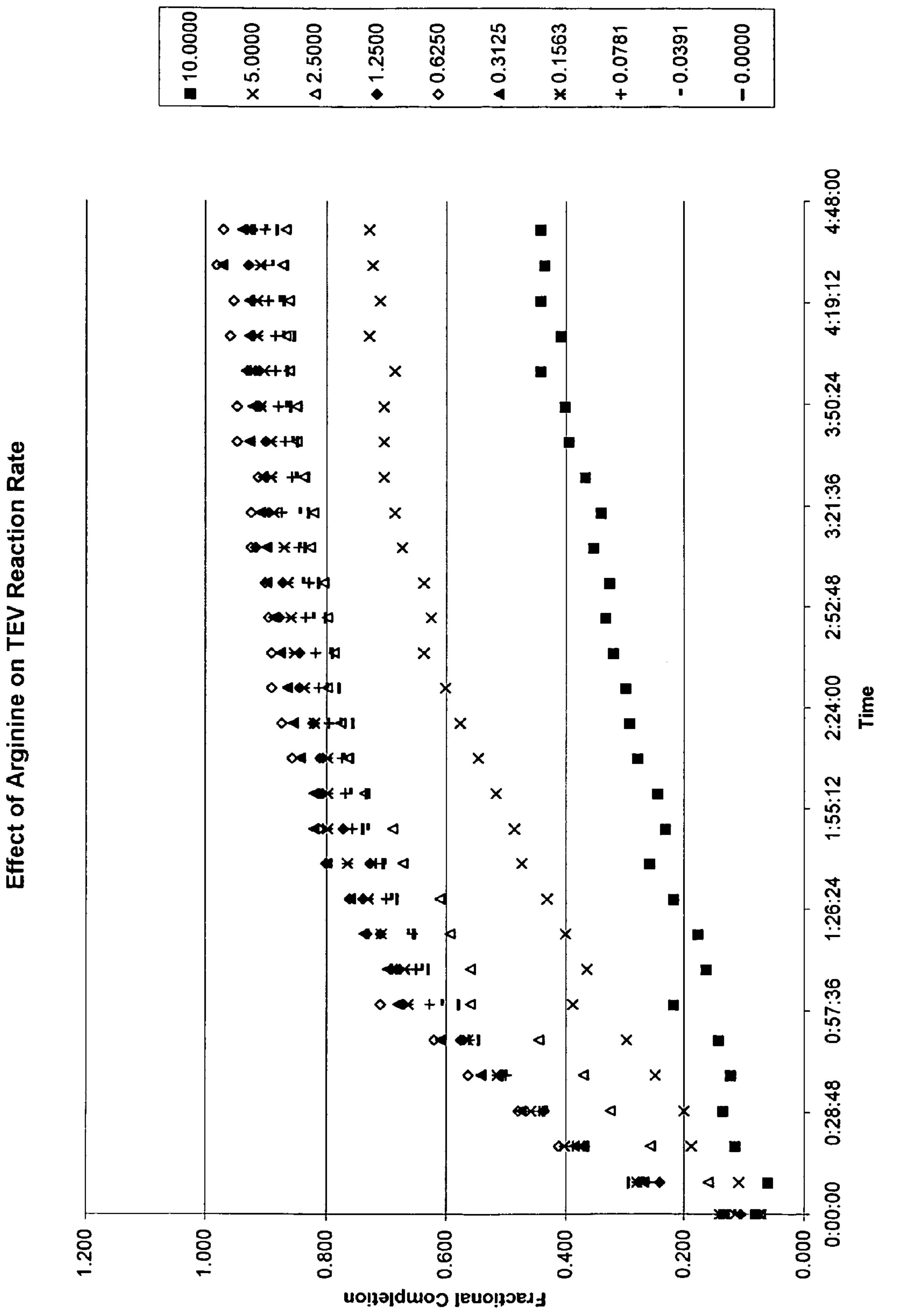
FIG. 14 is a graph depicting the effect of arginine concentration (wt/vol %) on the TEV protease reaction rate. Fractional completion is shown in the Y-axis; time is shown in the X-axis.

The following figures present the fluorescence data for each of the stated additives: FIG. 3: urea (M), FIG. 4: sucrose concentration (M), FIG. 5: sodium dodecylsulfate (SDS) (wt/vol %), FIG. 6: sodium chloride (NaCl) (M), FIG. 7: guanidium hydrochloride (M), FIG. 8: glycine concentration (wt/vol %), FIG. 9: glycerol concentration (vol/vol %), FIG. 10: ethanol concentration (vol/vol %), FIG. 11: ethylene glycol concentration (vol/vol %), FIG. 12: dimethylsulfoxide (DMSO) (vol/vol %), FIG. 13: calcium chloride ($CaCl_2$) (M), and FIG. 14: arginine (wt/vol %).

All protease substrates were expressed in *E. coli* Rosetta pLacI Rare to provide compensation for rare codons (see Kirienko et al. (2004) *Biochemistry* (*Mosc*) 69:527-535; available commercially from Novagen, a wholly-owned subsidiary of EMD Biosciences, Inc., Madison, Wis.). The expression was done in 2-L PET bottles (Millard et al. (2003) *Protein Expr. Purif.* 29:311-320). The protein purification followed typical IMAC purification procedures (see Sambrook & Russell, supra) including elution in an imidazole gradient from 0-350 mM. After SDS-PAGE analysis, appropriate fractions were pooled and desalted into 20 mM phosphate, pH 7.5, containing 100 mM NaCl and 0.3 mM TCEP. Proteins were concentrated to a final concentration of 300-600 μM using centrifugal concentrators. Glycerol (50% v/v) was added to all protease substrates except 26-F and frozen at −20° C. The Arabidopsis targets At3g03410 (expressed from pVP14) and At3g16990 (expressed from pVP15) were flash frozen as drops in liquid nitrogen and stored at −80° C.

A 20% molar excess of the tetraCys reagent was incubated overnight (~12 h) with protein (10-100 μg) at room temperature in 20 mM phosphate, pH 7.5, containing 100 mM NaCl, 0.3 mM TCEP, and 1 mM β-mercaptoethanol. After the labeling reaction, unincorporated fluorophore was removed by two successive cycles of 10-fold dilution and concentration using centrifugal concentrators.

Protease assays were conducted using a combination of 20 μM unlabeled and 40 nM labeled protease substrates unless noted otherwise. TEV protease reactions were conducted in 20 mM Tris-HCl, pH 8.0, containing 100 mM NaCl, 0.3 mM TCEP, 1 mM β-mercaptoethanol, and 5 mM EDTA. Reactions with thrombin, enterokinase, and Factor Xa were performed in the buffer supplied by the manufacturer. Trypsin reactions were carried out in the buffer supplied for thrombin. Assays were carried out in black Cliniplate 384 well plates in a 40 μL reaction volume or in black Greiner 384 well plates using an 80 μL reaction volume. Equal volumes of substrate and protease diluted in reaction buffer were mixed in the assay plates to initiate reactions. Kinetic measurements were begun immediately after mixing. To avoid a long time delay between mixing and the first time measurement, a maximum of 135 assays were conducted in parallel. This decreased the amount of time between mixing and measurement to less than three minutes and allowed the fluorescence anisotropy measured at the first time point to closely approximate the anisotropy of the intact fusion protein. The reaction temperature was maintained between 23° C. and 28° C.

Fluorescence anisotropy was measured using a Tecan 384 Ultra plate spectrofluorimeter. Excitation was at 485 nm (25 nm bandpass) and emission was measured at 525 nm (20 nm bandpass). Anisotropy measurements were made at 2 to 5 min intervals for 5 hours. The observed anisotropy is the sum of the anisotropy of the individual fluorescent components, or $r_{obs}=\Sigma f_i r_i$, where $r_{obs}$, is the observed anisotropy, $f_i$ is the fractional fluorescence intensity of component i, and $r_i$ is the anisotropy of component i. See J. Lakowicz, "Principles of fluorescence spectroscopy," Kluwer Academic/Plenum Publishers, New York, 1999. For a two-state system with the fluorophore attached to either the intact fusion protein or to the small peptide produced by proteolysis, the fractional extent of reaction is given by $\xi=(r_f-r_{obs})/(r_f-r_c)$, where $r_f$ is the fluorescence anisotropy of the intact fusion protein and $r_c$ is the fluorescence anisotropy of small peptide. This treatment assumes that there is no difference in the fluorescence intensity of the fluorophore attached to either the fusion protein or the small peptide, and this is justified by the observation that there was no significant change in total fluorescence intensity as the reactions proceeded.

The reaction progress curves were fit with either exponential or linear models depending on the extent of reaction at the end of the measurement period. For less than 20% reaction at the end of the measurement period, a linear model was sufficient to describe the initial reaction rate. Above 20% reaction, an exponential decay model was used. Xfit3-brand software (ID Business Solutions Ltd., Guildford, United Kingdom) was used for curve fitting and statistical analysis. Errors are reported as two standard deviations.

The intensity of protein bands in SDS-PAGE gels was determined using Image J-brand software, version 1.30. This is a public domain program that can be obtained from the National Institutes of Health (Bethesda, Md.).

The plots in FIGS. 3-14 show the effect of increasing the concentration of each particular additive on the cleavage of the tetraCys tag from the expression product (as measured by fluoresence polarization). The data illustrate that the invention is capable of discriminating changes in cleavage rate despite the presence of a wide range of potentially interfering compounds. For example, sucrose (FIG. 4), NaCl (FIG. 6), glycine (FIG. 8), glycerol (FIG. 9), DMSO (FIG. 12), and $CaCl_2$ (FIG. 13) had little or no effect on the fractional completion of the reactions at all of the concentrations tested. In contrast (and not unsurprisingly), urea (FIG. 1), SDS (FIG. 5), guanidium hydrochloride (FIG. 7), ethanol (FIG. 10), ethylene glycol (FIG. 11), and arginine (FIG. 14), showed considerable inhibition of the cleavage reaction at the higher concentrations tested. These combined data show that the reaction protocol disclosed herein is quite robust. In short, the invention disclosed herein yields valuable results even when the reaction is purposefully contaminated.

Example 4

Use of Fluorescent-Labeled Substrates to Determine Protease Activity

FIGS. 17A and 17B show primary fluorescence anisotropy data obtained during the reactions of thrombin (FIG. 17A) and TEV protease (FIG. 17B) with their respective susceptible substrates 25-F and 26-F, respectively. In the absence of protease, both tetracys-labeled $His_6$-tetraCys-X-MBP substrates were stable and gave a relatively constant anisotropy consistent with the size of the intact fusion protein. Incubating the substrate with the appropriate protease gave a time-dependent decrease in fluorescence anisotropy consistent with the release of the small, labeled peptide from the larger fusion protein.

Figure 18:
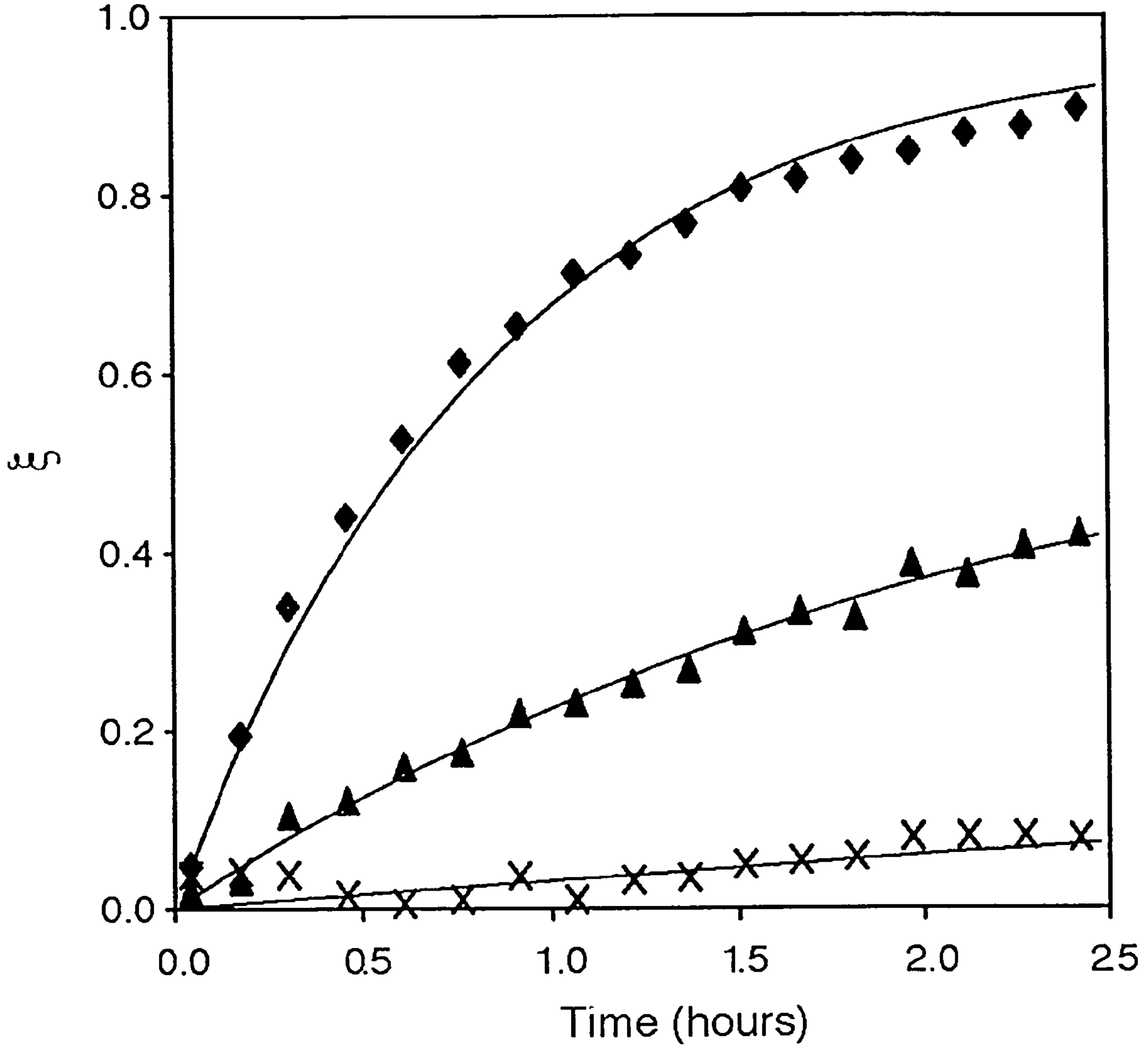
FIG. 18 is a graph depicting fractional conversion data for substrate 26-F incubated with different concentrations of TEV protease: ♦=1.4 μM; ▲=0.35 μM; x=0.09 μM. Measurements were taken at 3 min intervals, while data points are shown at 9 min intervals. The solid lines represent first order exponential fits to the entire experimental data set.

FIG. 18 is a graph depicting a rearrangement of the primary anisotropy data into a progress curve for the reaction of TEV protease with substrate 26-F. The progress curve was well fit by a first order exponential except at the low reaction rate observed from low protease concentrations. In this case, where the extent of reaction was less than 20% at the end of the measurement period, a linear approximation was sufficient to fit the progress curve.

Progress curves obtained for the other proteases were similar, and could also be fit by a first order exponential in order to determine first order decay rates. These initial reaction rates are plotted versus protease concentration in FIGS. 19A and 19B. For trypsin, thrombin and TEV protease, the concentrations of the protein preparations were known and a specific reaction rate was calculated from the slope of the plot of initial reaction rates versus protease concentration (FIG. 19A). Specific reaction rates were calculated based on the slope of linear least squares curve fits shown as solid lines. Specific reaction rates in units of moles substrate proteolyzed per mole of protease per hour were as follows: trypsin; 760±60, thrombin; 240±20, TEV protease; 17.3±0.7. FIG. 19B is a comparison of initial proteolysis rates for thrombin, enterokinase, and Factor Xa as a function of the commercial supplier's reported activity. The units of thrombin were adjusted for equivalence with the unit definition used for enterokinase and Factor Xa. The series represented are: ●=enterokinase with substrate 23-F; ▲=Factor Xa with substrate 24-F; x=thrombin with substrate 25-F. Specific reaction rates in units of nmole substrate proteolyzed per unit enzyme per hour were: Factor Xa, 0.37±0.03; enterokinase, 0.130±0.007; thrombin, 0.20±0.02.

For thrombin, Factor Xa, and enterokinase, activities (U/μL) were reported by the supplier as the amount of a standard fusion protein proteolyzed per unit time. The plot of initial reaction rate versus standard units added to the anisotropy assay is shown in FIG. 19B for these proteases. For all proteases tested, the initial reaction rates were found to be linear with respect to protease concentration except with the highest levels of trypsin and TEV protease (measurements deviating from linearity are not shown in FIG. 19B).

Figure 20:
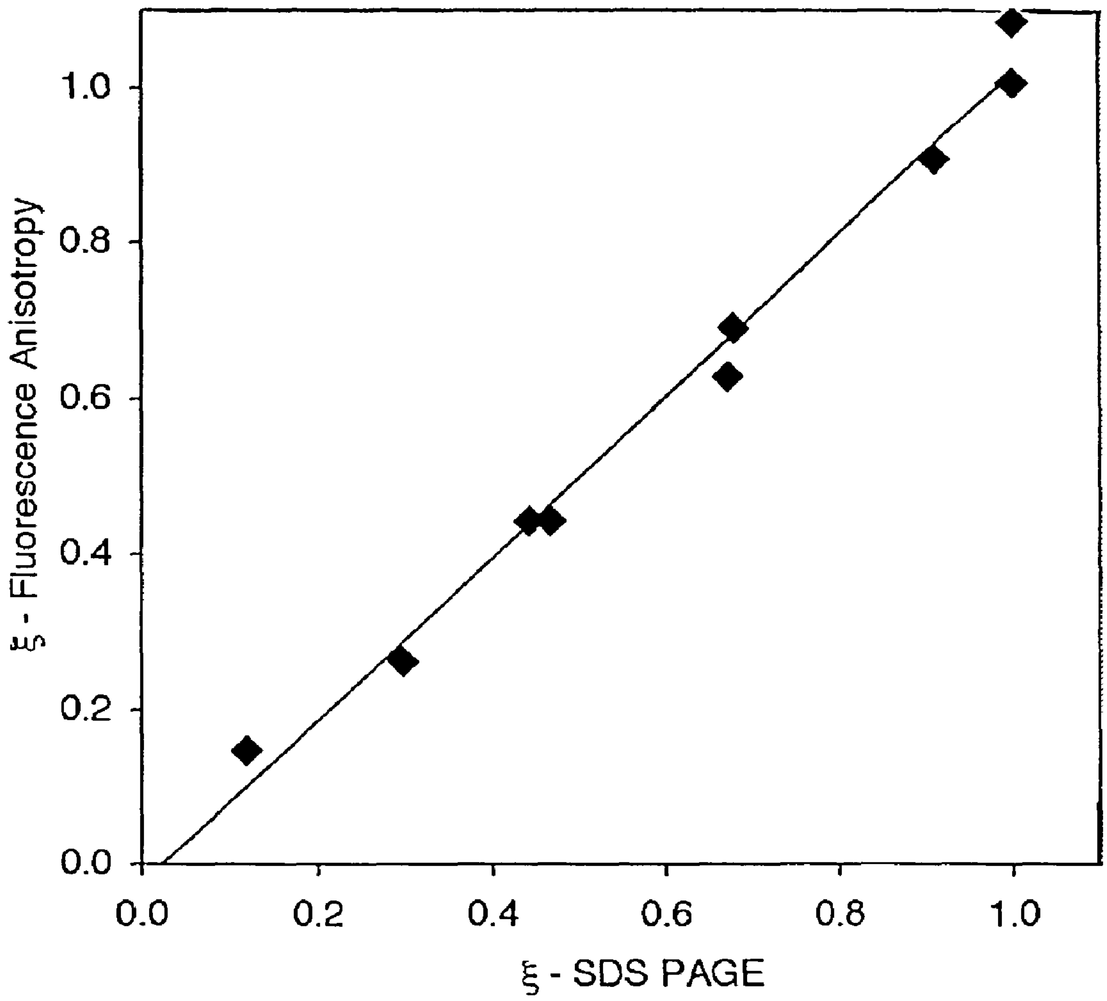
FIG. 20 is a graph comparing the extent of proteolysis determined by either fluorescence anisotropy or by SDS-PAGE with Coomassie staining and densitometry measurements. The solid line is a linear least squares fit, $r^2=0.99$.

By evaluating the primary anisotropy results as shown in FIGS. 17A and 17B, the fractional extent of proteolysis, ξ, can be determined (see Example 3). Likewise, SDS-PAGE coupled with Coomassie staining has been widely applied to determine the extent of proteolysis of a fusion protein (Kapust et al. (2002) *Biochem. Biophys. Res. Commun.* 294:949-955), as the fractional extent of reaction can be approximated from the relative intensities of the intact fusion protein and the released target protein. FIG. 20 shows the equivalence of fluorescence anisotropy and SDS-PAGE as analytical methods to determine the fractional extent of proteolysis. The anisotropy measurement arises from a numerical analysis of a time-resolved measurement, while the SDS-PAGE method is time-discontinuous and requires sample preparation, electrophoresis, gel staining, and gel imaging.

The complete set of $His_6$-tetraCys-X-MBP substrates was investigated for cross-reactivity under the reaction conditions described hereinabove. FIG. 21 shows representative raw anisotropy data for the general protease substrate 22-F and the thrombin substrate 25-F. Relative rates were determined for all protease/substrate combinations by non-linear least squares fitting of the primary data and normalization with the rate determined for the intended substrate of each protease. The relative rates are shown in Table 3. TEV protease was found to react with only 26-F, the substrate containing the consensus TEV protease cleavage site. As expected, trypsin was found to proteolyze all of the substrates tested due to the introduction of Lys residues by the attB recombination sequence used for cloning. Moreover, changes in anisotropy indicated that each of the other three proteases gave variable amounts of substrate-dependent, non-specific proteolysis.

TABLE 3

Relative Rates of Reaction for $His_6$-Cys4-X-MBP Substrates with Different Proteases[a]

| | Substrate[b] | | | | | |
|---|---|---|---|---|---|---|
| Protease | 21F | 22F | 23F | 24F | 25F | 26F |
| Trypsin | 0.3 | 1 | 0.1 | 0.4 | 0.5 | n.d.[c] |
| Enterokinase | 0.5 | 1.3 | 1 | 0.2 | n.d. | 1 |
| Factor Xa | 0.04 | 0.5 | 0.01 | 1 | 0.05 | 0.0 |

TABLE 3-continued

Relative Rates of Reaction for $His_6$-Cys4-X-MBP Substrates with Different Proteases[a]

| Protease | Substrate[b] 21F | 22F | 23F | 24F | 25F | 26F |
|---|---|---|---|---|---|---|
| Thrombin | 0.0 | 0.4 | −0.02 | 0.0 | 1 | 0.0 |
| TEV | 0.01 | 0.0 | −0.02 | −0.01 | 0.0 | 1 |

[a]The initial rates of reaction were determined by fluorescence anisotropy with the indicated combination of protease and substrate. The relative rates were calculated by normalization to the rate determined for the reaction of a protease with the preferred cognate substrate. For example, the trypsin initial rates were normalized with respect to the initial rate determined with substrate 22-F.
[b]N-terminal sequences of protease substrates given in Table 2.
[c]not detected.

Figure 22:
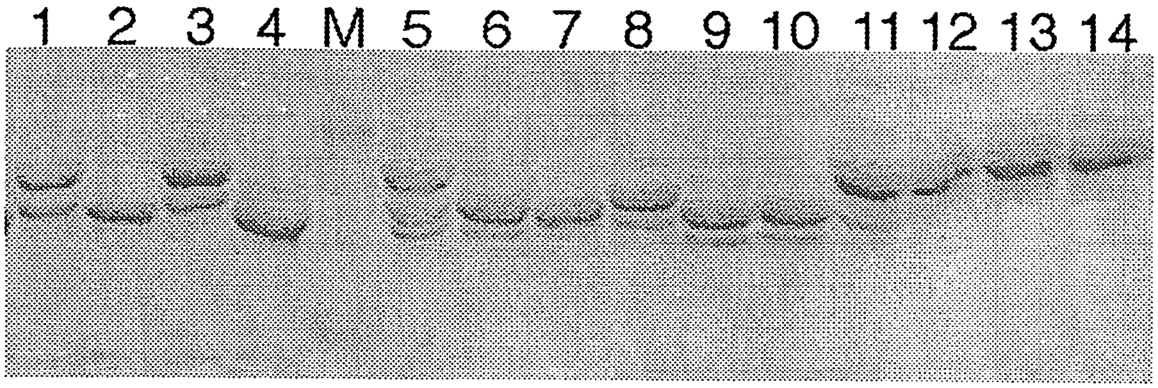
FIG. 22 is a photograph of a gel depicting SDS-PAGE analysis of protease substrates incubated with Factor Xa and TEV protease for 16 h. Lane M, molecular weight standards of 31 and 45 kDa. Lanes 1-5, Factor Xa with substrates 21-F, 22-F, 23-F, 24-F and 25-F, respectively. Lanes 6-10, trypsin with substrates 21-F, 22-F, 23-F, 24-F and 25-F, respectively. Lanes 11-14, TEV protease with substrates 21-F, 22-F, 23-F and 24-F, respectively.

SDS-PAGE analysis with Coomassie staining was performed to further evaluate the predicted low rates of substrate dependent non-specific proteolysis. FIG. 22 shows that Factor Xa reacted with the cognate substrate 24-F (lane 2), and the general protease substrate 22-F (lane 4), as little or no intact fusion protein was detected after an overnight incubation. Furthermore, the low rates of non-specific proteolysis suggested by the fluorescence anisotropy assay for reaction of Factor Xa with substrates 21-F, 23-F, and 25-F (Table 3) were confirmed by SDS-PAGE through the formation of a small amount of a small molecular-weight band (see FIG. 22, lanes 1, 3, and 6).

For TEV protease, the TEV substrate with Lys in the P1' position, 21-F, (lane 7) underwent a minor amount of proteolysis, shown by both the anisotropy and the SDS-PAGE assays. Other studies have shown that the substitution of Lys into the P1' position of an otherwise intact TEV protease recognition site reduces $k_{cat}/K_m$ by more than an order of magnitude for peptide based substrates, Kapust et al. (2002) *Biochem. Biophys. Res. Commun.* 294:949-955. This measurement performed with intact protein substrates shows that Lys is not well tolerated by TEV protease in this context either.

Two *Arabidopsis thaliana* genes were expressed in pVP14 and pVP15 to establish whether the anisotropy assay could be used to monitor removal of fusion tags using TEV protease in a more general fashion. FIG. 23A shows time-dependent decreases in anisotropy for both of the Arabidopsis protein fusions tested that were similar to that observed for reaction of the $His_6$-tetraCys-X-MBP substrates.

FIG. 23B shows anisotropy changes for proteolysis of a fusion protein produced from pVP15. This fusion protein has the schematic structure shown in FIG. 15B, where the tetraCys motif is located between MBP and the Arabidopsis target protein and is flanked by on both sides by TEV protease sites. Thus pVP15 provides a fundamentally different context for proteolytic processing of fusion proteins than the N-terminal modification provided by pVP14. Reaction at both protease sites is required to liberate the ~3 kDa tetraCys motif, which by virtue of its small, constant size provides a constant, low anisotropy upon complete proteolysis.

As with proteolysis from pVP14, a time-dependent decrease in anisotropy was observed for proteolysis of Arabidopsis targets from the pVP15-derived fusion protein. Because two protease sites were present in these fusion proteins, proteolysis could potentially release four different fluorescent species. These include the intact fusion protein, a labeled target protein arising from proteolysis at the site on the N-terminal side of the fluorophore, a labeled MBP arising from proteolysis at the site on the C-terminal of the fluorophore, and the labeled tetraCys motif arising from proteolysis at both sites. Because each of these species could potentially exhibit a unique anisotropy, it is notable that the overall change in anisotropy was well fit as a single exponential. Multiple reaction schemes could account for this behavior, and making use of different proteases in the pV15 construct can test these possibilities.

Fluorescence anisotropy has been used to monitor proteolysis reactions, but these previous efforts were limited by the use of conventional, non-specific fluorophore labeling reagents, which yield heterogeneous substrates containing multiple labels. The development of bis-arsenical fluorophores has made it possible to label proteins fluorescently at a specific position by introduction of the tetracys motif. Adams et al. (2002) *J. Am. Chem. Soc.* 124:6063-6076. Specific protein labeling, as used in the present invention, opens up the possibility for many in vivo and in vitro applications that are not possible using traditional fluorophore labeling reagents. See Griffin, Adams, Jones, and Tsien (2000) *Methods Enzymol.* 327: 565-578, and Griffin, Adams, and Tsien (1998) *Science* 281:269-272.

After in vitro introduction of the site-specific protein label, the assay method disclosed herein enables real-time monitoring of proteolysis. One advantage of the present invention as compared to other proteolytic assays is that because the present method uses a site-specific fluorescent complex, the method excels at monitoring the cleavage of a single peptide bond. By making use of model substrates containing a tetracys motif and *E. coli* MBP, the activity of different proteases can be studied after modifying the linker peptide between the tetraCys motif and MBP to contain the protease recognition site of interest. Thus, the present invention can be used to measure the specificity of any given protease for any putative recognition sequence. A comparison of proteolysis extent determined using the present invention with the widely accepted method of SDS-PAGE gave a highly favorable correlation, as shown in the least-squares fit presented in FIG. 20. In addition, initial velocity data for proteolysis was linear with respect to the concentration of all proteases tested (within the limits imposed by the instrumentation and the fundamental conditions of the reactions). Taken together, the results demonstrate that fluorescence anisotropy-based method disclosed herein can indeed be applied to monitor specific protease activity.

In some circumstances, the initial rates for proteolysis deviated from linearity at high concentration of protease. For TEV protease, linearity was not maintained for concentrations above 2 μM. Without being limited to any underlying physical mechanism, because the substrate concentration was 20 μM, the steady-state kinetics assumption of the availability of a large excess of substrate may no longer be valid. For trypsin, a limitation of the instruments used to measure the reaction was likely responsible for non-linearity because the time required to obtain the individual anisotropy time point measurements approached the time constant of the proteolysis reaction itself. In certain embodiments of the invention, anisotropy measurements taken with the multi-well plate reader require two measurements; one parallel to the plane of excitation polarization and one perpendicular to the excitation plane. In other embodiments, this process required a minimum of 24 seconds to complete for a single sample and as long as 7 min to complete when 384 samples were measured in parallel. When analyzing certain enzymes, the protease reactions take place over a sufficiently long time scale that compensation for the delay between mixing and the first measurement is not necessary. However, the large changes in anisotropy that occurred in short time periods with the higher concentrations of trypsin (trypsin is also the protease with the highest turnover number, see FIG. 19) resulted in measurement inaccuracies that may have affected the initial rate determination. If necessary, optimization of the concentration of the protease being studied or the number of samples under investigation can help to obviate this problem in practice.

The turnover number determined for trypsin was 3-fold greater than that observed for thrombin and 10-fold greater than for TEV protease (see FIG. 19A) for reactions with their cognate $His_6$-tetraCys-X-MBP substrates. The lower reaction rate for TEV protease may be a result of the stringent substrate specificity for this enzyme, which demands an extended substrate-protein interaction for catalysis, Phan et al. (2002) *J. Biol. Chem.* 277: 50564-50572. When compared on a unit activity basis, Factor Xa, enterokinase, and thrombin had specific reaction rates within a factor of three for proteolysis of their cognate $His_6$-tetraCys-X-MBP substrates. Although not large, this variation may be due to intrinsic catalytic properties of the different enzymes, differences in the protein substrates used by the manufacturer to determine the reported protease activity, the reaction conditions used for the anisotropy measurements, minor variations in the $His_6$-tetraCys-X-MPB substrates introduced by the changes in protease recognition site, or other unknown factors.

A consequence of the recombination-based cloning was that all substrates contained two Lys residues in the linker peptide between the tetraCys motif and MBP, allowing trypsin to react at these positions. Not surprisingly, all of the model substrates were susceptible to trypsin proteolysis. MBP was resistant to trypsin except for a small amount of proteolysis at a surface exposed loop near the C-terminal (Arg354 in PDB entry 1ANF; Quiocho, Spurlino, and Rodseth (1997) *Structure* 5:997-1015). This small amount of proteolysis was only detected after extended incubation. Release of this small C-terminal peptide from the larger fusion protein would not give a sufficiently large change in mass to be detected reliably by the anisotropy measurements. Consequently, the anisotropy change observed with trypsin proteolysis can be attributed to hydrolysis occurring in the linker peptide between the tetraCys motif and MBP.

The proteases investigated here are commonly used for removing fusion tags from recombinant proteins. Among these, TEV protease and thrombin proved to have the highest fidelity for substrate recognition in these Examples. For TEV protease, significant proteolysis occurred only for substrate 26-F, which was engineered to contain the appropriate recognition site.

Thrombin reacted with protease substrate 25-F, engineered for thrombin susceptibility, but also reacted with 22-F, which did not contain the accepted thrombin recognition sequence. Matrix-assisted laser desorption ionization mass spectrometry (MALDI-MS) of reaction mixtures revealed a fragment consistent with proteolysis after Arg28 of substrate 22-F, a finding consistent with the thrombin P1 specificity. Moreover, enterokinase and Factor Xa reacted well with substrates that did not contain protease recognition sites designed for those proteases (see Table 3). Nonspecific proteolysis has been reported in the past for these enzymes (see Jenny, Mann, and Lundblad (2003) *Protein Expr. Purif.* 31:1-11), which has motivated the use of the more specific viral proteases such as TEV protease for fusion protein processing. All of the nonspecific proteolysis observed with enterokinase and Factor Xa occurred within the linker peptide between the tetracys motif and MBP.

Assays using the $His_6$-tetraCys-X-MBP substrates showed the potential for using fluorescence anisotropy to monitor proteolysis reactions. In practice, the construct depicted schematically in FIG. 16A would also be suitable for investigating expression and proteolysis with a protein known to have high solubility, such as MBP. For other target proteins, solubility can be dramatically enhanced by expression as a fusion protein with a solubility domain (MBP, thioredoxin, glutathione-S-transferase, NusA, etc.; see FIG. 16B). Assembly of this type of multi-domain fusion protein places the protease site in a different structural context than at the N-terminal position. The results depicted in FIG. 23B show that anisotropy can be reliably used to monitor proteolysis from this multi-domain fusion context as well.

The present invention is thus highly useful for monitoring, measuring, and investigating the activity of proteases, in a specific and thoroughly controlled fashion. Upon labeling of protein fusions incorporating the tetraCys motif in functional proximity with protease recognition sites with bis-arsenical fluorophores, proteolysis can be monitored in real-time by the use of fluorescence anisotropy, a technique that is well suited to high-throughput implementation. The sensitivity of the fluorescence-based anisotropy assay and the reliability offered by numerical analysis of time-resolved data also make the present invention highly useful to determine optimum protease reaction conditions. The method can also be used to evaluate alternative linker peptides in multi-domain fusion proteins. The method can also be used to investigate and characterize inhibitors of protease reactions.

Example 5

Small-Scale Screening of Protein Expression, Purification, and Cleavage to Optimize Large-Scale Protein Production This Example demonstrates the utility of the present invention to predict and optimize the expression and purification behavior of target proteins for large-scale protein production. The initial small-scale expression and analysis of the target protein allows different variables to be studied without the time and expense of large-scale efforts. Growth of the colonies and analysis of the expressed target protein are both performed in high-throughput formats, compatible with 96-well or 384-well plates (or any other suitable high-throughput format).

In this Example, the procedure uses a dual cleavage-compatible vector with a tetraCys motif disposed between the cleavage sites. The two cleavage sites can be the same as one another or different. As shown in this Example, the two cleavage sites are different: an HRV 14 3C cleavage site and a TEV cleavage site, which allows for differential cleavage of the corresponding fusion protein. An illustrative working example of this type of vector is designated pVP-X4, the sequence of which is presented in SEQ. ID. NO: 38. The pVP-X4 vector can be modified through incorporation of specific sequences using any of several methods known to those skilled in the art, some of which are described in Sambrook and Russell (supra) to allow expression of proteins comprising the following N-terminal fusion tags:

$His_8$-Solubility Domain-HRV 14 3C Protease Cleavage Site-TetraCys-att B1-TEV Protease Cleavage Site-Target Protein.

More specifically, and as noted in the annotations to SEQ. ID. NO: 38, the key DNA elements of pVP-X4 are as follows:

| Base Pair No. | Feature |
|---|---|
| 1-829 | β-Lactamase (Ampicillin Resistance) |
| 1149-1151 | Start codon |
| 1155-1178 | Poly Histidine tag (His8) |
| 1179-1196 | Cloning site for solubility domain insertion including NsiI and PacI sites |
| 1197-1220 | HRV 14 3C protease recognition sequence |
| 1221-1238 | TetraCys motif |
| 1239 | Start of att R1 recombination site |
| 6489-6520 | β-Lactamase (Ampicillin Resistance) |
| 4052-5136 | Lac I gene |
| 5331 | ColE1 origin of replication |

The origins of several of these regions are as follows:

| Base Pair No. | Origin |
|---|---|
| 1-1122 | pQE80 from Qiagen |
| 1123-1147 | pQE30 from Qiagen |
| 1148-1238 | Designed by the inventors and ordered from IDT DNA (Coralville, Iowa) |
| 1239-2936 | Gateway cassette from Invitrogen (catalog no. 11828-029) |
| 2949-2957 | Designed by the inventors ordered from IDT DNA |
| 2958-2990 | pET 43 from Novagen |
| 2991-6250 | pQE80 from Qiagen |

The solubility domain may comprise any solubility domain now known or developed in the future, including any of a number of different domains that have been reported in literature. pVP-X4 contains the *E. coli* maltose binding protein (MBP) as a solubility domain. Other solubility domains (or “solubility tags”) that can be used in the present invention include, but are not limited to poly-His, GST (glutathione S-transferase), Protein A, CBP (calmodulin binding peptide), CBD (cellulose binding domain), S-tag, Trx (thioredoxin), NusA (N utilization substance A), IMPACT (a chitin binding domain with intein sequences), TAP tag (tandem affinity purification: CBP+ Prot A tags with an intervening TEV cleavage site). For a detailed review of solubility tags, see Bauer & Kuster (2003) *Eur. J. Biochem.* 270:570-578.

The overall method includes the following steps: small scale expression, cell harvest and preparation of the cell lysate; purification of the fusion protein, HRV14 3C protease cleavage, analysis of the products from the first round of protease cleavage, TEV protease cleavage, and analysis of the products from the second round of protease cleavage. The data gathered during these steps include: total protein expression level (fluorescence intensity), soluble protein expression level (fluorescence intensity), quality of protein released by HRV14 3C protease (evaluated via SDS-PAGE), yield of protein released by HRV14 3C protease (fluorescence intensity), and percentage of proteolysis of target protein by TEV protease (fluorescence anisotropy).

Materials:

(Quantities listed are the amounts required for expression and analysis of 96 targets in 96-well microtiter plates. Preferred commercial suppliers are noted):

96-well growth blocks—Qiagen catalog no. #19579

96 well lysis plates—Fisher catalog no. #05-500-63

96 well purification plates—Greiner catalog no. #651101/ISC T-3016-3

384 well fluorescence plates—Greiner catalog no. #781209

Buffers:

Resuspension Buffer—10 mL 20 mM $NaH_2PO_4$ 100 mM NaCl

6 U/mL Benzonase Nuclease (Novagen)

9,000 U/mL rLysozyme (Novagen)

20 μM E-64 protease inhibitor (EMD Biosciences)

0.3 mM Triscarboxyethylphosphine (TCEP)

pH adjusted to 7.5

Wash Buffer—10 mL 20 mM $NaH_2PO_4$ 500 mM NaCl 35 mM imidazole 0.3 mM TCEP pH adjusted to 7.5

HRV14 3C Protease Cleavage Buffer—10 mL 200 mM NaCl 20 mM $NaH_2PO_4$ 0.3 mM TECP pH adjusted to 7.5

SDS Buffer Containing TetraCys Reagent

1% Sodium Dodecyl Sulfate (SDS)

25% (vol/vol) Glycerol 100 mM Tris-HCl, adjust to pH 6.8

60 mM TCEP

18 μM tetraCys reagent (Do not add bromophenol blue to SDS buffer)

Development Solution—15 mL 20 mM $NaH_2PO_4$ 100 mM NaCl 5 mM EDTA 0.3 mM TCEP 2.14 μM tetraCys Reagent TEV Protease Dilution Buffer—1 mL 20 mM NaH2PO4

100 mM NaCl 5 mM EDTA 0.3 mM TCEP

Diluted TEV protease—500 μL

100 μL TEV protease at 1 mg/mL in 50% glycerol

400 μL vol/vol protease dilution buffer

Diluted Glycerol (To match glycerol concentration of diluted TEV protease in negative control)—500 μL 100 μL (vol/vol) 50% glycerol 400 μL (vol/vol) protease dilution buffer Diluted HRV 14 3C Protease—9.0 mL 110 μL HRV 14 3 C Protease (Novagen)

8.9 mL HRV 3C Protease Cleavage buffer

Expression Medium:

Overnight Express LB or TB medium (Novagen protocol) supplemented with appropriate antibiotics (typically ampicillin and chloramphenicol).

SDS-Gel Destain

60% (vol/vol) water

10% (vol/vol) glacial acetic acid

30% (vol/vol) methanol

Small-Scale Expression:

For each target gene being tested for expression, add 400 μL of expression media to an individual well of a 96-well growth block. Inoculate the medium by picking a single bacterial colony with a small pipette tip and drop the tip into a single well. Cover the growth block with gas permeable tape to prevent excessive evaporation and contamination while allowing gas exchange.

For TB autoinduction medium, incubate at room temperature for 24-30 hours on a plate shaker using a speed setting of 7.

Cell Harvest and Lysis:

Transfer 20 μL of culture to a 96-well PCR type plate. This plate will be referred to as the lysis plate. Spin down the plate for 30 minutes as 3000×g. The centrifuge temperature should be set at 4° C. After centrifugation, remove the supernatant by inverting the lysis plate and striking onto a flat surface to remove residual media. Resuspend cell pellets using 100 μL of lysis buffer.

After resuspension, incubate the lysis plate at room temperature for one hour to allow lysozyme to weaken cell membranes. Place the lysis plate on plate sonicator pre-cooled to near 0° C. by using a circulating water bath and/or ice. Sonicate the resuspended cultures for 10 minutes at a power setting of 8. Program the sonicator for 1 minute of sonication followed by a pauses of 15 seconds to allow adjustment of the plate and/or addition of ice. There is normally very little temperature rise using a plate sonicator if proper cooling is maintained during the process.

Total Protein Sample:

Remove 8 μL and add to 24 μL of SDS buffer in a 384-well fluorescence plate. This plate will be referred to as fluorescence plate 1. Spin down the sonicated samples for 30 minutes as 3000×g. The centrifuge temperature should be set at 4° C.

Soluble Protein Sample:

After centrifugation, remove 8 μL and add to 24 μL of SDS buffer in fluorescence plate 1.

Purification:

Add remaining clarified lysate to a flat-bottomed 96-well plate to which 10 μL of His-Mag resin has been added. This plate will be referred to as the purification plate. Agitate purification plate on plate shaker at a low setting for one hour. If analysis for insoluble proteins is required, resuspend the spun down pellets in the lysis plate with 92 μL of lysis buffer. Take 8 μL of resuspended solution and add to 24 μL of SDS buffer in fluorescence plate 1. After one hour of incubation with the resin, separate the His-Mag resin in the purification plate using a magnetic block. Remove the depleted lysate from purification plate using a multichannel pipettor and discard. Add 100 μL of wash buffer to each well of the purification plate. Agitate purification plate on plate shaker at a low setting for 15 minutes. After 15 minutes incubation with wash buffer, separate out His-Mag resin in purification plate using magnetic block. Remove wash buffer from purification plate and discard.

HRV14 3CP Cleavage:

Add 100 uL of HRV 14 3C protease cleavage buffer to each well of the purification plate. Agitate the purification plate on the plate shaker at low setting for 5 minutes. After a 5-minute incubation with cleavage buffer, remove the initial cleavage buffer from purification plate and discard. Add 84 μL of diluted HRV 3C protease to the purification plate. After covering with sealing tape, agitate purification plate on the plate shaker at low setting overnight at room temperature. The next morning, separate out His-Mag resin in purification plate using magnetic block.

Cleaved Protein Sample:

Remove 8 μL from purification plate and add to 24 μL of SDS buffer in fluorescence plate 1. Transfer 8 μL of each sample from the purification plate to two separate wells in fluorescence plate 2, each with 37 μL of development solution per well.

TEV Cleavage:

To one of two wells in fluorescence 2 plate filled with HRV 14 3CP-cleaved samples, add 5 μL of diluted TEV protease. To the other, add 5 μL of diluted glycerol. Incubate fluorescence plate at room temperature for three hours covered with loose plate cover to avoid excessive evaporation.

Analysis:

Incubate fluorescence plate 1 for 10 minutes at 75° C. After incubation, record the fluorescence intensity of all four samples for each target using a plate reader with excitation at 520 nM and emission at 555 nM. Record fluorescence intensity for total, soluble, insoluble, and HRV14 3CP-cleaved samples. Read the fluorescence anisotropy of fluorescence plate 2 samples (both with and without TEV protease added) using a plate reader with an excitation filter of 485 nM and emission filters of 535 nM. Record the anisotropy of TEV-cleaved and negative control wells. Acceptable TEV cleavage is indicated by a maximum anisotropy of 150 mr and a minimum differential anisotropy of 50 mr.

The quality of the purified protein can be determined by running SDS-PAGE of HRV 14 3C Protease-cleaved samples taken from fluorescence plate 1. After recording fluorescent intensity, the samples can be directly loaded onto SDS-PAGE gels. Run SDS-PAGE per recommended conditions. Be sure to include the tetraCys-stained marker proteins. After each run, place the gels into SDS-PAGE gel destain. Take care that container does not includes any residual stain as this will interfere with fluorescence imaging. To image gel, use an imager with an excitation laser of 532 nM and an emission filter of 555 nM. After fluorescence imaging, gels can be Coomassie stained.

The above procedure was applied to the analysis of more than 30 different genes cloned into pVP-X4. Some of these genes are listed in Table 4. The genes begining with the designation "At" in Table 4 refer to *Arabidopsis* genes for which sequence information is available through TAIR; the genes beginning with the designation "BC" in Table 4 refer to Genbank references. In some cases, certain genes could not be cleaved with the TEV protease even though they comprised an apparent TEV protease amino acid recognition sequence. One strategy to deal with this situation was to add a serine-glycine-serine-glycine spacer sequence to introduce a TEV cleavage site through the use of modified PCR primers as described in Sambrook and Russell (supra) between the TEV site and the target gene. This strategy was used for target genes 22 through 29 in Table 4 that are otherwise identical to target genes 6-9, 12, 13, 16, and 19, respectively. A second strategy, used for target genes 33 and 34 was to add native amino acids to the linker as the original N-terminus of functional protein products may have been incorrectly identified. Other than this N-terminal modification, target genes 33 and 34 are otherwise identical to target genes 10 and 11, respectively. This Example demonstrates that by introducing differential cleavage sites, the present invention can be used to measure protein expression, extent of cleavage, and other parameters, at a small scale, prior to endeavoring to duplicate the protein production at larger scales.

TABLE 4

Genes tested in pVP-X427.

| No | | Main ID |
|---|---|---|
| 1 | | At3g02070.1 |
| 2 | | At1g06060.1 |
| 3 | | At1g21050.1 |
| 4 | | At2g38490.1 |
| 5 | | At5g04010.1 |
| 6 | | At3g16565.1 |
| 7 | | At3g63000.1 |
| 8 | | At1g56590.1 |
| 9 | | At1g67320.1 |
| 10 | | At3g25760.1 |
| 11 | | At3g25770.1 |
| 12 | | At5g62780.1 |
| 13 | | At4g09350.1 |
| 14 | | At4g27410.1 |
| 15 | | At1g66420.1 |
| 16 | | At3g17820.1 |
| 17 | | At1g73490.1 |
| 18 | | At1g06540.1 |
| 19 | | BC051168 |
| 20 | | At5g42650.1 |
| 21 | | At4g15440.1 |
| 22 | 6 SGSG | At3g16565.1 |
| 23 | 7 SGSG | At3g63000.1 |
| 24 | 8 SGSG | At1g56590.1 |
| 25 | 9 SGSG | At1g67320.1 |
| 26 | 12 SGSG | At5g62780.1 |
| 27 | 13 SGSG | At4g09350.1 |
| 28 | 16 SGSG | At3g17820.1 |
| 29 | 19 SGSG | BC051168 |
| 30 | | BC008304 |
| 31 | Alt Sig Seq | At1g13280 |
| 32 | Alt Sig Seq | At5g42650 |
| 33 | Alt Sig Seq | At3g25770 |
| 34 | Alt Sig Seq | At3g25760 |

Example 6

Screening for Protease Activity and Inhibition Using the Present Invention

This Example demonstrates that the present invention can be used to screen inhibitors of protease activity. The putative protease inhibitors can be defined compounds or undefined biological extracts. After initial screening, follow-up studies are then performed to determine the potency of the inhibitors. Thrombin is used in this example, but the protocol provided can easily be adapted to evaluate other proteases and inhibitors thereof.

The protocol proceeds with the following steps: mixing thrombin with potential inhibitor compounds; incubating the protease with tetracys-labeled thrombin substrate(s); measuring the fluorescence anisotropy of the samples after protease cleavage reactions; and then determining the potency of the inhibitor compounds tested.

Materials:

(Quantities listed are the amounts required for expression and analysis of 352 potential inhibitors)

384 well fluorescence plates—Greiner catalog no. #781209

Thrombin Cleavage Buffer—33 mL 20 mM Tris-HCl 150 mM NaCl 2.5 mM CaCl2

Adjust pH to 8.4

Diluted Thrombin—16 mL 0.4 μM thrombin in thrombin cleavage buffer.

Inhibitor Library or Biological Extracts

Dilute potential inhibitors to 200 μM in dimethylsulfoxide or if using biological extracts, use as available.

Substrate Mix—16 mL

Dilute tetraCys-labeled thrombin substrates (such as substrate 25-F described herein) to 20 μM of unlabeled substrate and 200 nM of labeled substrate in thrombin cleavage buffer.

Inhibitor Positive Control

200 μM ZDPP (Z-D-Phe-Pro-methoxypropylboroglycine-pinanediol Ester) (Calbiochem) diluted in DMSO.

Detailed Protocol:

Mixing of Thrombin with Potential Inhibitor Samples:

To all wells in the plate, add 38 μL of diluted thrombin. To wells in column 1, add 2 μL of DMSO (Positive cleavage control). To wells in column 2, add 2 μL of 200 uM ZDPP. To the remaining wells in the plate, add 2 μL of potential inhibitor samples. Cover and incubate for one hour to allow equilibrium inhibition of thrombin.

Incubation of Protease with TetraCys-labeled Thrombin Substrate:

After one hour of incubation, add 40 μL of substrate mix to each well. Cover and incubate for three hours at room temperature.

Measurement of Fluorescence Anisotropy After Cleavage Reactions:

Using an excitation filter of 485 nM and an emission filter of 535 nM, measure fluorescence anisotropy of cleavage reactions. Reactions may be stopped by addition of trifluoroacetic acid, if necessary but this is generally not required as the time scale of the incubation and the measurement are so different.

Determination of Potential Inhibitors:

Inhibited reactions will exhibit fluorescence anisotropy near to that of the inhibitor controls. Uninhibited reactions will exhibit fluorescence anisotropy near that of the positive cleavage controls. Potential inhibitors are ranked within these limits using standard statistical methods.

What is claimed is:

1. A method of measuring protease activity comprising:

(a) providing a protease substrate comprising a solubility tag and a fluorescence tag which is non-fluorescent until incorporated into a fluorescent complex, wherein the fluorescence tag comprises an amino acid motif Cys-Cys-Xaa-Xaa-Cys-Cys;

(b) contacting the protease substrate of step (a) with a reagent capable of forming a fluorescent complex with the amino acid motif, wherein a fluorescent complex is formed; and (c) contacting the fluorescent complex of step (b) with a protease, under conditions wherein the protease is enzymatically active, to thereby yield a mixture; and then (d) measuring fluorescence polarization of the mixture of step (c), and determining the activity of the protease from the fluorescence polarization measured.

2. The method of claim 1, wherein in step (b) the reagent capable of forming a fluorescent complex with the amino acid motif is a biarsenical ligand.

3. The method of claim 2, wherein in step (b) the protease substrate is contacted with a reagent that binds to the fluorescence tag via covalent bonds.

4. The method of claim 1, wherein the solubility tag is selected from the group consisting of: maltose binding protein, N-utilization substance protein A, glutathione S-transferase, bacterioferritin, GrpE, thiroedoxin, and combinations thereof.

5. The method of claim 1, wherein in step (a) a protease substrate is provided that further comprises a purification tag.

6. The method of claim 5, wherein the purification tag is selected from the group consisting of: a His-tag, a calmodulin-binding peptide-tag, a biotin-tag, a strep-tag, Cys-Cys-Xaa-Xaa-Cys-Cys, and combinations thereof.

7. A method of measuring protease activity comprising:

(a) providing a protease substrate comprising a solubility tag and a fluorescence tag which is non-fluorescent until incorporated into a fluorescent complex and having an amino acid motif;

(b) contacting the protease substrate of step (a) with a reagent capable of forming a fluorescent complex with the amino acid motif, wherein a fluorescent complex is formed;

(c) contacting the fluorescent complex of step (b) with a protease under conditions wherein the protease is enzymatically active, to thereby yield a mixture; and then (d) measuring fluorescence polarization of the mixture of step (c), and determining the activity of the protease from the fluorescence polarization measured.

8. The method of claim 7, wherein the fluorescence tag comprises six amino acid residues, four of which are cysteine residues.

9. The method of claim 8, wherein the tetracysteine motif comprises Cys-Cys-Xaa-Xaa-Cys-Cys (SEQ. ID. NO: 1).

10. The method of claim 7, wherein the reagent capable of forming a fluorescent complex with the amino acid motif is a biarsenical ligand.

11. The method of claim 7, wherein the solubility tag is selected from the group consisting of: maltose binding protein, N-utilization substance protein A, bacterioferritin, GrpE, thiroedoxin, and combinations thereof.

12. The method of claim 7, wherein the protease substrate further comprises a purification tag.

13. The method of claim 12, wherein the purification tag is selected from the group consisting of: his-tag, calmodulintag, biotin-tag, strep-tag, Cys-Cys-Xaa-Xaa-Cys-Cys (SEQ. ID. NO: 1), and combinations thereof.

14. A method of measuring protease activity comprising:

(a) providing a protease substrate comprising a solubility tag and a fluorescence tag which is non-fluorescent until incorporated into a fluorescent complex and comprised of amino acid residues; and (b) reacting the fluorescence tag with a reagent in a mixture, wherein the reagent includes arsenic and wherein the amino acid residues of the reagent bind to the tag; wherein the binding of the reagent to the tag generates a fluorescent complex bound to the protease substrate; and then (c) measuring fluorescent polarization of the fluorescence complex of step (b); and (d) contacting the fluorescent complex of step (b) with a protease under conditions wherein the protease is enzymatically active to yield a mixture, wherein the protease may cleave the fluorescent complex from the protease substrate; and then (e) determining the amount of energy emitted from the fluorescent complex remaining bound to the protease substrate, and determining the activity of the protease from the amount of energy emitted.

15. The method of claim 14, further comprising determining the amount of emitted energy from the fluorescent complex cleaved from the protease substrate.

16. A method of measuring protease substrate lability, the method comprising:

(a) providing a protease substrate including a fluorescence tag which is non-fluorescent until incorporated into a fluorescent complex and having an amino acid motif;

(b) contacting the protease substrate of step (a) with a reagent capable of forming a fluorescent complex with the amino acid motif, wherein a fluorescent complex is formed;

(c) contacting the fluorescent complex of step (b) with a protease under reaction conditions wherein the protease is enyzmatically active, to thereby yield a mixture;

(d) measuring fluorescence polarization of the mixture of step (c); and then (e) altering the reaction conditions of step (c) and repeating steps (a) through (d).

17. The method of claim 14, wherein in step (c), the reaction conditions result in the fluorescent complex being cleaved from the protease substrate, and further comprising determining fluorescence emitted by the fluorescent complex cleaved from the protease substrate.

18. A vector for use in determining the activity of a protease comprising:

(a) a first DNA coding sequence that encodes a fluorescence tag which is non-fluorescent until incorporated into a fluorescent complex, the fluorescence tag comprising a component of a fluorescent complex, the coding sequence operationally connected to;

(b) a second DNA coding sequence that encodes a solubility tag, the second DNA coding sequence operationally connected to;

(c) a viral or *E. coli* promoter region, the promoter region operationally connected to;

(d) a DNA sequence coding for a target protein, wherein expression of the vector results in production of a protease substrate comprising the target protein and the fluorescence tag which is non-fluorescent until incorporated into a fluorescent complex.

19. The vector of claim 18, wherein the vector further comprises a second DNA coding sequence that encodes a purification tag.

20. The vector of claim 19, wherein the purification tag is selected from the group consisting of: a his-tag, a calmodulin-binding peptide-tag, a biotin-tag, a strep-tag, and combinations thereof.

21. The vector of claim 18, wherein the viral promoter sequence is physically disposed on the vector before the target protein sequence and the solubility tag coding sequence.

22. The vector of claim 18, wherein the solubility tag is selected from the group consisting of: maltose binding protein, N-utilization substance protein A, glutathione S-transferase, bacterioferritin, GrpE, thiroedoxin, and combinations thereof.

23. The vector of claim 18, wherein the fluorescence tag comprises six amino acid residues, four of which are cysteine residues.

24. The vector of claim 23, wherein the fluorescence tag has the sequence Cys-Cys-Xaa-Xaa-Cys-Cys (SEQ. ID. NO: 1).

25. The vector of claim 18, further comprising a DNA sequence encoding a first protease recognition site.

26. The vector of claim 18, further comprising a first DNA sequence encoding a first protease recognition site and a second DNA sequence encoding a second protease recognition site that is different from the first protease recognition site.

27. A kit for determining the activity of a protease, the kit comprising:

at least one vector, the vector comprising nucleotide sequences encoding a coding region for a purification tag, a fluorescence tag which is non-fluorescent until incorporated into a fluorescent complex, a promoter sequence, a solubility tag, a DNA sequence encoding a first protease recognition site, and a cloning site for insertion of a DNA coding region of a target protein; and a reagent; wherein combining the fluorescence tag with the reagent results in formation of a fluorescent complex, resulting in emission of fluorescent energy from the fluorescent complex.

28. The kit of claim 27, wherein the purification tag is selected from the group consisting of: a his-tag, a calmodulin-binding peptide-tag, a biotin-tag, a strep-tag, and combinations thereof.

29. The kit of claim 27, wherein the promoter is a viral promoter.

30. The kit of claim 27, wherein the solubility tag is selected from the group consisting of: maltose binding protein, N-utilization substance protein A, glutathione S-transferase, bacterioferritin, GrpE, thiroedoxin, and combinations thereof.

31. The kit of claim 27, wherein the fluorescence tag comprises six amino acid residues, four of which are cysteine residues.

32. The kit of claim 27, wherein the fluorescence tag has the sequence Cys-Cys-Xaa-Xaa-Cys-Cys.

33. The kit of claim 27, wherein the vector further comprises a first DNA sequence encoding a first protease recognition site and a second DNA sequence encoding a second protease recognition site that is different from the first protease recognition site.

* * * * *